US008815845B2

(12) United States Patent
Glick

(10) Patent No.: US 8,815,845 B2
(45) Date of Patent: Aug. 26, 2014

(54) 1,4-BENZODIAZEPINE-2,5-DIONES AND RELATED COMPOUNDS WITH THERAPEUTIC PROPERTIES

(75) Inventor: Gary D. Glick, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 63 days.

(21) Appl. No.: 13/508,261

(22) PCT Filed: Nov. 3, 2010

(86) PCT No.: PCT/US2010/055255

§ 371 (c)(1),
(2), (4) Date: Jul. 11, 2012

(87) PCT Pub. No.: WO2011/062766

PCT Pub. Date: May 26, 2011

(65) Prior Publication Data

US 2012/0270862 A1    Oct. 25, 2012

Related U.S. Application Data

(60) Provisional application No. 61/262,017, filed on Nov. 17, 2009.

(51) Int. Cl.
| C07D 403/10 | (2006.01) |
| C07D 401/10 | (2006.01) |
| C07D 471/04 | (2006.01) |
| A61K 31/437 | (2006.01) |
| A61P 9/10 | (2006.01) |
| A61P 9/12 | (2006.01) |

(52) U.S. Cl.
USPC .......................................... 514/221; 540/506

(58) Field of Classification Search
USPC .......................................... 540/506; 514/221
See application file for complete search history.

(56) References Cited

U.S. PATENT DOCUMENTS

| 3,261,828 A | 7/1966 | Uskokovic et al. |
| 3,374,264 A | 3/1968 | Uskokovic |
| 3,384,635 A | 5/1968 | Calabateas et al. |
| 3,415,814 A | 12/1968 | Calabateas et al. |
| 3,847,905 A | 11/1974 | Bub |
| 4,076,823 A | 2/1978 | Wade et al. |
| 4,088,756 A | 5/1978 | Voorhees |
| 4,108,852 A | 8/1978 | Bub |
| 4,110,337 A | 8/1978 | Szarvasi |
| RE30,293 E | 6/1980 | Bub |
| 4,495,101 A | 1/1985 | Klaubert et al. |
| 4,551,480 A | 11/1985 | Stiefel et al. |
| 4,560,684 A | 12/1985 | Sugasawa |
| 4,623,646 A | 11/1986 | Casals-Stenzel |
| 4,751,223 A | 6/1988 | Glamkowski et al. |
| 4,820,834 A | 4/1989 | Evans |
| 4,894,366 A | 1/1990 | Okuhara |
| 4,898,861 A | 2/1990 | Morgan et al. |
| 4,916,138 A | 4/1990 | Ueda |
| 4,929,611 A | 5/1990 | Okuhara |
| 4,946,778 A | 8/1990 | Ladner et al. |
| 5,004,741 A | 4/1991 | Evans |
| 5,041,438 A | 8/1991 | Hsu et al. |
| 5,141,930 A | 8/1992 | Nakao et al. |
| 5,147,872 A | 9/1992 | Golwyn |
| 5,216,148 A | 6/1993 | Klaus et al. |
| 5,288,514 A | 2/1994 | Ellman |
| 5,324,726 A | 6/1994 | Bock et al. |
| 5,391,566 A | 2/1995 | Chakravarty |
| 5,444,092 A | 8/1995 | Collins |
| 5,521,170 A | 5/1996 | Setoi |
| 5,545,568 A | 8/1996 | Ellman |
| 5,559,230 A | 9/1996 | Ogawa et al. |
| 5,591,227 A | 1/1997 | Dinh et al. |
| 5,597,915 A | 1/1997 | Chambers et al. |
| 5,599,352 A | 2/1997 | Dinh et al. |
| 5,633,251 A | 5/1997 | Claremon |
| 5,677,282 A | 10/1997 | Oleksyszyn |
| 5,697,967 A | 12/1997 | Dinh et al. |
| 5,763,437 A | 6/1998 | Sato |
| 5,776,946 A | 7/1998 | McGeer et al. |
| 5,861,380 A | 1/1999 | Gyorkos et al. |
| 5,962,337 A | 10/1999 | Ohlmeyer |
| 6,004,942 A | 12/1999 | Firestein et al. |
| 6,074,859 A | 6/2000 | Hirokawa |
| 6,080,588 A | 6/2000 | Glick et al. |
| 6,100,254 A | 8/2000 | Budde et al. |
| 6,239,131 B1 | 5/2001 | Shinozaki |

(Continued)

FOREIGN PATENT DOCUMENTS

| CA | 2372150 | 11/2000 |
| CA | 2457405 | 2/2003 |

(Continued)

OTHER PUBLICATIONS

Bisaha, S.N., et al., A switch in enantiomer preference between mitochondrial F1F0-ATPase chemotypes, Bioorganic & Medicinal Chemistry Letters, 2005 15(11), pp. 2749-2751.
International Search Report and Written Opinion dated Mar. 27, 2009, PCT/US2008/076021.
Adachi, M., et al., "Aberrant Transcription Caused by the Insertion an Early Transposable Element . . .," PNAS. USA-90:1756-1760 (1993).
Adelman, N.E., et al., Treatment of (NZB X NZW)F1 Disease with Anti-I-A Monoclonal Antibodies; J. Exp. Med.-158:1350.1355 (1983).
Appleby, et al., "Murine chronic graft-versus-host disease as a model of osystemic lupus erythematosus: effect of immunosuppressive drugs on disease development," Clin. Exp. Immunol. (1989) 78, 449-453.

(Continued)

Primary Examiner — Bruck Kifle
(74) Attorney, Agent, or Firm — Fish & Richardson P.C.

(57) ABSTRACT

The present invention provides novel chemical compounds characterized as Rho kinase (ROCK) inhibitors, methods for their discovery, and their therapeutic, research, and diagnostic use. In particular, the present invention provides 1,4-benzodiazepine-2,5-dione compounds and related compounds having ROCK inhibitory activity, and methods of using such compounds as therapeutic agents to treat a number of conditions associated with ROCK activity.

20 Claims, No Drawings

(56) References Cited

U.S. PATENT DOCUMENTS

| | | | |
|---|---|---|---|
| 6,277,844 | B1 | 8/2001 | Spector et al. |
| 6,319,931 | B1 | 11/2001 | Kroemer et al. |
| 6,506,744 | B1 | 1/2003 | Alig |
| 6,524,623 | B1 | 2/2003 | Hodosh |
| 6,524,832 | B1 | 2/2003 | Kufe et al. |
| 6,579,854 | B1 | 6/2003 | Mitchell et al. |
| 6,605,593 | B1 | 8/2003 | Naicker |
| 6,613,739 | B1 | 9/2003 | Naicker |
| 6,767,533 | B1 | 7/2004 | Casellas |
| 6,824,561 | B2 | 11/2004 | Soykan et al. |
| 6,916,813 | B2 | 7/2005 | Atwal |
| 7,109,224 | B2 | 9/2006 | Kempson et al. |
| 7,125,866 | B1 | 10/2006 | Glick |
| 7,144,880 | B2 | 12/2006 | Glick |
| 7,150,433 | B2 | 12/2006 | Healy |
| 7,175,953 | B2 | 2/2007 | Licha |
| 7,220,739 | B2 | 5/2007 | Glick |
| 7,250,410 | B2 | 7/2007 | Bourguignon |
| 7,276,348 | B2 | 10/2007 | Glick |
| 7,351,421 | B2 | 4/2008 | Sung |
| 7,572,788 | B2 | 8/2009 | Glick |
| 7,638,624 | B2 | 12/2009 | Glick |
| 7,683,046 | B2 | 3/2010 | Glick |
| 7,851,465 | B2 | 12/2010 | Glick |
| 2002/0025946 | A1 | 2/2002 | Buchanan et al. |
| 2002/0048566 | A1 | 4/2002 | El-Deiry et al. |
| 2002/0128208 | A1 | 9/2002 | Snyder |
| 2003/0044776 | A1 | 3/2003 | Dykens et al. |
| 2003/0119029 | A1 | 6/2003 | Glick |
| 2004/0009972 | A1 | 1/2004 | Ding |
| 2004/0087489 | A1 | 5/2004 | Ruiz |
| 2004/0157833 | A1 | 8/2004 | Harris |
| 2004/0176358 | A1 | 9/2004 | Glick |
| 2004/0220180 | A1 | 11/2004 | Glick |
| 2005/0113460 | A1 | 5/2005 | Glick |
| 2005/0261176 | A1 | 11/2005 | Glick |
| 2005/0272723 | A1 | 12/2005 | Glick |
| 2006/0025388 | A1 | 2/2006 | Glick |
| 2006/0052369 | A1 | 3/2006 | Glick |
| 2006/0166975 | A1 | 7/2006 | Glick |
| 2007/0036854 | A1 | 2/2007 | Glick |
| 2007/0043033 | A1 | 2/2007 | Glick |
| 2007/0105844 | A1 | 5/2007 | Glick |
| 2007/0111994 | A1 | 5/2007 | Glick |
| 2007/0135418 | A1 | 6/2007 | Glick |
| 2007/0299059 | A1 | 12/2007 | Glick |
| 2008/0064686 | A1 | 3/2008 | Durrani |
| 2009/0275099 | A1 | 11/2009 | Glick |

FOREIGN PATENT DOCUMENTS

| | | |
|---|---|---|
| CA | 2457405 | 3/2003 |
| CA | 2524394 | 7/2011 |
| DE | 1810423 | 10/1969 |
| EP | 0227539 | 5/1990 |
| EP | 0 349 949 | 10/1990 |
| EP | 0 906 907 | 4/1999 |
| EP | 1143946 | 10/2001 |
| EP | 1423122 | 2/2003 |
| EP | 1398033 | 3/2004 |
| EP | 1622684 | 2/2006 |
| EP | 1742640 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 5/1990 |
| WO | 91/12779 | 9/1991 |
| WO | 9201683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 99/67220 | 12/1999 |
| WO | 00/19200 | 6/2000 |
| WO | 00/66106 | 11/2000 |
| WO | 01/51922 | 7/2001 |
| WO | 02/67988 | 9/2002 |
| WO | 02/098865 | 12/2002 |
| WO | 03/015703 | 2/2003 |
| WO | 03/041658 | 5/2003 |
| WO | 03/045901 | 6/2003 |
| WO | 03/050261 | 6/2003 |
| WO | WO 03/082841 | 10/2003 |
| WO | 03/106628 | 12/2003 |
| WO | 2004/050610 | 6/2004 |
| WO | 2005/004988 | 1/2005 |
| WO | 2006/007532 | 1/2006 |
| WO | 2006014526 | 2/2006 |
| WO | 2006/029245 | 3/2006 |
| WO | 2006002945 | 3/2006 |
| WO | 2006073448 | 7/2006 |
| WO | 2006074358 | 7/2006 |
| WO | 2007050587 | 5/2007 |
| WO | 2007053193 | 5/2007 |
| WO | 2007053725 | 5/2007 |
| WO | 2007146167 | 12/2007 |
| WO | 2008112553 | 9/2008 |
| WO | 2008116156 | 9/2008 |
| WO | 2008/133635 | 11/2008 |
| WO | 2009/036175 | 3/2009 |
| WO | 2009/061916 | 5/2009 |

OTHER PUBLICATIONS

Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).

Atwal, K.S., et al., "Small Molecule Mitochondrial F1F0 ATPase Huydrolase Inhibitors as Cardioprotective Agents" J. Med. Chem. 47, pp. 1081-1084 (2004).

Baader, S.L., et al., Uptake and Cytotoxicity of Ascorbic Acid and Dehydroascorbic Acid . . . Anticancer Research—14:221-228 (1994).

Bastian, et al., "Casein Interference in Bovine Plasmin Assays Using a Synthetic Substrate," (1991) J Dairy Sci 74:4119-4124.

Beale, P.J., et al., "BCL-2 Family Protein Expression and Platinum Drug Resistance in Ovarian Carcinoma," British Journal of Cancer—82 (2) :436-440 (2000).

Beurdeley-Thomas, et al., "The peripheral benzodiazepine receptors: a review," Journal of Neuro-Oncology 46 (2000) 45-56.

Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.

Blum, P., et al., "Stiff-Person Syndrome: An Autoimmune Disease," Movement Disorders 6(1):12-20 (1991).

Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.

Bono et al., "Peripheral benzodiazepine receptor agonists exhibit potent antiapoptotic activities," Biochemical and Biophysical Research Communications, 1999, 265, pp. 457-461.

Boojamra, C.G., et al., "Solid-Phase Synthesis of 1,4. Benzodiazepine-2,5-Diones. Library Prep. And Demonstration of Synthesis Generality," J. Org. Chem.-62:1240-1256 (1997).

Bunin et al., "Synthesis and evaluation of 1,4-benzodiazepine libraries", Methods in Enzymology, 1996, 267, pp. 448-465.

Bunin, B.A., et al. "The Combinatorial Synthesis and Chemical and Biological Evaluation of a 1,4-Benzodiazepine Libra ," PNAS USA-91:4708-4712 (1994).

Bunin, BA., et al., "A General and Expedient Method for the Solid-Phase Synthesis of 1,4-Benzodlazepine Derivatives," J. Am. Chem. Soc.-114:10997-10998 (1992).

(56) References Cited

OTHER PUBLICATIONS

Chumakov, A.M., et al., "Analysis of p53 Transactivation Through High-Affinity Binding Sites," Oncogene-8:3005o3011 (1993).
Churcher et al., "A new series of potent benzodiazepine y-Secretase inhibitors," Bioorganic & Medicinal Chemistry Letters 13 (2003) 179-.
Cohen, P.L., et al., "Lpr and gld: Single Gen•Models of Systemic Autoimmunity and Lymphoproliferative Disease,"Annu. Rev. Immunol. 9:243-269 (1991).
Cole et al., "The EBV-Hybridoma Technique and its Application to Human Lung Cancer", Monoclonal Antibodies and Cancer Therapy, Alan R. Liss, Inc., pp. 77-96 [1985].
Colosi, et al,"Mutational analysis of the intracellular domain of the human growth hormone recetor", J. Biol. Chem., 268:12617 [1993].
Crabtree, R.H., "A New Type of Hydrogen Bond," Science 282:2000-2001 1998.
Darrow et al., "Structurally similar small molecule photoaffinity CCK-A Agonists and Antagonists as Novel Tools . . .", Bioorganic & Medicinal Chemistry Letters 8 (1998) 3127-3132.
Desoize, B., "Anticancer Drug Resistance and Inhibition of Apoptosis," Anicancer Research—14:2291-2294 1994.
Dichek, David A., et al., "Seeding of intravascular stents with genetically engineered endothelial cells," Laboratory Investigation, 80:5 pp. 1347-1353 (1989).
Doble, A., et al., "Labelling of Peripheral-Type Benzodiazepine B Human Brain with [aH]I 1195:Anatomical and Subcellular Distribution," Brain Research Bulletin,18:49-61 1987.
Don, A. et al., Cancer Cell, vol. 3, May(2003) 497-509.
Donadio, J.V., et al., Immunosuppressive Drug Therapy in Lupus Nephritis, American Journal of Kidney Diseases 21 (3):239-250 1993.
EP Search, EP Patent Application No. 05856659.7, dated Dec. 9, 2008.
EP Search, EP Patent Application No. 04 775 923.8, dated Dec. 15, 2008.
Hulme, C. J. "Improved procedure for the solution phase preparation of 1,4-benzodiazepine-2,5-dione libraries . . .", Org. Chem., 63,(1998), 8021-8023.
Ermak, T.H., et al., "Treatment of Murine Lupus with Monoclonal Antibody to L3T4," Laboratory Investigation 61 (4):447-456 1989.
Fuh et al, "Rational design of potent antagonists to the human growth hormone receptor", Science, 256:1677 [1992].
Gallant, J.E., et al.,"Incidence and Natural History of Cytomegalovirus Disease in Patients with Advanced Human . . ." The Journal of Infect. Disease, 166: 1223-1227 (1992).
Garcia-Calvo, M., et al. "Inhibition of Human Caspases by Peptide-Based and Macromolecular Inhibitors," The Journal of Biological Chemistry 273(49):32608-32613 1998.
Gorczyca, W., et al., "Induction of DNA Strand Breaks Associated with Apoptosis During Treatment of Leukemias," Leukemia 7(5):659-670 1993.
Gordon, C., et al.. "Chronic Therapy with Recombinant Tumor Necrosis Factor-α in Autoimmune NZB/NZW Fi Mice," Clinical Immunology and Immunopatholoy, 52:421-434 (1989).
Gordon, E.M., et al., Applications of Combinatorial Technologies to Drug Discovery. 2. Combinatorial Organic 52 Synthesis, Library Screening . . . Journal of Med. Chem. 37(10): (1994).
Grasberger, Bruce L., "Discovery and cocrystal structure of benzodiazepinedione HDM2 antagonists that activate p53 in cells", J. Med. Chem., 48, (2005), 909-912.
Gupta et al., "Psychitripic drugs in dermatology . . ." Database:EMbase (AN:86111413), Journal of the American Academy of Dermatology, 1986, vol. 14, No. 4, pp. 633-645.
Hahn, B.H., et al.; "Influence of Cyclophosphamide and Other Immunosuppressive Drugs on Immune Disorders . . .," Arthritis and Rheumatism—18(2):145-152 (1975).
Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).

Hang, L., et al., "A Spontaneous Rheumatoid Arthritis-Like Disease in MR/1 Mice," J. Exp. Mod.—155:1690-1701 1982.
Herranz, R., "Cholesystokinin Antagonists: Pharmacological and Therapeutic Potential", Medicinal Research Reviews 23 (2003) 559-603.
Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).
Horowitz, R.E., et al., "Cyclophosphamide Treatment of Mouse Systemic Lupus Erythematosus," Laboratory Investigation 21 (3): 199-206 1969.
Huse et al., "Generation of a Large Combinatorial Library of the Immunoglobulin Repertoire in Phage Lambda", Science, 246:1275-1281 [1989].
International Search Report and Written Opinion of PCT/US2008/057827 dated Oct. 6, 2008.
IPER and ISR for PCT/us02/31942 mailed Feb. 2, 2007.
Itoh, N., et al., "The Polypeptide Encoded by the cDNA for Human Cell Surface Antigen Fas Can Mediate Apoptosis," Cell 66:233-243 (1991).
Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (WEB): Jun. 9, 2006.
Jones, The non-conalent interaction of pyrrolo[2,1-c][benzodiazepines-5, 11-diones with DNA, Anti-Cancer Drug Design, 5:249-264 (1990).
Kamal, A., "Synthesis of DNA-interactive Pyrrolo[2,1-c][1,4] benzodiazepines by employing polymer-supported reagents. . .," Synlett, 14,(2004), 2533-35.
Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.
Kerver et al, "In situ detection of spontaneous superoxide anion and singlet oxygen production by mitochondria in . . .", Histochem. J., 29:229-237 [1997] (Abstract only).
Kim et al., "Synthesis of 3-substituted 1,4-benzodiazepin-2-ones," J. Braz. Chem. Soc. 9:375-379 (1998).
Kohler and Milstein, "Continuous cultures of fused cells . . .", Nature, 256:495-497 [1975].
Koopman, W.J., et al., "The MRL-Ipr/Ipr Mouse. A Model for the Study of Rheumatoid Arthritis," Scan& J. Rheumatolo Suppl 75:284-0289 (1988).
Korsmeyer, S.J., "Bcl-2 Initiates a New Category of Oncogenes: Regulators of Cell Death," Blood 80(4):879-886 (1992).
Kozbor, et al. •"The production of monoclonal antibodies from human lymphocytes", Immunol. Today, 4:72 [1983].
Lee, Sunwoo et al., "Improved Catalysts for the Palladium-Catalyzed Synthesis of Oxindoles by . . .", J. Org. Chem. 2001, 66, pp. 3402-3415.
Lewis et al., "Editors' view: Cancer pharmacotherapy: 21st century 'magic bullets' and changing paradigms", British Journal of Clinical Pharmacology, 2006, 62:1,pp. 1-4.
Liu, J.R., et al., "Bclox•. is Expressed in Ovarian Carcinoma and Modulates Chemotherapy-induced Apoptosis," Gynecologic Oncology 70:398-403 (1998).
Los, M., et al., The Role of Caspases in Development, Immunity, and Apoptotic Signal Transduction: Immunity—10:629-639 (1999).
Lowman, et al., "Mutational analysis and protein engineering of receptor-binding determinants in human placental lactogen", J. Biol. Chem. 266:10982 [1991].
Luria,et al., "Tumor Viruses", General Viology 3rd edition,. 436-446 (1978)—Eds. John Wile & Sons, New York.
Malgrange, B., et al., "I•—Carbolines Induce Apoptotic Death of Cerebellar Granule Neurones in Cultures," NeuroReport 7(18):3041-3045 (1996).
Marino, M., et al., "Prevention of Systemic Lupus Erythematosus in MRL/Ipr Mice by Administration of an Immunoglobulin . . .," Nature Biotechnology—18:735-739 (2000).
McDonnell'—349:254-256T'J' et al., Progression from Lymphoid Hyperplasia to High-Grade . . . Nature-349:254-256 (1991).

(56) References Cited

OTHER PUBLICATIONS

MicColi, et al., "Potentiation of Lonidamine and Diazepam . . .", Journal of the National Cancer Institute, vol. 90, No. 18, pp. 1400-1406, Sep. 1998.
Miernik et al., "The antimitotic activities of some benzodiazepines", Experientia, 1986, 42, pp. 956-958.
Miller, K.A., et al., "Benzodiazepines Prevent Neuronal Death by Apoptosis & Necrosis . . .,"Society for Neuroscience Abstracts—24(1-2):979 (1998).
Monks, A., et., Feasibility of High-Flux Anticancer Drug Screen Using a Diverse Panel of Cultured Human Tumor Cell Lines, Journal of the National Cancer Institute, 83:757-766 (1991).
Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).
Okuyama, H., et al., "Analysis of Defective Delayed-Type Hypersensitivity in Autoimmune Mice Bearing Ipr Gene," Clln. Ex p. ImmunoL 63:87-94 1986.
Okuyama, H., et al., "Effect of Cyclophosphamide Pretreatment on Defective Delayed-Type Hypersensitivity . . . ," Int Arch. Allergy Appl. Immunol. 88:394-401 (1989).
Ozols, R.F., "Paclitaxel Plus Carboplatin in the Treatment of Ovarian Cancer," Seminars in Oncology 26(1) (Supp.2:84-89 (1999).
Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042.
Parks, Daniel J. "1,4-benzodiazepine-2,5-diones as small molecule antagonists of the HDM2-p53 interaction . . ." Bioorg Med Chem. Ltrs,. 15,(2005), 765-770.
Paull, K.D., et al., "Display and analysis of patterns of differential activity of drugs against human tumor . . .", J. Natl. Cancer Inst., 81:1088-1092 [1989] (Abstract only).
Pestell, K.E., et al., "Charactehsation of the P53 Status, BCL-2 Expression and Radiation and Platinum Drug Sensitivity of . . .," Int J. Cancer—77:913-918 (1998).
Giuseppe Piedimonte, et al., "Association of Tyrosine Protein Kinase Activity With Mitochondria in Human Fibroblasts," Journal of Cellular Biochemistry 32:113-123 (1986).
Raboisson, P. "Structure-based design, synthesis and biological evaluative of novel 1,4-diazepines as HDM2 antagonists," Bioorg Med Chem. Ltrs., 15,(2005), 1857-1861.
Ramdas et al., "Benzodiazepine compounds as inhibitors of the Src protein tyrosine kinase . . ." Archives of Biochemistry and Biophysics 368 (1999) 394-400.
Raynaud, F.I., et al., "Intracellular Metabolism of the Orally Active Platinum Drug JM216: Influence of Glutathione Levels," Br. J. Cancer 74(3) :380—?386 (1996).
Russell, J.H., et al., "Mature T Cells of Autoimmune Ipr/Ipr Mice have a Defect in Antigen-Stimulated Suicide,"Proc. Nat. Acad. Sci. USA 90:4409-4413 (1993).
Sakata, K., et al., "Role of FaslFasL Interaction in Physiology and Pathology: The Good and the Bad," Clinical Immunology and Immunopathology 87(1):1-7 (1998).
Sandstrom, P.A., et al., Autocrine Production of Extracellular Catalase Prevents Apoptosis.. Proc. Natl. Acad. Sci. USA—90:4708-4712 (1993).
Schlumpf, M., et al., "Delayed Developmental Immunotoxicity of Prenatal Benzodiazepines," Toxic. In Vitro—8 (5):1061-1065(1994).
Schoemaker, H., et al., "Specific High-Affinity Binding Sites for [3H]Ro5—4864 in Rat Brain and Kidney," The J. of Pharmacology and Experimental Therapeutics; vol. 225(1)61-69 (1983).
Schwab, M., et al., "Amplified DNA with Limited Homology to myc Cellular Oncogene is Shared by Human Neuroblastoma Cell Lines and . . . ," Nature—305:245-248 (1983).
Scott, C.F., et al., "Comparison of Antigen-Specific T Cell Responses in Autoimmune MRL/Mp-Ipr/Ipr and ML/Mp-+/+Mice," The Journal of Immunology, vol. 132, No. 2, pp. 633-639 (1984).
Sentman, C.L., et al., "bcl-2 Inhibits Multiple Forms of Apoptosis but not Negative Selection in Thymocytes," Cell 67:879-886 (1991).

Shaughnessy, Kevin, H., et al., "Palladium-Catalyzed Inter- and Intramolecular . . ." J. Org. Chem. 1998, 63, pp. 6546-6553.
Sheppard, R.C., et al., "Acid-Labile Resin Linkage Agents for Use in Solid Phase Peptide Synthesis;" Int J. Peptide Protein Res. 20:451-454 (1982).
Snyder, Jane R., et al, "Dissection of melanogenesis with small molecules identifies prohibition as a regulator", Chemistry & Biol. 12:477-484, 4(2005).
Shoemaker, Hans, et al., "Specific High-Affinity Binding Sites for [3H]Ro 5-4864 in Rat Brain and Kidney," The Journal of Pharmacology and Experimental Therapeutics, vol. 225, No. 1 (1983).
Tarpley, et al., J. Chroni Diseases (1965), 18 (abstract only).
Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.
Elz et al., 1989 Eur. J. Med Chem. 259-262.
Atwal et al., Tet Lett. 30, 1989, 7313.
Johnson, K.M., et al., Chemistry & Biology, 2005, 12:485-496.
Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.
Akssira, M., et al., "New Routes to 1,4-benzodiazepin-2,5-diones," Tetrahedron (1994), vol. 50, No. 30, pp. 9051-9060.
Mohiuddin, G., et al., "A Versatile Synthesis of 3H-1(H), 4(H)-Benzodiazepin-2,5-diones," Indian Journal of Chenmistry, 1985, vol. 24B, pp. 905-907.
Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.
Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.
Juaristi, Eusebio, et al., "Enantioselective Synthesis of α-Amino Acides from Chiral 1, 4-enzodiazepine-2, 5-diones Contianing the α-Phenethyl Group," Journal of Organic Chemistry, 1999, Mar. 26, vol. 64, No. 8, pp. 2914-2918.
Marc, Gasper, et al., "High Yield Phase Transfer N-Alkylation of Some Benzodiazepinese by Esters of ω-Halo Acids," Synthetic Communications, 1998, vol. 28, No. 7, pp. 1143-1157.
Bolli, M.H., et al., "Novel Benzo[1,4]diazepin-2-one-Derivatives as Endothelin Receptor Antagonists", Journal of Medicinal Chemistry, vol. 47, No. 11, Apr. 23, 2004, pp. 2776-2795.
Cunha, 2006, "The first bismuth(III)—catalyzed guanylation of thioureas", Tetrahedron Letters 47:6955-56.
Cunha, 2002, "Bismuth nitrate pentahydrate: a new and environmentally benign reagent for guanidylation of N-benzoylthioureas", Tetrahedron Letters 43: 49-52.
Yano, Masafumi, et al., "Effect of Milrinone on Left Ventricular Relaxation and Ca2+ Uptake Function of Cardiac Sarcoplasmic Reticulum," Am. J. Physiol. Heart Circ. Physiol, 279: H1898-H1905 (2000).
Gatza, et al., "Manipulating the Bioenergetics of Alloreactive T Cells Causes Their Selective Apoptosis and Arrests Graft-Versus-Host Disease," Sci. Transl. Med. 3(67ra8): 1-8 (2011).
Shoemaker, et al., "The NC160 Human Tumour Cell Line Anticancer Drug Screen", Nat. Rev. Cancer 6:813-823 (2006).
Brittain, H.G., Polymorphism in Pharmaceutical Solids (1999), published by Marcel Dekker, Inc. (New York, USA), Chapter 5, pp. 205-208.
Byrn, S.R., et al. Solid-State Chemistry of drugs. 2nd ed. (1999), published by SSCI, Inc. (Indiana, USA).
Boitano, Anthony, et al., "The Proapoptotic Benzodiazepine Bz-423 Affects the Growth and Survival of Malignant B Cells," Cancer Research 63, 6870-6876 (Oct. 15, 2003).
Munoz, et al., "Autoimmunity and chronic inflammation—two cleaance-related steps in the etiopathogenesis of SLE", Autoimmunity Reviews 10 (2010) pp. 38-42.
Database Registry (online), Chemical Abstracts Service, Columbus, Ohio, US; Aug. 13, 2001, retrieved from STN, Database Accession No. 351226-10-3.

(56) References Cited

OTHER PUBLICATIONS

Database Registry (online), Chemical Abstracts Service, Columbus, Ohio, US; Aug. 13, 2001, retrieved from STN, Database Accession No. 330829-66-8.
Database Registry (online), Chemical Abstracts Service, Columbus, Ohio, US; Apr. 11, 2001, retrieved from STN, Database accession No. 669724-32-7.
Kryl'Skii D V, et al., "Arylbiguanides in Heterocyclization Reactions", Russian Journal of General Chemistry, Nauka/Interperiodica, Mo, vol. 75, No. 2, Feb. 1, 2005, pp. 303-310.
EP Office Communication dated Dec. 7, 2012, related EP Patent Application No. EP 08 831 237.6.
Stevens, S.Y., et al., "Non Nucleic Acid Inhibitors of Protein-DNA Interactions Identified Through Combinatorial Chemistry," J. Am. Chem.Soc.—118:10650-10651 (1996).
Sugimoto, T., et al., Determination of Cell Surface Membrane Antigens . . . JNCI—73: (1):51-57 (1984).
Swanson et al, "Ligand recognition by anti-DNA Autoantibodies," Biochemistry, 35:1624-1633 [1996] (Abstract only).
Swanson, P.C., et al., "Ligand Recognition by Murine Anti-DNA Autoantibodies," J. Clin. Invest 97(7):1748-1760 (1996).
Swanson, P.C.,et al., "High Resolution Ephope Mapping of an Anti-DNA Autoantibody Using Model DNA Ligands," J. Immunology 71 152(5):2601-2612 (1994).
Takahashi, T., et al., "Generalized Lymphoproliferative Disease in Mice, Caused by a Point Mutation in the Fas Ligand;" Cell 76:969-976 (1994).
Tanimoto, Y., et al., Benzodiazepine Receptor Agonists Modulate Thymocyte Apoptosis Through Reduction of the Mitochondrial . . . Jpn. J. Pharmacol. 79:177-183 (1999).
Taupin, V., et al., Endogenous Anxiogenic peptide, ODN-Diazepam-Binding Inhibitor, and Benzodiazepines . . . Lymphokine and Cytoklne Research 10(1):7-13 (1991).
Theoffopoulous, AN, et al., "Murine Models of Systemic Lupus Erythematosus," Advances in Immunology 37:269-390 (1985).
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosis," Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G. Y., et al. "Receptor-Mediated in Vitro Gene Transformation by a Soluble DNA Carrier System," The Journal of Biological Chemistry 262(10):4429-4432 (1987).
Wyllie, A.H., "The Genetic Regulation of Apoptosis," Current Opinion in Genetics & Development 5:97-104 (1995).
Zamzami, N., et al., "Mitochondrial Control of Nuclear Apoptosis," J. Exp. Med. 183:1533-1544 1996.
Zoratti, M., et al., "The Mitochondrial Permeability Transition," Biochimica et Biophysica Acta 1241:139-176 (1995).
International Search Report, International Patent Application No. PCT/US02/26171 dated Aug. 8, 2003.
International Search Report, International Patent Application No. PCT/US01/11599 dated Mar. 6, 2001.
International Search Report, International Patent Application No. PCT/US05/031942 dated Sep. 21, 2006.
International Search Report, International Patent Application No. PCT/US04/013455 dated Jan. 6, 2006.
European Search Report, EP Patent Application No. 03 027 484.9-2117 dated May 3, 2004.

European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/US2006/042753, dated May 6, 2008.
Written Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.
International Report on Patentability, PCT/US2006/000442 mailed Jul. 12, 2007.
Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Examiners Report, AU Patent App. No. 2005323519 dated Nov. 27, 2007.
EP Search, EP Patent App. No. 03 027 484.9-2117, dated Jan. 31, 2005.
Nawrocka, et al., Arch. Pharm. (Weinheim) Jan. 2001, 334(1), 3-10.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.
Godic, "New approaches to psoriasis treatment. A review." 2004, Acta Dermatoven APA, vol. 13, No. 2, pp. 50-57.
International Search Report, PCT/US06/042753, mailed Apr. 19, 2007.
Desjardins, P and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
AU Patent Application No. 2006203946 Examiner's Report dated Sep. 10, 2008.
Iiangumaran, et al., "CD44 Selectively Associates with Active Src Family Protein Tyrosine Kinases Lck and Lyn in Glycosphingolipid-Rich . . .", Blood, vol. 91, No. 10 (May 15, 1998), pp. 3901-3908.
Sato, et al., "CD22 negatively and positively regulates signal transduction through the B lymphocyte antigen receptor," seminars in Immunology, vol. 10, 1998, pp. 287-297.
Joshi, et al., "Oligomycin Sensitivey-conferring Protein (OSCP) of Mitochodrial ATP Synthase," The Journal of Biological Chemistry, vol. 267, No. 18,m Issue of Jun. 25, pp. 12860-12867, 1992.
EP Supplementary Search Report, EP Application No. 02794914.8 dated Nov. 6, 2008.
Lee, et al., J. Org. Chem. 1999, 64, 3060-3065.
Solomko, et al., Chemistry of Heterocyclic Compounds, vol. 11, No. 11, Nov. 1975, pp. 1231-1248.
Algarra, et al., "Application of the Photo-Fries Rearrangement of Aryl N-Chloroacetylanthranylates as Key Step in the . . .", Heterocycles, vol. 36 1993, pp. 2335-2344.
EP Patent Application No. 06 717616 Supplementary Search Report dated Mar. 26, 2009.
Levitzki, Alexander, "Protein Tyrosine Kinase Inhibitors as Novel Therapeutic Agents," Pharmacol. Ther. vol. 82, Nos. 2-3, pp. 231-239 (1999).
Sanchez, et al., "Tumorigenic activity of the BCR-ABL oncogenes is mediated by BCL2" Proc Natl Acad Sci U S A (Jun. 6, 1995) 92(12) 5287-5291.
Ji Yang, et al., "Prevention of Apoptosis by BCL-2; Release of Cytochrome c from Mitochondria Blocked" Science 275, 1129 (1997).
Prindull, "Apoptosis in the embryo and tumorigenesis" European Journal of Cancer, vol. 31, Issue 1 (1995) pp. 116-123.

(56) References Cited

OTHER PUBLICATIONS

Chinese Office Action, CN Patent Application No. 200580029827.4, dated Apr. 17, 2009.
Lowe, "Systemic treatment of severe psoriasis," The New England Journal of Medicine, 324 (5), Feb. 7, 1991, pp. 333-334.
Laupacis, et al., "Cyclosporin A: a powerful immunosuppressant", CMA Journal, May 1, 1982, vol. 126, pp. 1041-1046.
Otto, Michael W., Ph.D., et al., "Benzodiazepine Use, Cognitive Impairment, and Cognitive-Behavioral Therapy for Anxiety Disorders: Issues in the Treatment of a Patient in Need," J. Clin. Psychiatry, 2005, 66 (supp 2).
Yoshi, M., et al., (2005) Nippon Yakurigaku Zasshi 125(1):33-36 (English Abstract attached).
Yasuda, K., (2004) Nippon Rinsho. 62 Suppl. 12:360-363. Abstract not available.
Decaudin, Didier, "Peripheral benzodiazepine receptor and its clinical targeting," Anti-Cancer Drugs, 2004, vol. 15, No. 8.
Bonnot, O., et al., "Exposition in utero au lorazepam et atresie anale: signal epidemiologique," (2003) Encephale. 29 (6):553-559.
Lacapere, Jean-Jacques, Vassilios Papadopoulos, "Peripheral-type benzodiazepine receptor: structure and function of a cholesterol-binding protein in steroid and bile acid biosynthesis," Steroids, 68 (2003) 569-585.
Galiegue, S., et al., "The Peripheral Benzodiazepine Receptor: A Promising Therapeutic Drug Target," (2003) Curr. Med. Chem (10(16):1563-1572.
Papadopoulo, V. (2003), Lecture: Peripheral benzodiazepine receptor: structure and function in health and disease, Ann. Pharm. Fr. 61(1):30-50.
Goethals, Ingeborg, et al., "Is central benzodiazepine receptor imaging useful for the identification of epileptogenic foci in localization-related epilepsies?" European Journal of Nuclear Medicine and Molecular Imaging vol. 30, No. 2, Feb. 2003.
Castedo, Marian, et al., "Mitochondrial Apoptosis and the Peripheral Benzodiazepine Receptor: a Novel Target for Viral and Pharmacological Manipulation," The Journal of Experimental Medicine, vol. 196, No. 9, Nov. 4, 2002.
Buffett-Jerrott S.E. et al., "Cognitive and Sedative Effects of Benzodiazepine Use," Current Pharmaceutical Design, 2002, 8, 45-48.
Smyth, W.F., et al. (1998), "A critical evaluation of the application of capillary electrophoresis to the detection and determination of 1,4-benzodiazepine tranquilizers in formulations and body materials," Electrophoresis 19 (16-17):2870-2882.
Yoshii, M., et al. (1998) Nihon Shinkeo Seishin Yakurigaku Zasshi, 18(2):49-54.
Varani, et al., (1994), "All-trans Retinoic Acid (RA) Stimulates Events in Organ-cultured Human Skin that Underlie Repair," J. Clin. Invest., 94:1747-1753.
Griffith, C.E., "Editorial Comment: Ascomycin: an advance in the management of atopic dermatitis," Br. J. Dermatol., 2001, April; 144(4):679-81.
Stern, R.S. (1995), "Epidemiology of Psoriasis," Dermatologic Clinics, 13:717-722.
Fry, L (1988), "Psoriasis," Brit. J. Dermatol., 119:445-461.
Krueger GC, et al., (1984), "Psoriasis," J. Am. Acad. Dermatol., 11:937-947.
Varani, J., et al. (2001), "Heparin-Binding Epidermal-Growth-Factor-Like Growth Factor Activation of Keratinocyte ErbB . . .", J. Invest. Dermatol., 117:1335-1341.
Varani, J., et al., "A Novel Benzodiazepine Selectively Inhibits Keratinocyte Proliferation . . .", The Journal of Pharmacology and Experimental Therapeutics, 2005, vol. 313, No. 1, pp. 56-63.
International Search Report and Written Opinion, PCT/US2008/082629, mailed Jun. 1, 2009.

Bhagavathula, Narasimharao, et al., "7-Chloro-t-(4-hydroxyphenyl_-1-methyl-3-(naphthalen-2-ylmethyl) . . .", J. Pharmacol & Exp Ther 324: 938-947 (2008).
Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.
Mahrle, et al., Br. J. Bermatol. 1974, 91, 529-540.
Mui et al. Br. J. Dermatol. 1975, 92, 255-262.
EP Search Report dated Nov. 26, 2009, EP Patent Application No. 09003224.4.
Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.
Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.
Bossu, et al., "IL-18 cDNA vaccination protects mice from spontaneous lupus-like autoimmune disease," PNAS 2003, 100: 14181-14186.
De Bandt, et al., "Systemic lupus erythematosus induced by anti-tumour necrosis factor alpha therapy: a French national survey," Arthritis Res. & Ther., 2005, 7: R545-R551.
Abunasser, et al., "Etanercept-Induced Lupus Erythematosus Presenting as a Unilateral Pleural Effusion," Chest 2008, 134: 850-853.
Busca, et al., "Recombinant human soluble tumor necrosis factor receptor fusion protein as treatment for steroid refractory graft-versus-host disease following allogeneic hematopoietic stem cell transplatation," Am. J. Hematol., 2007, 82: 45-52.
Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).
Kluge, et al., "Kinetics of Inactivation of the F1F0 ATPase of Propionigenium modestum by Dicyclohexylcarbodiimide in Relationship to H+ and Na+ Concentration: Probing the Binding Site for the Coupling Ions," Biochemistry 1993, 32, 10378-10386.
Covelli, Vito, "Stress, Neuropsychiatric Disorders and Immunological Effects Exerted by Benzodiazepines," Immunopharmacology and Immunotoxicology, 20(2), 199-209 (1998).
EP Search Report dated Jun. 23, 2010, EP Patent Application No. 10 003 823.1.
EP Search Report dated Aug. 10, 2010, EP Patent Application No. 08731682.4.
Office Action Mailed Apr. 3, 2009, U.S. Appl. No. 11/176,719, filed Jul. 6, 2005.
Office Action Mailed Aug. 19, 2009, U.S. Appl. No. 11/176,719, filed Jul. 6, 2005.
Office Action Mailed May 24, 2010, U.S. Appl. No. 11/176,719, filed Jul. 6, 2005.
International Preliminary Report on Patentability in International Application No. PCT/US2010/055255, issued May 22, 2012, 5 pages.
International Search Report and Written Opinion in International Application No. PCT/US2010/055255, dated Aug. 2, 2011, 9 pages.
Supplementary European Search Report in EP Application No. 10831982.3 dated Apr. 8, 2013, 10 pages.
Dong et al., "Rho-kinase inhibition: a novel therapeutic target for the treatment of cardiovascular diseases," Drug Discovery Today, Aug. 2010, 15(15/16):622-629.
LoGrasso and Feng, "Rho Kinase (ROCK) Inhibitors and Their Application to Inflammatory Disorders," Curr Topics Med. Chem., 2009, 9:704-723.
Pan et al., "Advances in the development of Rho-associated protein kinase (ROCK) inhibitors," Drug Discovery Today, Dec. 2013, 18(23/24):1323-1333.
Schaafsma et al., "Rho kinase inhibitors: A novel therapeutical intervention in asthma?," EP J Pharm., 2008, 585:398-406.

1,4-BENZODIAZEPINE-2,5-DIONES AND RELATED COMPOUNDS WITH THERAPEUTIC PROPERTIES

CROSS-REFERENCE TO RELATED APPLICATION

The present application is a U.S. 371 National Phase Entry of International Patent Application No. PCT/US2010/055255, international filing date Nov. 3, 2010, which claims priority to expired U.S. Provisional Patent Application No. 61/262,017, filed Nov. 17, 2009, the contents of which are hereby incorporated by reference in their entireties.

STATEMENT REGARDING FEDERALLY SPONSORED RESEARCH OR DEVELOPMENT

None.

FIELD OF THE INVENTION

The present invention provides novel chemical compounds characterized as selective Rho kinase (ROCK) inhibitors, methods for their discovery, and their therapeutic, research, and diagnostic use. In particular, the present invention provides 1,4-benzodiazepine-2,5-dione compounds and related compounds having selective ROCK inhibitory activity, and methods of using such compounds as therapeutic agents to treat a number of conditions associated with ROCK activity.

BACKGROUND OF THE INVENTION

Following the discovery of Ras in 1981, a number of related small GTP-binding proteins (small GTPases) have been identified and their physiological functions have been extensively studied. These small GTPases (molecular mass 20-30 kDa) switch between the inactive GDP-bound state and the active GTP-bound state, a process that is highly regulated primarily by guanine exchange factors (GEFs) and GTPase activating proteins (GAPs) (see, e.g., Hall, A., Science (1990) 249:635-640; Bourne, H. R. et al., Nature (1991) 349:117-127; each of which are herein incorporated by reference in their entireties).

To date, more than 50 different genes encoding small GTPases have been identified from yeast to mammals, forming the Ras superfamily. These small GTPases are largely divided into 5 families of Ras, Rho, Rab, Arf, and Ran, according to primary amino acid sequences and functional similarities. Of these, Rho, (Ras homologue) encodes a polypeptide having about 35% homology with Ras (see, e.g., Madaule, P., Cell (1985) 41:31-40; herein incorporated by reference in its entirety). The Rho family itself can be divided into 6 subfamilies based on primary amino acid sequence, structural motifs, and biological function, which includes the RhoA-related subfamily, Cdc42-related subfamily, Rac-related subfamily as well as the Rnd, RhoBTB and Miro subfamilies. Cellular activity of Rho has been studied by several methods including overexpression or microinjection of the active GTP-bound form of Rho to identify the phenotype of Rho activation. A second complimentary method has been to treat cells with botulinum C3 exoenzyme, which specifically ADP-ribosylates and inactivates endogenous Rho thereby identifying the phenotype of Rho inactivation (Narumiya, S. J Biochem (1996) 120:215-228). As such, Rho GTPases have been identified as key regulators of actin reorganization and have been implicated in the regulation of cell polarity, migration, cell shape, adhesion, contraction, as well as endo- and exocytosis (see e.g., Ridley, A. J., Trends Cell Biol (2001) 11:471-477).

Downstream targets of Rho GTPases that are involved in actin cytoskeletal reorganization include citron kinase, p140mDia, protein kinase N (PKN), p21-activated protein kinase (PAK), rhophillen, and rhotekin. The Rho-associated coiled-coil-forming protein kinases (ROCKs), first isolated by T. Ishizaki and coworkers in the mid-1990s, were the first and best characterized effectors of RhoA and were initially characterized for their roles in mediating the formation of RhoA-induced stress fibers and focal adhesion through their effects on the phosphorylation of myosin light chain (Matsui, T., et. al., EMBO J. (1996) 15:2208-2216; Leung, T., et. al., Mol. Cell. Biol. (1996) 16:5315-5327). Subsequently, ROCKs have been shown to play a role in many key cellular functions such as cell motility, invasion, contraction, differentiation, migration, and survival (Riento, K., Ridley, A., Nature Rev. Mol. Cell. Biol. (2003) 4:446-456).

ROCKs are serine/threonine protein kinases with a molecular mass of approximately 160 kDa. Two isoforms encoded by two different genes have been identified: ROCKI (also known as ROKβ or p160ROCK) and ROCKII (or ROKα). The isoforms share an overall amino acid sequence identity of 65% and 92% sequence identity in their kinase domains. ROCKs are most homologous to members of the AGC kinases such as myotonic dystrophy kinase (DMPK), DMPK-related cell division control protein 42 (Cdc42)-binding kinase (MRCK), and citron kinase (CK). In general, this family of kinases consists of an amino-terminal kinase domain followed by a coiled-coil-forming region and then a pleckstrin-homology (PH) domain with an internal cysteine-rich repeat at the carboxy-terminal. In addition, ROCKs also contain a Rho-binding domain (RBD) within their coiled-coil domain. In the inactive state, the carboxy-terminal domains bind to the amino-terminal region, which forms an autoinhibitory loop. Activated, GTP-bound Rho binds to the RBD of ROCK, which results in an open conformation of the kinase thereby freeing the catalytic activity. ROCKs can also be activated by lipid binding (e.g., arachidonic acid and sphingosylphosphorylcholine) to the PH domain. ROCK activity can also be induced during apoptosis as caspase 3 can cleave the auto-inhibitory loop of ROCKI while granzyme B and caspase 2 cleave ROCKII in a similar fashion, both of which result in constitutively active ROCK.

In response to activators of Rho, such as lysophosphatidic acid (LPA) or sphingisone-1 phosphate (S1P), which stimulate Rho GEFs and lead to the formation of active GTP-bound Rho, ROCKs mediate a broad range of cellular responses involving the actin cytoskeleton through phosphorylation of a variety of cellular targets. For example, phosphorylation of the motor protein myosin II has an important role in regulating actomyosin contractility. ROCK can directly phosphorylate myosin light chain (MLC), which results in subsequent myosin-actin interactions and enhanced cell contractility. ROCK can also indirectly regulate MLC phosphorylation levels through phosphorylation (and inactivation) of myosin light chain phosphatase (MLCP). Another downstream target of ROCK are LIM kinases 1 and 2, whose phosphorylation leads to inhibition of cofilin-mediated actin-filament disassembly and therefore an increase in the number of actin filaments. Other cellular targets of ROCK include the ezrin/radixin/moesin (ERM) protein complex, intermediate filament proteins such as vimentin, and the filamentous (F)-actin-binding protein adducin (Riento, K., Ridley, A., Nature Rev. Mol. Cell. Biol. (2003) 4:446-456).

Despite having similar kinase domains, ROCK1 and ROCK2 may have different cellular functions and have different downstream targets. For example, in vitro ROCK1 has been shown to phosphorylate LIM kinase 1 and 2, while ROCK 2 phosphorylates MLC, adducin, smooth muscle-specific basic calponin, and collapsing response mediator protein-2 (CRMP2), a neuronal protein that is involved in LPA-induced collapse of growth cones (Riento, K., Ridley, A., Nature Rev. Mol. Cell. Biol. (2003) 4:446-456). Furthermore, siRNA experiments have demonstrated distinct roles for ROCK1 and ROCK2 in rat embryonic fibroblast cells where ROCK1 was important for stress fiber formation and stabilization of focal adhesion sites, while ROCK2 activity was involved in phagocytosis of matrix-coated beads (Yoneda, A., et. al., J. Cell Biol. (2005) 170:443-453). Differential expression and regulation in various cell types has also been observed. For example, only ROCK1 is cleaved by caspase 3 during apoptosis while ROCK2 is cleaved by granzyme B and caspase 2. In addition, ROCK1 expression tends to be more ubiquitous, while ROCK2 is most highly expressed in muscle and brain tissues indicating that the protein may have a specialized role in these cell types (Nakagawa, O., et. al., FEBS Lett. (1996) 392:189-193). However, in vivo data relating ROCK1 and ROCK2 isoforms to differential functions is still lacking.

Abnormal activation of the Rho/ROCK pathway has been shown to play a role in a wide range of diseases, both in those involving abnormal smooth muscle tone or smooth muscle hyperreactivity as well as in pathological processes involving non-smooth muscle cells. For example, Rho/ROCK mediated-signaling has been shown to be involved in the pathogenesis of hypertension, vasospasms leading to vasoconstriction and ischemia (both cerebral and coronary), bronchial asthma, preterm labor, erectile dysfunction, and glaucoma (Werrschureck, N., Offermanns, S., J Mol. Med. (2002) 80:629-638 and references therein). Vascular diseases such as hypertension, atherosclerosis, postangioplasty restenosis, and transplant arteriosclerosis, which are characterized by abnormal vascular smooth muscle cell (VSMC) proliferation and migration have also been shown to be associated with increased Rho/ROCK signaling. Rho/ROCK mediated signaling is also associated with disease in non-smooth cells such as myocardial hypertrophy. Abnormal activation of the Rho/ROCK pathway has been observed in various disorders of the central nervous system (CNS; Mueller, B. K. et al., Nature Rev. Drug Discovery (2005) 4:387-398 and references therein). Injury to the adult vertebrate brain and spinal cord activates ROCKs, thereby inhibiting neurite growth and sprouting. As such, there is significant potential therapeutic use of ROCK inhibitors for the treatment of various neurological disorders, including spinal-cord injury, Alzheimer's disease, stroke, multiple sclerosis, and neuropathic pain. Furthermore, tumor cell migration and invasion involves Rho-mediated processes and activation of RhoA or of ROCK has been shown to increase the invasiveness of cultured rat hepatoma cells (Itoh, K., et al., Nat. Med. (1999) 5:221-225). In addition, a number of oncogenes encode exchange factors for Rho suggesting that the Rho/ROCK pathway is an attractive candidate for new anticancer strategies.

Given the extensive involvement of the Rho/ROCK pathway in many disease states, there has been considerable interest in the development of ROCK inhibitors in the last 20+ years. Fasudil

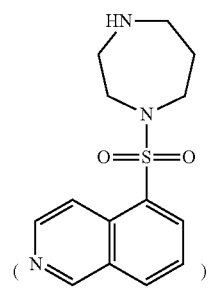

and Y-27632

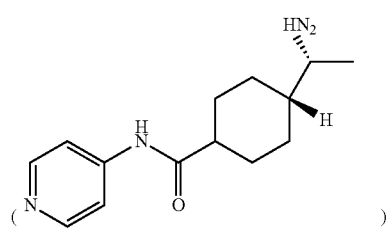

were the first small-molecule ROCK inhibitors discovered (Uehata, M. et al. Nature (1997) 389:990-994). Subsequently, many more inhibitors have been developed and can be generally grouped into four classes according to their hinge-binding scaffold: isoquinolines (e.g, fasudil), 4-aminopyridines (e.g., Y-27632), indazoles, and amide and urea derivatives. ROCK inhibitors reported to date act by competitive interaction at the ATP binding site. However, due to the high sequence homology between ATP-binding sites, the development of inhibitors specific for ROCK has been challenging. Although few results have been reported for ROCK inhibitors in general, data reported for Y-27632 and fasudil demonstrate some cross-reactivity of these inhibitors against other kinases. For example, Y-27632 showed selectivity against 21 of 25 kinases tested but inhibited protein kinase N (PKN or PRK2) with equal potency and was only 10-50-fold selective over mitogen- and stress-induced kinase 1 (MSK1), mitogen-activated protein kinase-activated protein kinase 1b (MAPKAPK1b), citron kinase, and phosphorylase kinase (PHK) (Davies, S. P., et al. Biochem J (2000) 351:95-105). In the same study, fasudil was shown to be less selective that Y-27632 showing selectivity against only 19 of the 27 kinases tested. Furthermore, Y-27632 and fasudil (similar to other reported ROCK inhibitors) do not demonstrate any ROCK isoform selectivity with almost identical inhibition of ROCK1 and ROCK2. Although animal studies involving ROCK1 and ROCK2 knock-out mice suggest distinct physiological roles for the two ROCK isoforms, data is still lacking. However, currently available ROCK inhibitors cannot be used to differentiate the role of ROCK1 versus ROCK2 either in cellular signaling or substrate recognition, or more importantly, in the specific role of each isoform in disease.

Fasudil has been marketed in Japan since 1995 for the treatment of vasospasm after subarachnoid hemorrage and safety profile data indicate that it is well tolerated in humans. It has been shown to have beneficial effects in a number of cardiovascular diseases including angina pectoris, hypertension, coronary vasospasm, restenosis after percuteneous coronary intervention, and arteriosclerosis (Hirooka, Y., Shimokawa, H., Am. J. Cardiovasc. Drugs (2005) 5:31-39 and references therein). Y-27632 has been much less investigated in vivo but limited studies have demonstrated that (similar to fasudil) it is rapidly metabolized and brain penetration may be too low to achieve therapeutic levels for CNS diseases. In addition, both inhibitors, like other ATP-competitive inhibitors, demonstrate a 100-1.000-fold decrease in activity in cellular assays, as compared to in vitro activities due to competition with intracellular micromolar ATP concentrations. At such a high cellular concentration, their low-to-moderate kinase selectivity for PKN, citron kinase, MSK1, and MAPKAPK1b can lead to additional off-target effects. As such, the development of a new structural class of ROCK inhibitors may provide more selective ROCK inhibitors against other kinases as well as the development of ROCK isoform-specific inhibitors. Such inhibitors have the potential to be used therapeutically in both cancer and heart disease given the evidence from animal studies of the involvement of ROCK in invasion, metastasis, neuroregeneration, and smooth muscle-cell contraction.

What are needed are improved compositions and methods for inhibiting Rho kinase activity in subjects afflicted with diseases and conditions associated with aberrant Rho kinase activity.

SUMMARY

Rho-Kinase (ROCK) is a member of the serine-threonine protein kinase family. ROCK exists in two isoforms, ROCK1 and ROCK2 (see, e.g., T. Ishizaki et al., EMBO J., 1996, 15, 1885-1893; herein incorporated by reference in its entirety). The present invention provides novel chemical compounds characterized as selective ROCK inhibitors (e.g., inhibitors of ROCK1 and/or ROCK2), methods for their discovery, and their therapeutic, research, and diagnostic use. In particular, the present invention provides 1,4-benzodiazepine-2,5-dione compounds and related compounds having selective ROCK inhibitory activity, and methods of using such compounds as therapeutic agents to treat a number of conditions associated with ROCK activity. Such compounds and uses are described throughout the present application and represent a diverse collection of compositions and applications. Certain preferred compositions and uses are described below. The present invention is not limited to these particular compositions and uses. The present invention provides a number of useful compositions as described throughout the present application.

In certain embodiments, the present invention provides compounds having selective ROCK inhibitory activity. The present invention is not limited to a particular type or kind of selective ROCK inhibitor. Experiments conducted during the course of developing embodiments for the present invention identified compounds capable of inhibiting ROCK activity (e.g., inhibiting ROCK1 and/or ROCK2 activity). In addition, experiments conducted during the course of developing embodiments for the present invention identified compounds as selective ROCK inhibitors (e.g., compounds that selectively inhibit ROCK1 activity over ROCK2 activity) (e.g., compounds that selectively inhibit ROCK2 activity over ROCK1 activity).

While not limited to the particular compounds, the present invention provides ROCK activity inhibiting compounds described by a formula selected from the group consisting of:

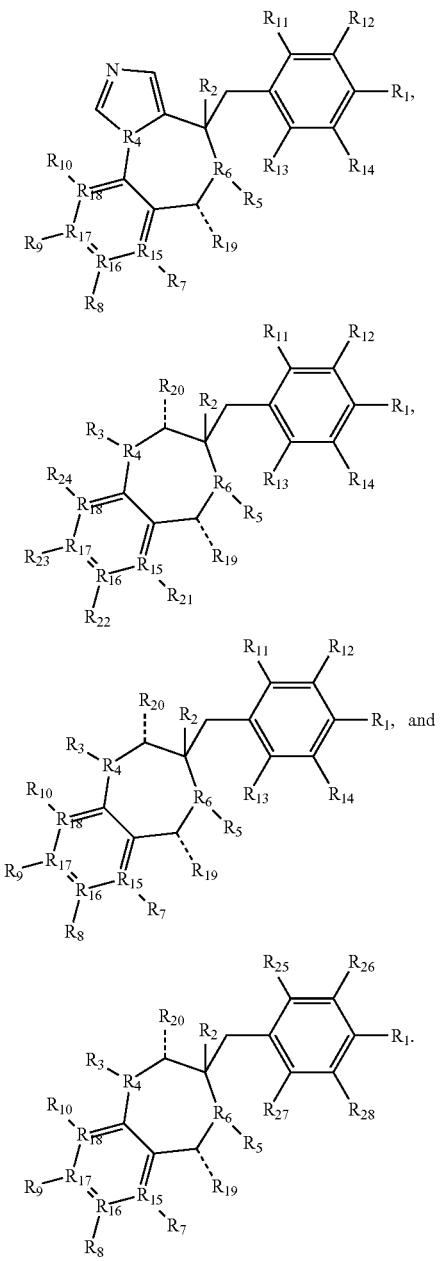

In some embodiments, R1 is a chemical group comprising at least two carbon molecules. In some embodiments, R1 is not pyridine.

In some embodiments, R1 is selected from the group consisting of: hydrogen, alkyl, substituted alkyl,

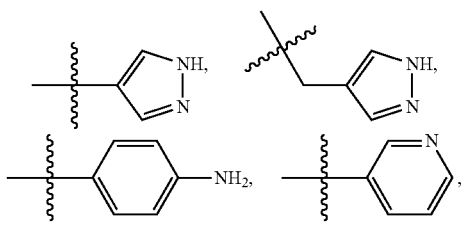

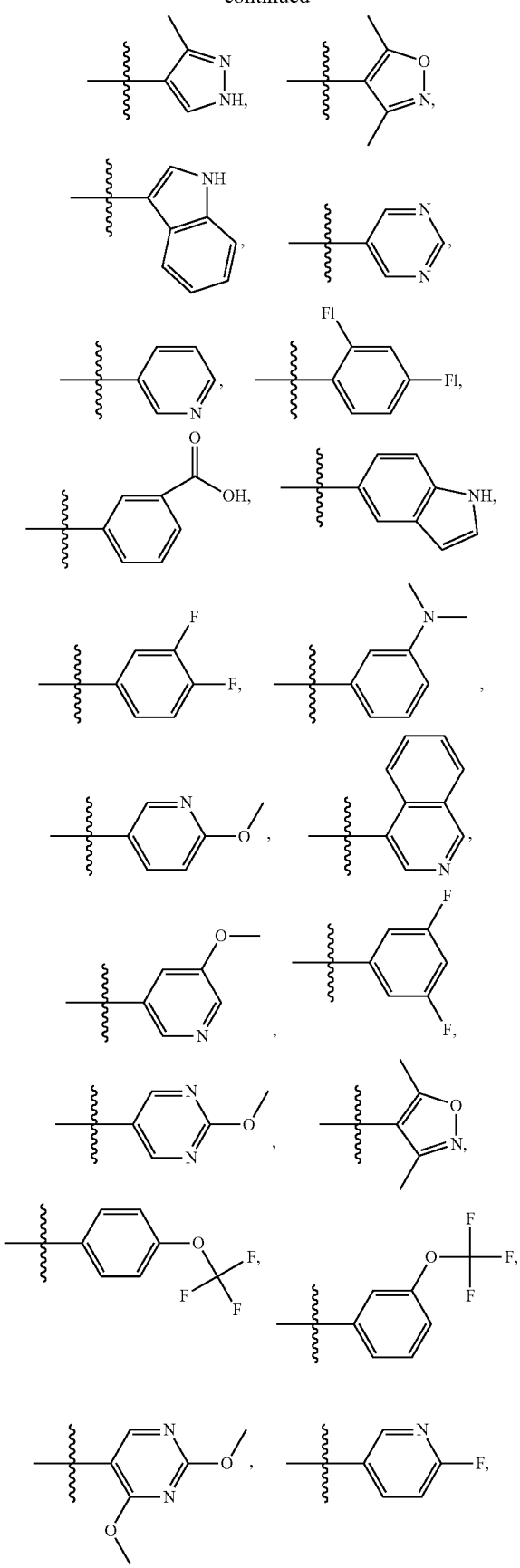
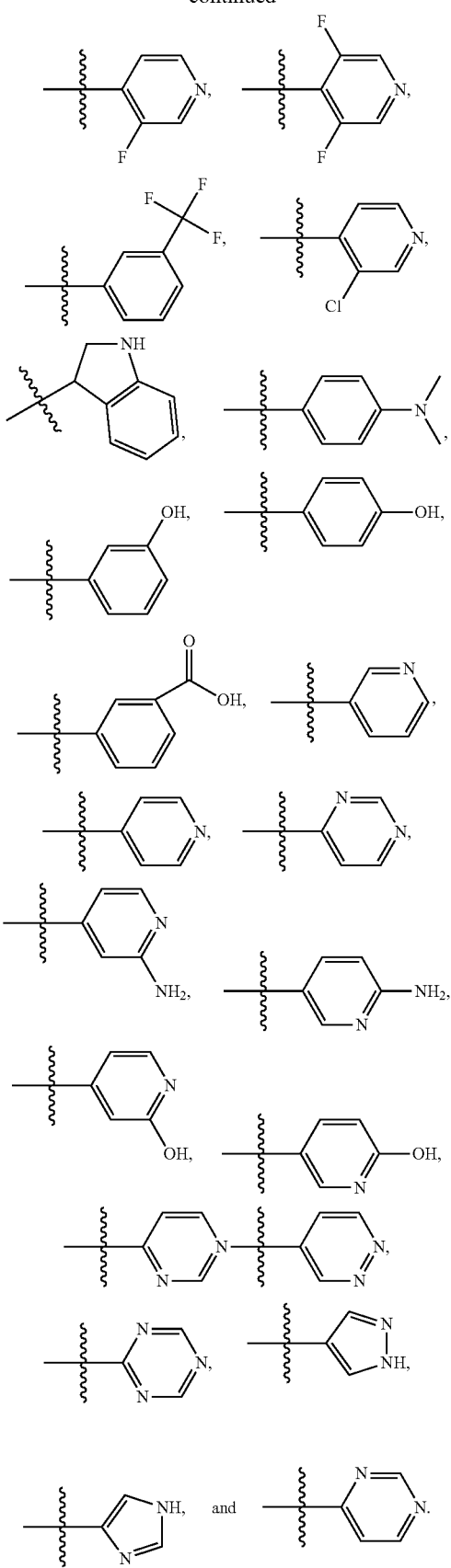

In some embodiments, R1' is selected from the group consisting of

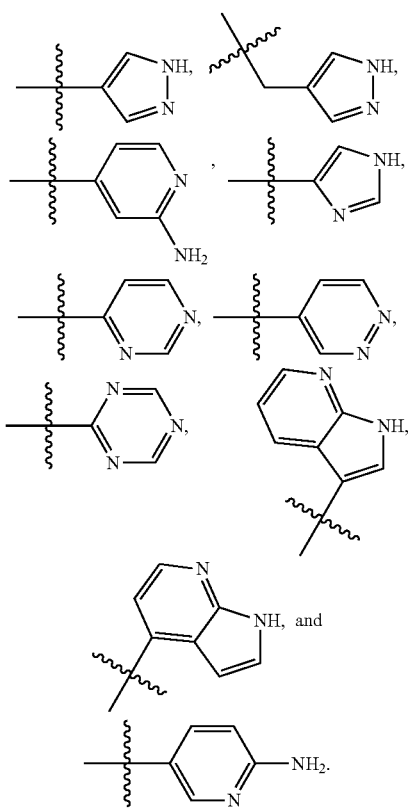

In some embodiments, $R_2$ is selected from the group consisting of H, alkyl, substituted alkyl, and $R_1$.

In some embodiments, $R_3$ is selected from the group consisting of H, alkyl (e.g., methyl, ethyl, hexyl, isopropyl), and substituted alkyl.

In some embodiments, R3 is selected from the group consisting of hydrogen; H; $CH_3$; ethyl; hexyl; isopropyl; halogen (e.g., fluorine, chlorine, bromine, iodine, astatine); OH; a chemical moiety comprising an aryl subgroup; a chemical moiety comprising a substituted aryl subgroup; a chemical moiety comprising a cycloaliphatic subgroup; a chemical moiety comprising a substituted cycloaliphatic subgroup; a chemical moiety comprising a heterocyclic subgroup; a chemical moiety comprising a substituted heterocyclic subgroup; a chemical moiety comprising at least one ester subgroup; a chemical moiety comprising at least one ether subgroup; a linear or branched, saturated or unsaturated, substituted or non-substituted, aliphatic chain having at least 2 carbons; a chemical moiety comprising Sulfur; a chemical moiety comprising Nitrogen; —OR—, wherein R is selected from the group consisting of a chemical moiety comprising an aryl subgroup; a chemical moiety comprising a substituted aryl subgroup; a chemical moiety comprising a cycloaliphatic subgroup; a chemical moiety comprising a substituted cycloaliphatic subgroup; a chemical moiety comprising a heterocyclic subgroup; a chemical moiety comprising a substituted heterocyclic subgroup; a linear or branched, saturated or unsaturated, substituted or non-substituted, aliphatic chain having at least 2 carbons; a chemical moiety comprising at least one ester subgroup; a chemical moiety comprising at least one ether subgroup; a chemical moiety comprising Sulfur; a chemical moiety comprising Nitrogen.

In some embodiments, the R1 and R3 groups may be interchanged (e.g., in some embodiments, the R1 group is positioned at the first position of the benzodiazepine ring and the R3 group is positioned at the third position of the benzodiazepine ring; in some embodiments, the R1 group is positioned at the third position of the benzodiazepine ring and the R3 group is positioned at the first position of the benzodiazepine ring).

In some embodiments, R4 is selected from the group consisting of C, N, S and O.

In some embodiments, R5 is selected from the group consisting of H, alkyl, substituted alkyl, mono-substituted aryl, di-substituted aryl, and tri-substituted aryl.

In some embodiments, R6 is selected from the group consisting of C, N, S and O.

In some embodiments, R7, R8, R9, and R10 are independently selected from the group consisting of being absent, H, halogen, CF3,

(e.g., substituted alkyl) (e.g., unsubstituted alkyl),

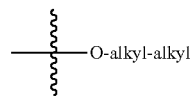

(e.g., substituted alkyl) (e.g., unsubstituted alkyl), OH, fluoroalkyl, sulfonamide, sulfone, $OCH_3$, $CH_3$, $SO_2R_{28}$, $SO_2N(R_{7'})_2$, $OR_{7'}$, $N(R_{7'})_2$, $CON(R_{7'})_2$, $NHCOR_{7'}$, $NHSO_2R_{7'}$, alkyl, mono-substituted alkyl, di-substituted alkyl, tri-substituted alkyl; wherein $R_{7'}$ is selected from the group consisting of halogen, H, alkyl, mono-substituted alkyl, di-substituted alkyl, tri-substituted alkyl, aryl, mono-substituted aryl, di-substituted aryl, tri-substituted aryl, cycloaliphatic, mono-substituted cycloaliphatic, di-substituted cycloaliphatic, and tri-substituted cycloaliphatic.

In some embodiments, R11, R12, R13, and R14, are independently selected from the group consisting of H, alkyl (e.g., substituted alkyl) (e.g., unsubstituted alkyl), fluoroalkyl,

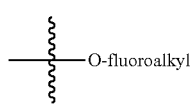

(e.g., substituted alkyl) (e.g., unsubstituted alkyl), aminoalkyl,

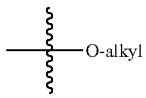

(e.g., substituted alkyl) (e.g., unsubstituted alkyl),

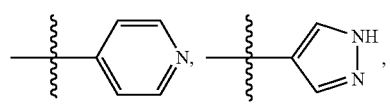

-continued

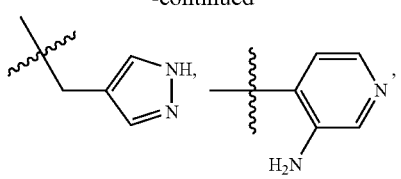

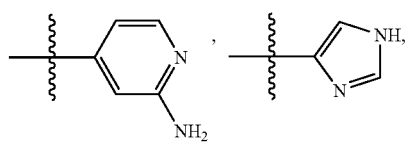

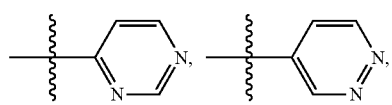

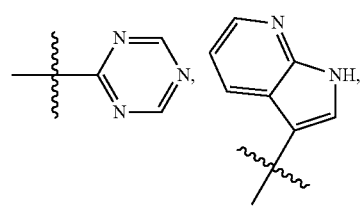

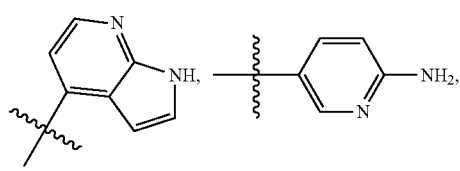

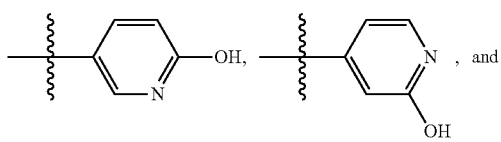

substituted and unsubstituted, and derivatives thereof.

In some embodiments, R15, R16, R17, and R18 are independently selected from the group consisting of C, N, O, and S.

In some embodiments, R19 is selected from the group consisting of H, alkyl (e.g., substituted alkyl) (unsubstituted alkyl), ketone, a chemical moiety (e.g., substituted alkyl) (unsubstituted alkyl) comprising nitrogen, a chemical moiety (e.g., substituted alkyl) (unsubstituted alkyl) comprising oxygen, and a chemical moiety (e.g., substituted alkyl) (unsubstituted alkyl) comprising sulfur.

In some embodiments, R20 is selected from the group consisting of H, alkyl (e.g., substituted alkyl) (unsubstituted alkyl), ketone, a chemical moiety (e.g., substituted alkyl) (unsubstituted alkyl) comprising nitrogen, a chemical moiety (e.g., substituted alkyl) (unsubstituted alkyl) comprising oxygen, and a chemical moiety (e.g., substituted alkyl) (unsubstituted alkyl) comprising sulfur.

In some embodiments, R21, R22, R23, and R24 are independently selected from the group consisting of being absent, H, halogen, CF3

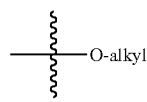

(e.g., substituted alkyl) (e.g., unsubstituted alkyl)

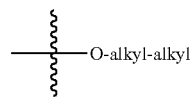

(e.g., substituted alkyl) (e.g., unsubstituted alkyl), OH, fluoroalkyl, sulfonamide, sulfone, OCH$_3$, CH$_3$, SO$_2$R$_{7'}$, SO$_2$N(R$_{7'}$)$_2$, OR$_{7'}$, N(R$_{7'}$)$_2$, CON(R$_{7'}$)$_2$, NHCOR$_{7'}$, NHSO$_2$R$_{7'}$, alkyl, mono-substituted alkyl, di-substituted alkyl, tri-substituted alkyl; wherein R$_{7'}$ is selected from the group consisting of halogen, H, alkyl, mono-substituted alkyl, di-substituted alkyl, tri-substituted alkyl, aryl, mono-substituted aryl, di-substituted aryl, tri-substituted aryl, cycloalipathic, mono-substituted cycloalipathic, di-substituted cycloalipathic, and tri-substituted cycloalipathic; wherein no more than two of R21, R22, R23 and R24 can be hydrogen.

In some embodiments, R25, R26, R27, and R28, are independently selected from the group consisting of hydrogen, alkyl (e.g., substituted alkyl) (e.g., unsubstituted alkyl), fluoroalkyl,

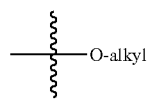

(e.g., substituted alkyl) (e.g., unsubstituted alkyl), aminoalkyl,

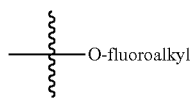

(e.g., substituted alkyl) (e.g., unsubstituted alkyl),

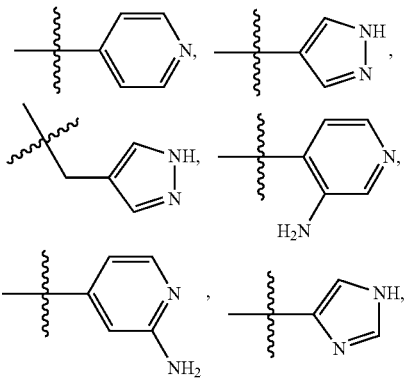

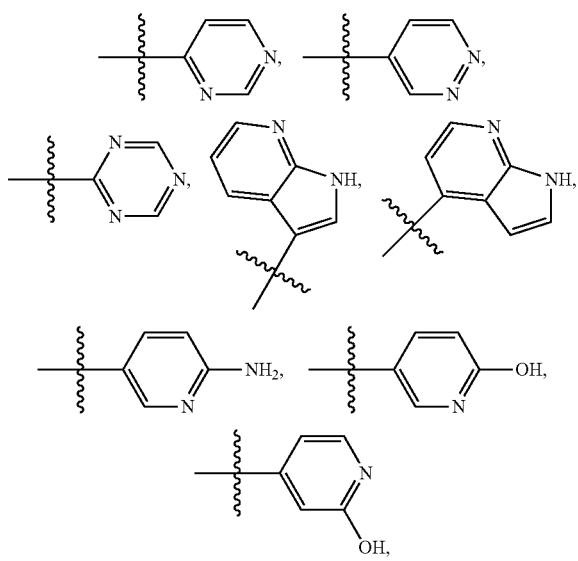
and substituted and unsubstituted, and derivatives thereof; wherein no more than three of R25, R26, R27 and R28 can be hydrogen.
In some embodiments, the formula is selected from the group consisting of:
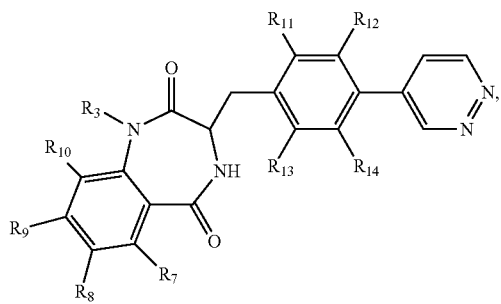
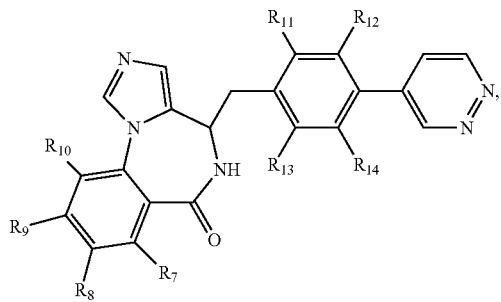
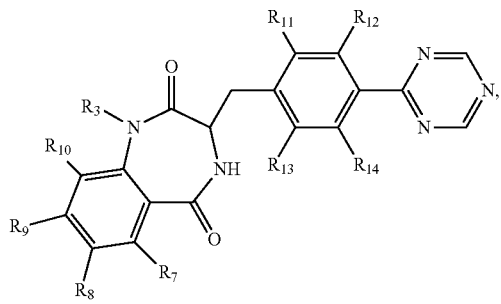
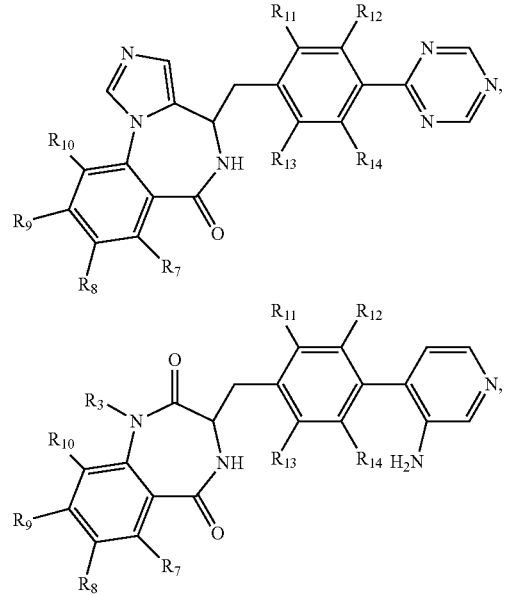
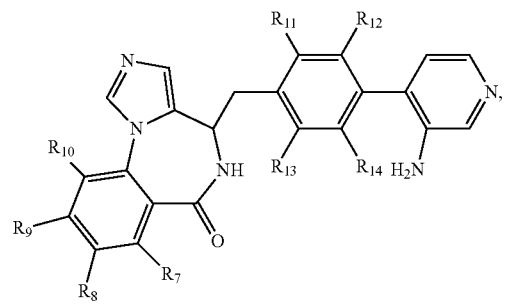
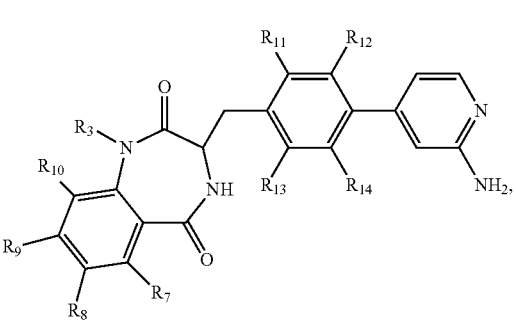
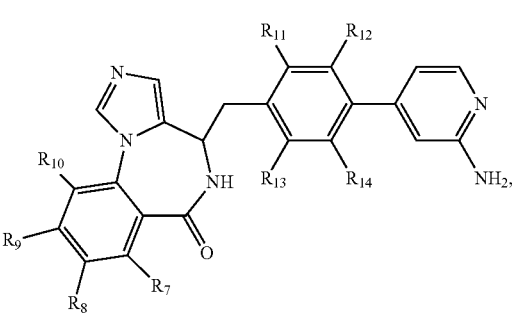

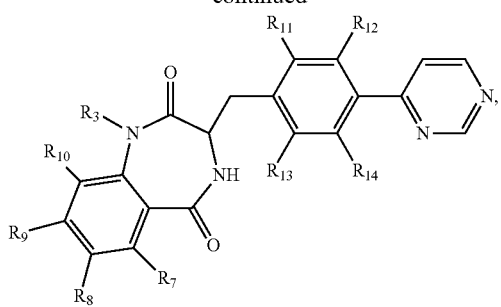
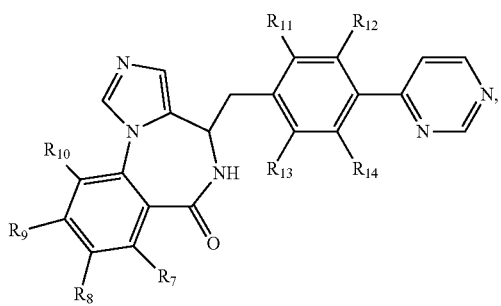
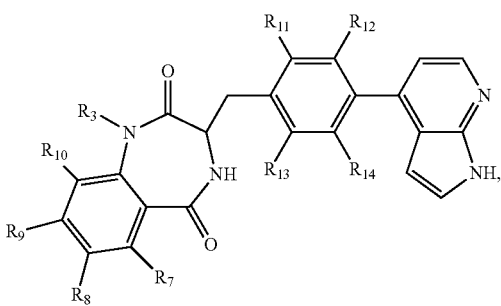
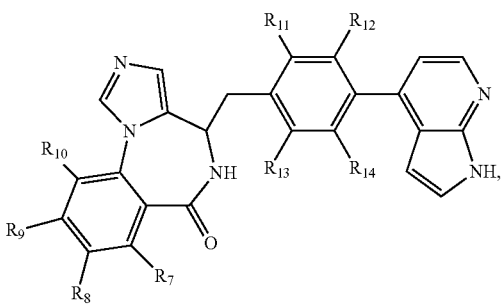
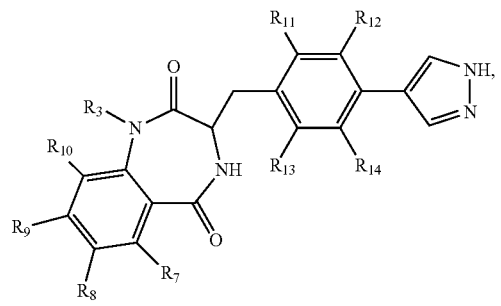
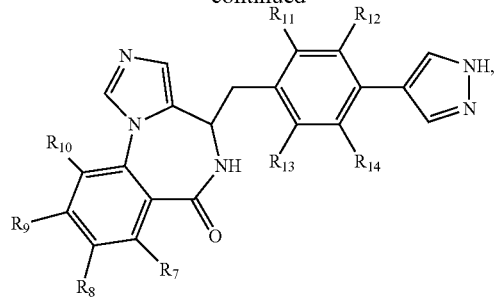
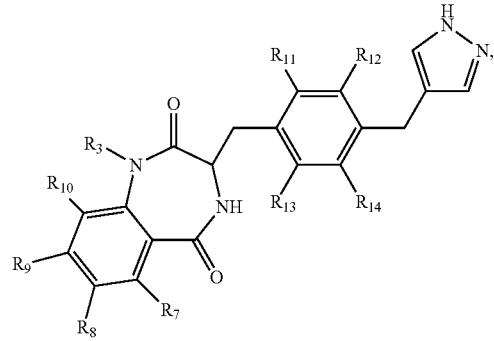
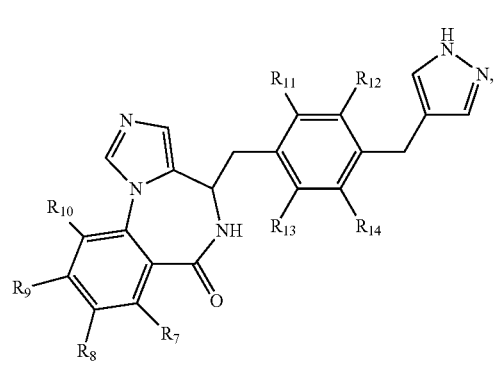
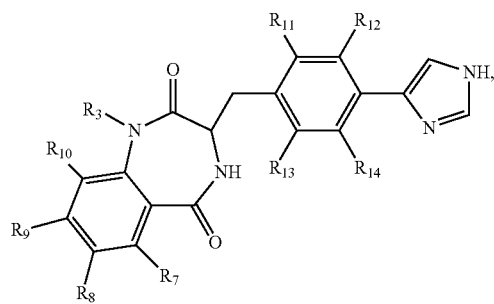
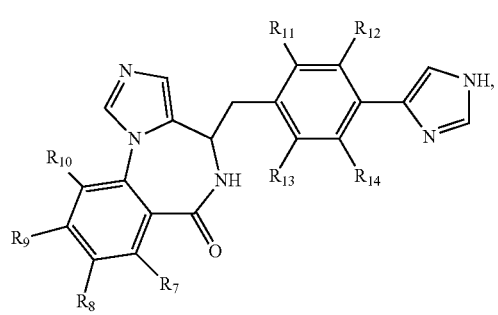

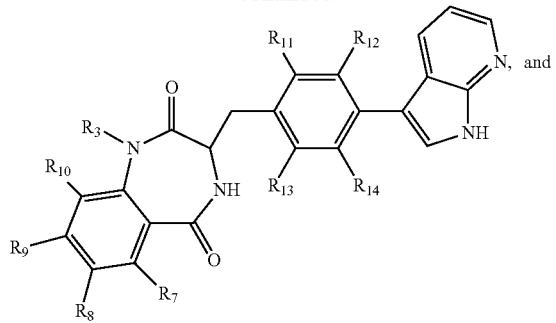
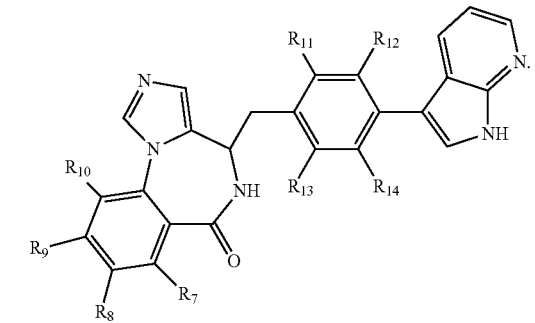
Certain compounds of the present invention include, but are not limited to,
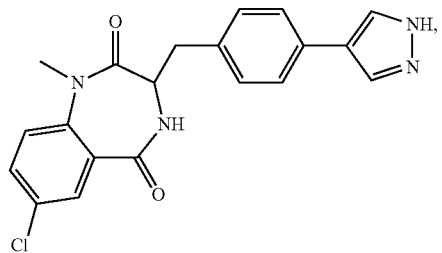
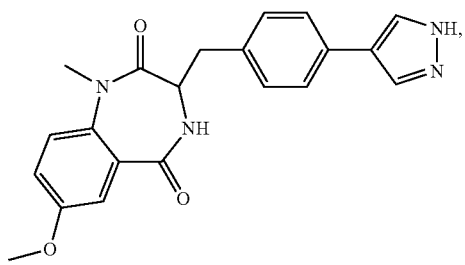
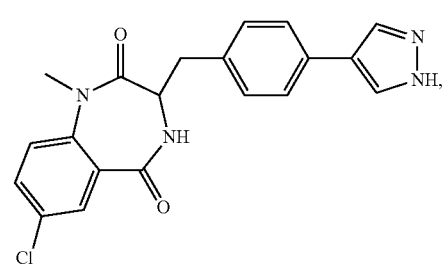
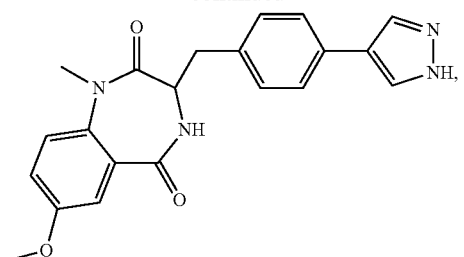
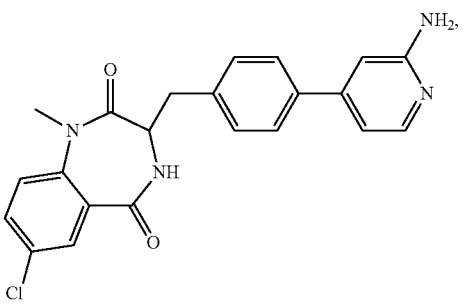
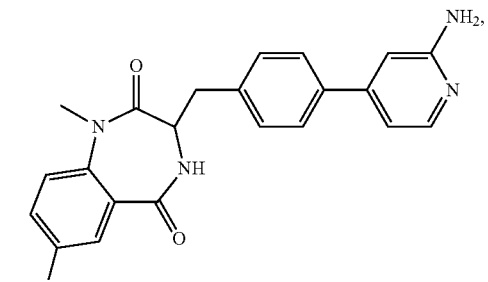
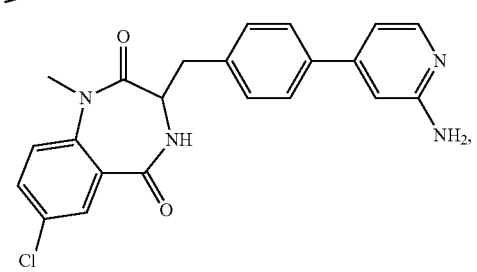
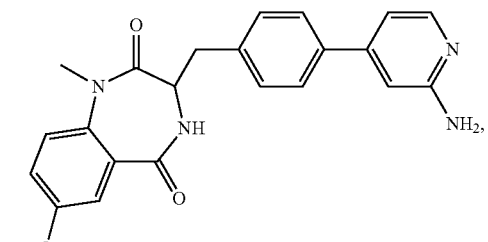
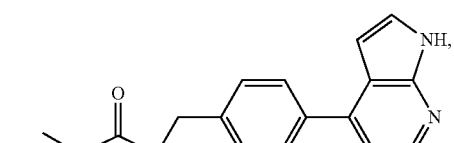
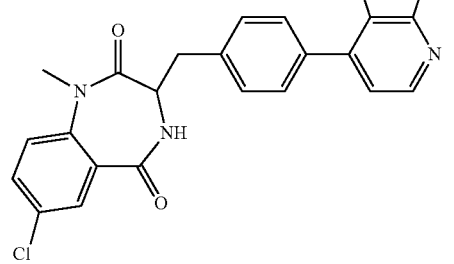

-continued
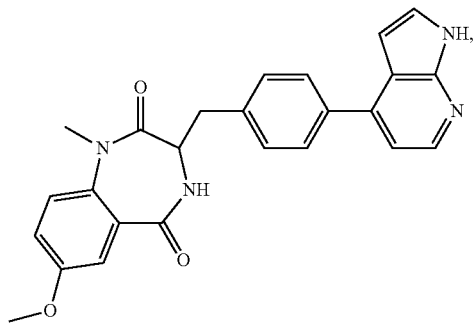
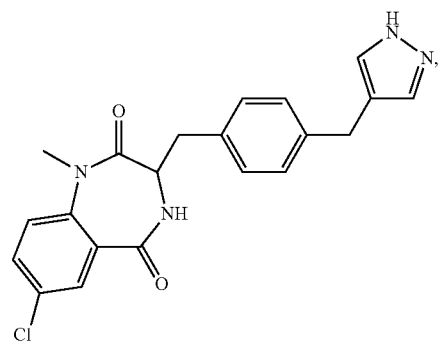
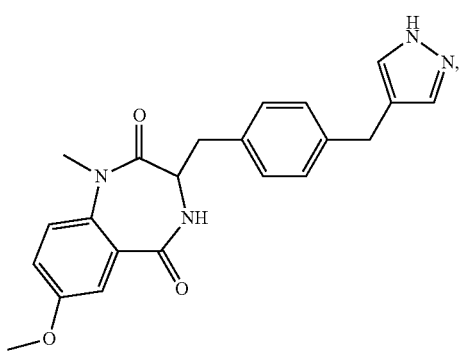
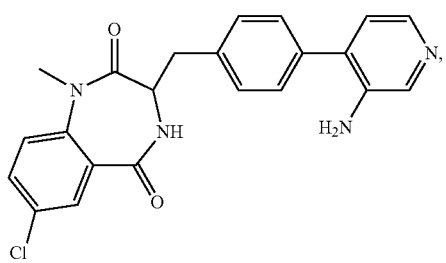
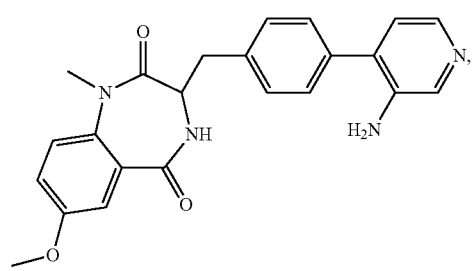
-continued
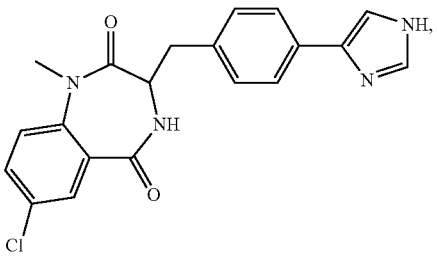
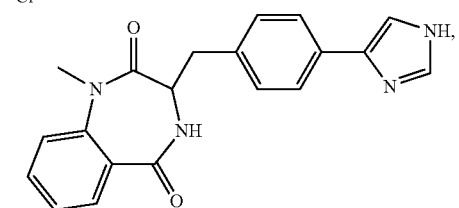
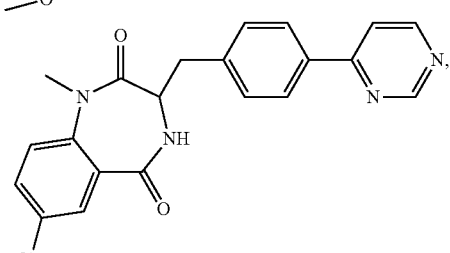
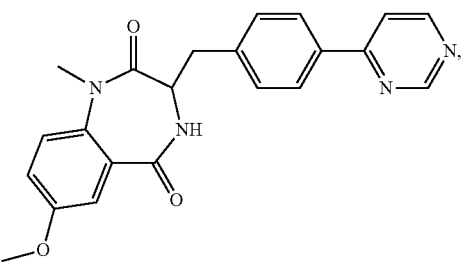
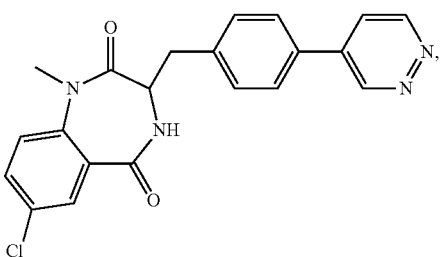

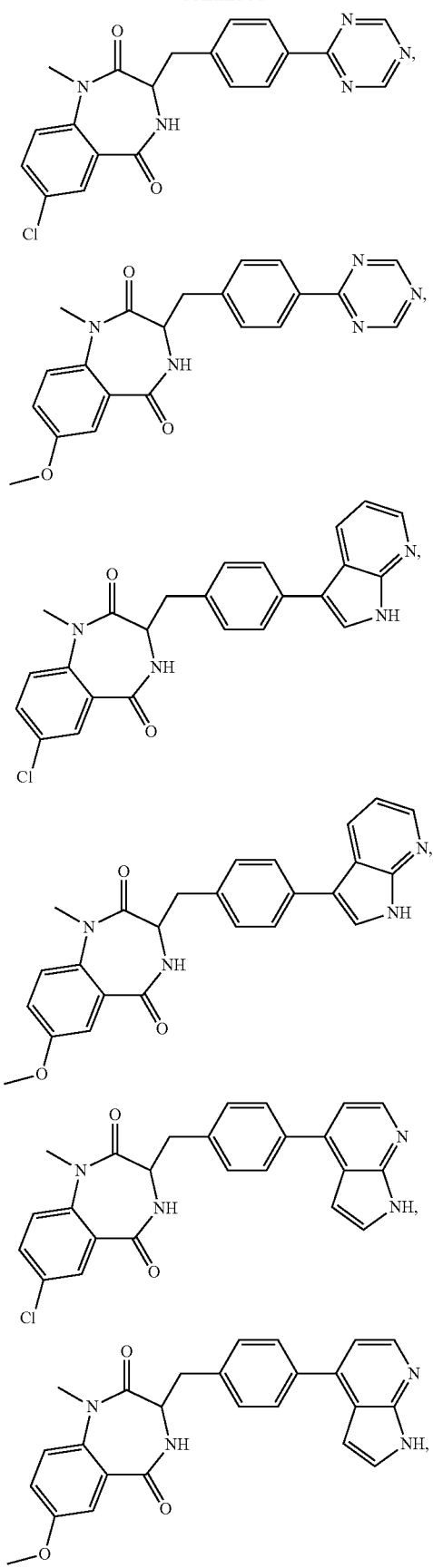
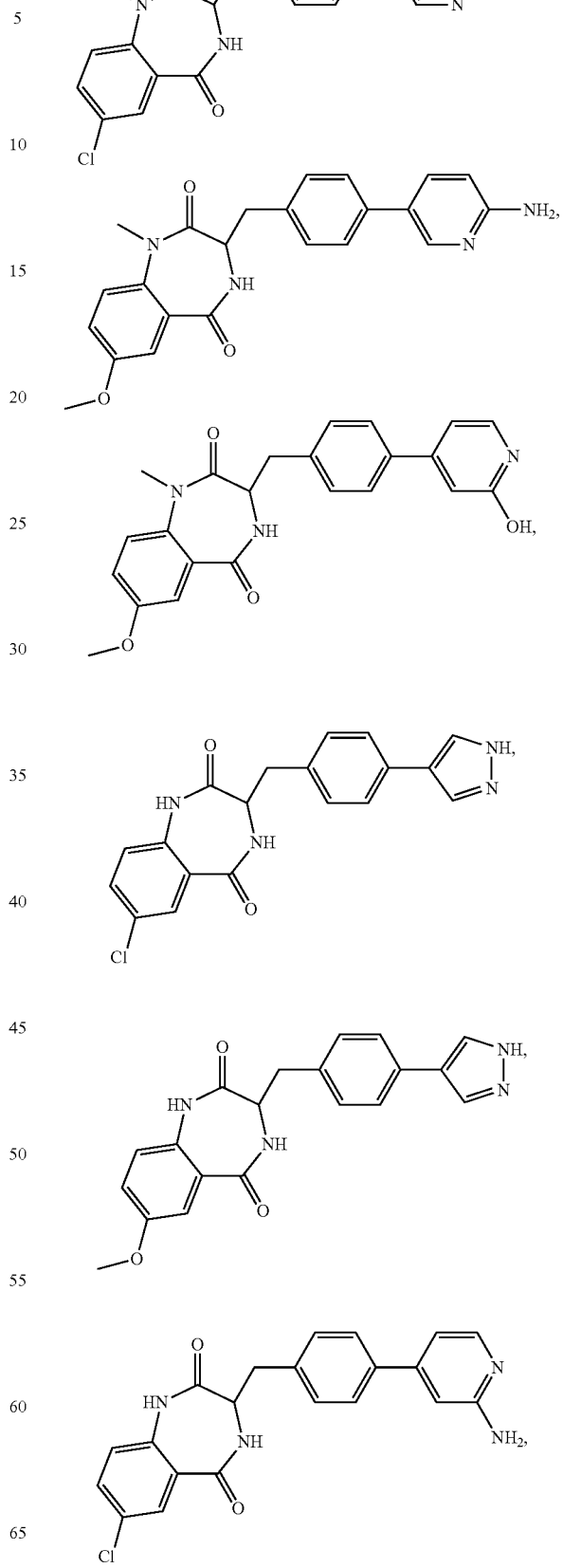

23
-continued
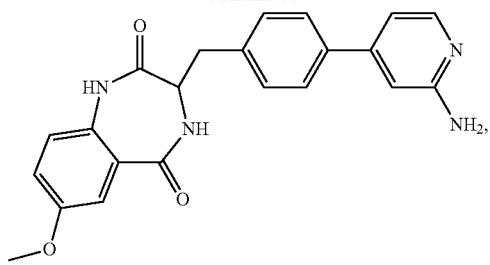
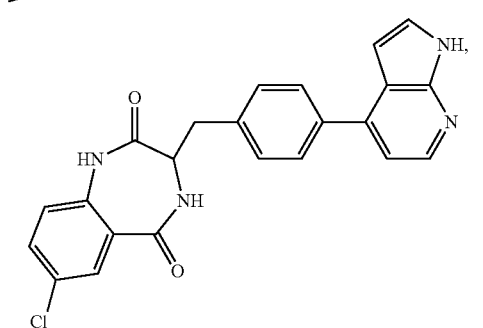
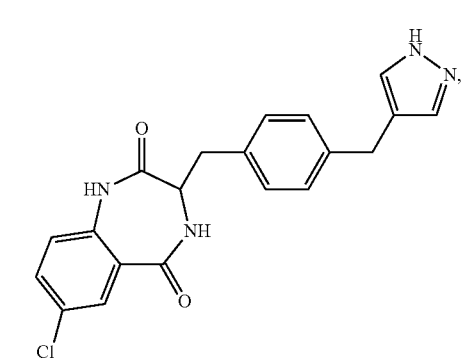
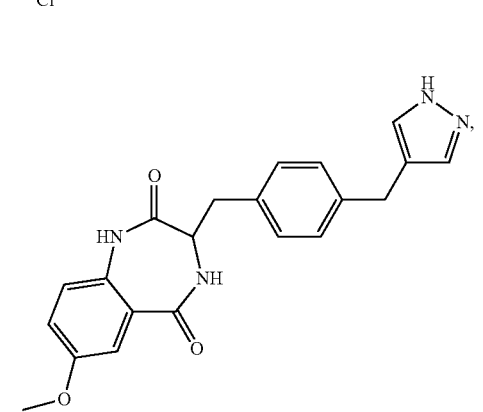
24
-continued
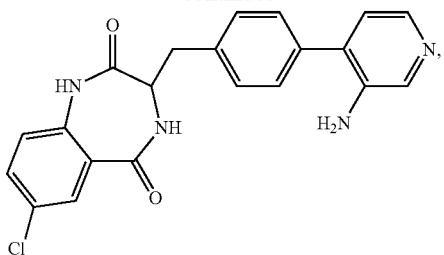
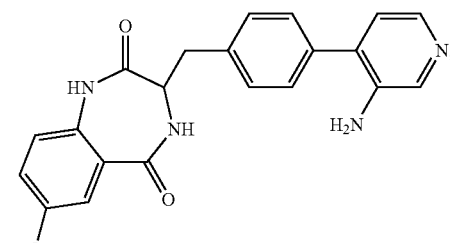
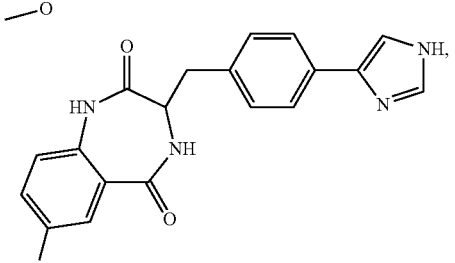
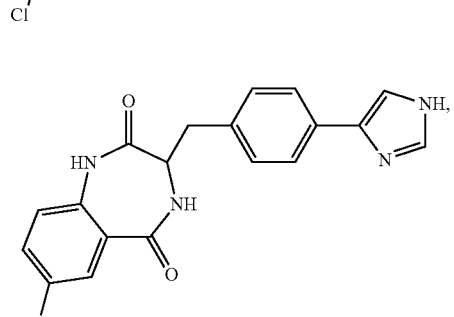
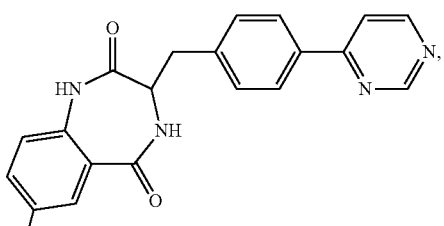
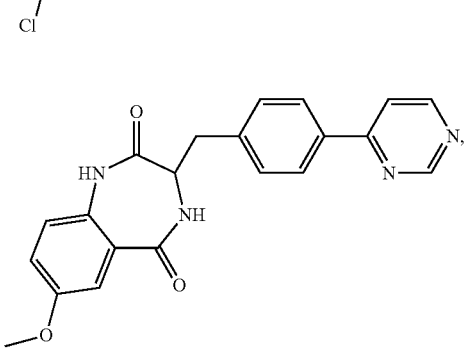

25
-continued
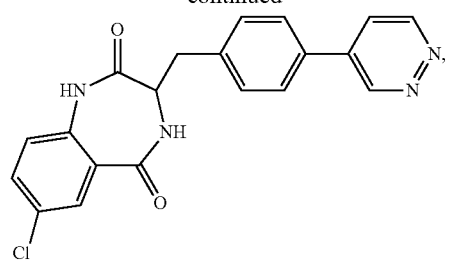
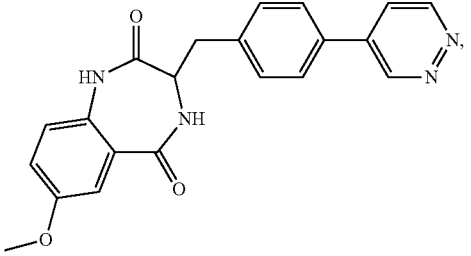
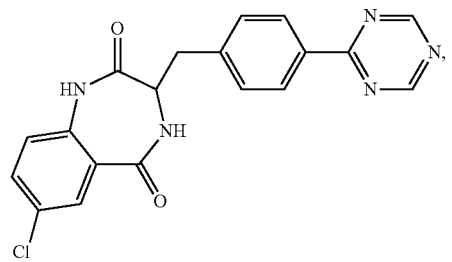
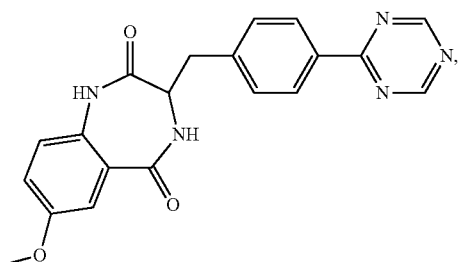
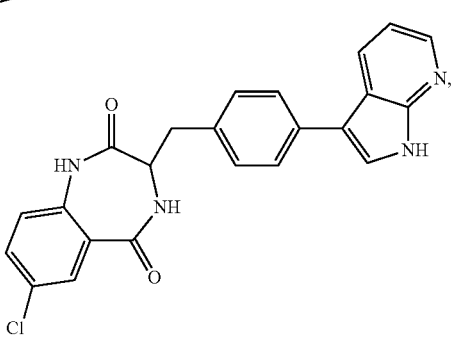
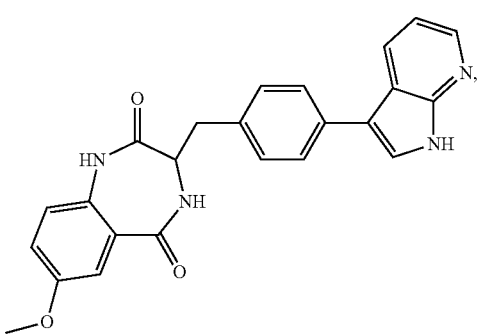
26
-continued
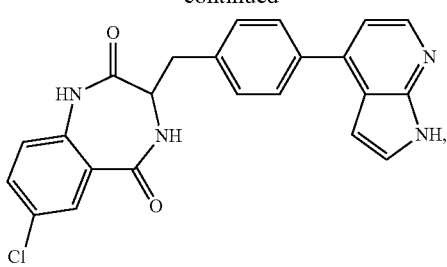
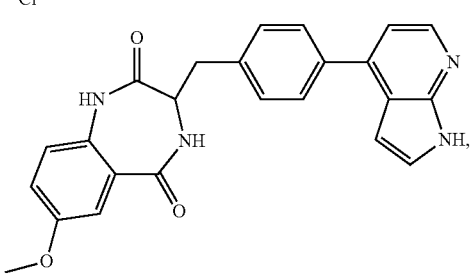
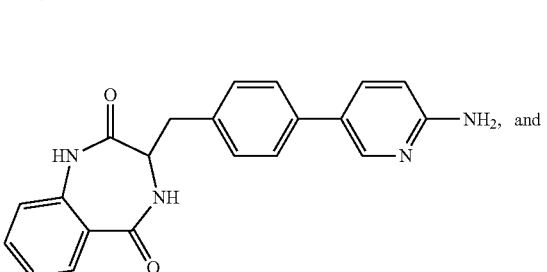
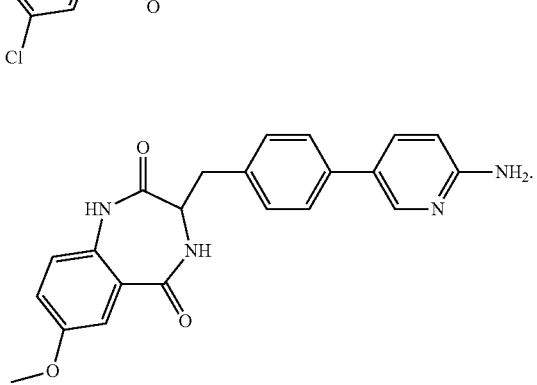
Experiments conducted during the course of developing embodiments for the present invention identified compounds that selectively inhibit ROCK2 activity over ROCK1 (see, e.g., Table 1 and Example II). As such, the present invention provides the following compounds that selectively ROCK2 activity over ROCK1:
(compound 1)
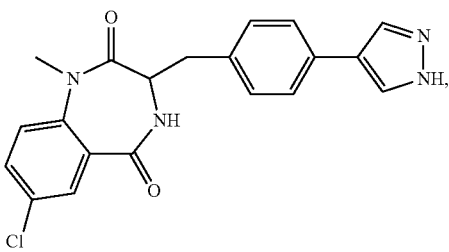

-continued

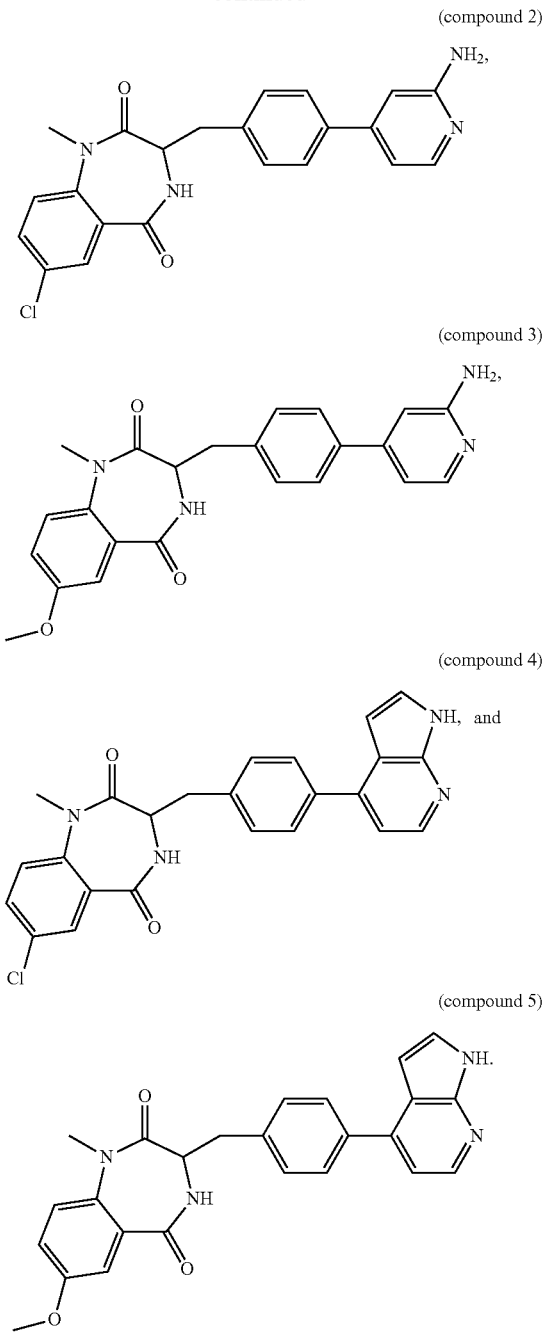

(compound 2)

(compound 3)

(compound 4)

(compound 5)

In certain embodiments, the present invention provides pharmaceutical preparations comprising one or more of the Rho kinase activity inhibiting compounds of the present invention.

In certain embodiments, the present invention provides methods for treating a disorder comprising administering an effective amount of a pharmaceutical preparation to a subject suffering from the disorder, wherein the disorder is associated with aberrant Rho kinase activity, and wherein the pharmaceutical preparation comprises one or more of the Rho kinase activity inhibiting compounds of the present invention. In some embodiments, the compound is a selective Rho kinase inhibitor (e.g., inhibits ROCK1 more than ROCK2) (e.g., inhibits ROCK2 more than ROCK1). In some embodiments, the compound that selectively inhibits ROCK2 activity over ROCK1 (see, e.g., compounds 1-5 as shown in Table 1 and Example II). In some embodiments, the subject is a human subject (e.g., a human subject suffering from the disorder).

Any one or more of these compounds can be used to treat a variety of disorders related to Rho kinase activity including, but not limited to, cardiovascular disorders (e.g., angina (e.g., angina pectoris), atherosclerosis, stroke, cerebrovascular disease (e.g., cerebral thrombosis, cerebral embolism, and cerebral hemorrhage), congestive heart failure, coronary artery disease, myocardial infarction, peripheral vascular disease, stenosis (e.g., coronary artery stenosis, aortic stenosis, restenosis, pulmonary stenosis), vasospasm (e.g., cerebral artery vasospasm, coronary artery vasospasm), hypertension (e.g., pulmonary artery hypertension, systemic arterial hypertension)), smooth muscle related disorders (e.g., glaucoma, erectile dysfunction, bronchial asthma), granulomatosus disorders (e.g., sarcoidosis, Wegener's granulomatosus), and acute macrophage-mediated diseases (e.g., adult respiratory distress syndrome).

In some embodiments, the disorder is an autoimmune disorder. Examples of autoimmune disorders include, but are not limited to, rheumatoid arthritis, psoriasis, chronic graft-versus-host disease, acute graft-versus-host disease, Crohn's disease, multiple sclerosis, systemic lupus erythematosus, Celiac Sprue, idiopathic thrombocytopenic thrombotic purpura, myasthenia gravis, Sjogren's syndrome, scleroderma, or psoriatic epidermal hyperplasia. In certain other embodiments, the autoimmune disorder is psoriasis, chronic graft-versus-host disease, acute graft-versus-host disease, Crohn's disease, systemic lupus erythematosus, or psoriatic epidermal hyperplasia. In some embodiments, the autoimmune disorder is a type of psoriasis selected from the group consisting of plaque psoriasis, guttate psoriasis, inverse psoriasis, pustular psoriasis, and erythrodermic psoriasis. In some embodiments, the immune disorder is inflammatory bowel disease or ulcerative colitis. In some embodiments, the immune disorder is an immune disorder associated with or arising from activity of pathogenic lymphocytes. In some embodiments, the immune disorder is an immune disorder susceptible to treatment by administering to a patient with the immune disorder an active agent that inhibits mitochondrial respiration.

In some embodiments, the autoimmune disorder is arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, uveitis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, ploymyalgia rheumatica, sarcoidosis, sclerosis, primary biliary sclerosis, sclerosing cholangitis, dermatitis, atopic dermatitis, Still's disease, chronic obstructive pulmonary disease, Guillain-Barre disease, Graves' disease, Addison's disease, Raynaud's phenomenon, or autoimmune hepatitis.

Additionally, any one or more of these compounds can be used in combination with at least one other therapeutic agent in the treatment.

In some embodiments, the disorder is related to pro-inflammatory cytokine expression (e.g., IL-17 and/or IL-21) (e.g., pathways related to IL-17 and/or IL-21 expression (e.g., IRF4)). For example, it has been demonstrated that inhibition of ROCK2 results in inhibited expression of pro-inflammatory cytokines (e.g., IL-17 and/or IL-21) (see, e.g., Biswas, et al., J. Clin. Inv. 2010, 120(9), 3280-3295; herein incorporated by reference in its entirety). Accordingly, in some embodiments, pro-inflammatory cytokine expression (e.g., IL-17 and/or IL-21) (e.g., pathways related to IL-17 and/or IL-21 expression (e.g., IRF4)) inihibition is accomplished through use of any of the compounds of the present invention that selectively inhibits ROCK2 activity over ROCK1 (see, e.g., compounds 1-5 as shown in Table 1 and Example II). The methods are not limited to a particular manner of pro-inflammatory cytokine expression (e.g., IL-17 and/or IL-21) (e.g., pathways related to IL-17 and/or IL-21 expression (e.g., IRF4)) inihibition. For example, in some embodiments, pro-inflammatory cytokine expression (e.g., IL-17 and/or IL-21) inihibition is achieved through inhibition of ROCK2 which, for example, thereby inhibits IRF4 expression (e.g., through prevention of IRF4 phosphorylation) which, for example, inhibits IL17 and/or IL-21 expression.

The methods are not limited to a disorder related to pro-inflammatory cytokine expression (e.g., IL-17 and/or IL-21) (e.g., pathways related to IL-17 and/or IL-21 expression (e.g., IRF4)). In some embodiments, the disorder is an inflammatory disorder. Inflammatory disorders include but are not limited to arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

In certain embodiments, the present invention provides methods for inhibiting Rho kinase activity. The methods are not limited to a particular technique. In some embodiments, the methods involve exposing target cells to a composition comprising one or more of the Rho kinase activity inhibiting compounds of the present invention. In some embodiments, the composition binds to the target cells so as to inhibit Rho kinase activity within the target cells. The methods are not limited to particular types of cells. In some embodiments, the cells are, for example, in vitro cells, in vivo cells, ex vivo cells, and/or cancer cells.

In certain embodiments, the present invention provides methods for inhibiting pro-inflammatory cytokine expression (e.g., IL-17 and/or IL-21) (e.g., pathways related to IL-17 and/or IL-21 expression (e.g., IRF4)). The methods are not limited to a particular technique. In some embodiments, the methods involve exposing target cells to a composition comprising one or more of the Rho kinase activity inhibiting compounds of the present invention that selectively inhibit selectively inhibits ROCK2 activity over ROCK1 (see, e.g., compounds 1-5 as shown in Table 1 and Example II). In some embodiments, the composition binds to the target cells so as to inhibit pro-inflammatory cytokine expression (e.g., IL-17 and/or IL-21) (e.g., pathways related to IL-17 and/or IL-21 expression (e.g., IRF4)) within the target cells. The methods are not limited to particular types of cells. In some embodiments, the cells are, for example, in vitro cells, in vivo cells, ex vivo cells, and/or cancer cells. The methods are not limited to a particular manner of pro-inflammatory cytokine expression (e.g., IL-17 and/or IL-21) inihibition. For example, in some embodiments, pro-inflammatory cytokine expression (e.g., IL-17 and/or IL-21) inihibition is achieved through inhibition of ROCK2 which, for example, thereby inhibits IRF4 expression (e.g., through prevention of IRF4 phosphorylation) which, for example, inhibits IL17 and/or IL-21 expression.

In certain embodiments, the present invention provides methods for treating an inflammatory disorder comprising administering an effective amount of a pharmaceutical preparation (e.g., comprising a compound configured to inhibit ROCK2 activity) to a subject suffering from the inflammatory disorder. The present invention is not limited to a particular compound configured to inhibit ROCK2 activity. Examples of compounds configured to inhibit ROCK2 activity include, but are not limited to,

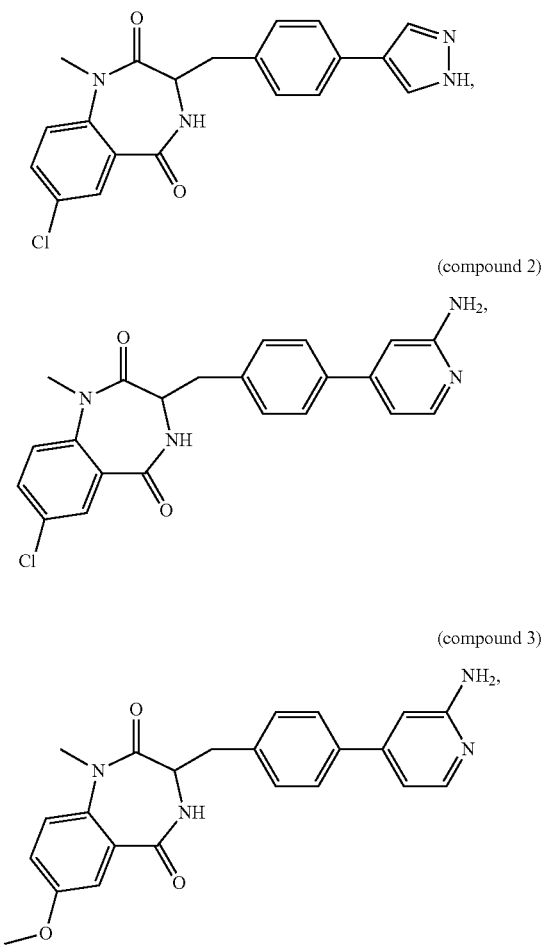

(compound 1)
(compound 2)
(compound 3)
(compound 4)

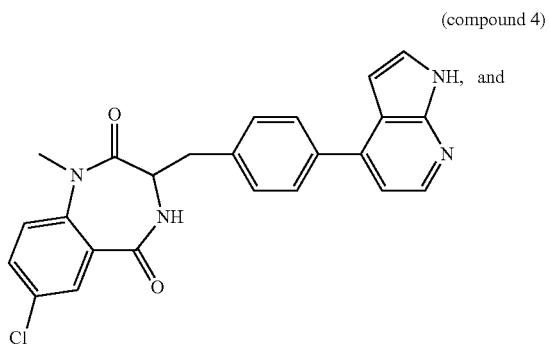

(compound 5)

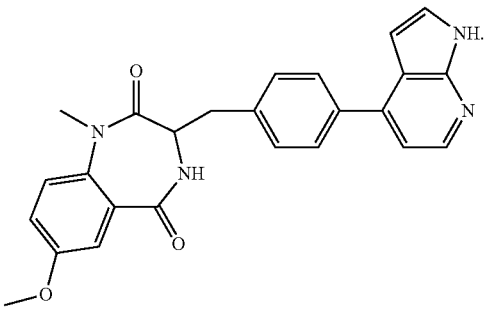

In some embodiments, the inflammatory disorder is associated with aberrant pro-inflammatory cytokine activity (e.g., aberrant IL-17 and/or IL-21 and/or IRF4 activity). In some embodiments, the subject is a human.

The methods are not limited to a particular inflammatory disorder. Indeed, examples of inflammatory disorders include, but are not limited to, arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

In some embodiments, the methods involve co-administering to the subject a therapeutic agent configured for treating said inflammatory disorders. Examples of such agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), and glucocorticoids (e.g., prednisone, methylprednisone), IL-1 inhibitors, IL-17 inhibitors, IL-21 inhibitors, and metalloprotease inhibitors.

DEFINITIONS

To facilitate an understanding of the present invention, a number of terms and phrases are defined below.

As used herein, the term "ROCK," "Rho kinase," or similar terms, refer to serine/threonine protein kinases with a molecular mass of approximately 160 kDa. Two isoforms encoded by two different genes have been identified: ROCKI (also known as ROKβ or p160ROCK) and ROCKII (or ROKα).

As used herein, the terms "selective ROCK inhibitor," "selective ROCK inhibiting compound," or similar terms, refer to a natural or synthetic compound of the present invention which selectively inhibit ROCK1, and/or ROCK2 activity, and/or pathways related to ROCK1 and/or ROCK2 activity (e.g., pro-inflammatory cytokine expression (e.g., IL-17 and/or IL21 and/or related pathways (e.g., pathways related to IL-17 and/or IL-21 expression (e.g., IRF4)). The selective ROCK inhibiting compounds are not limited to a particular manner of selective ROCK inhibition. For example, in some embodiments, one or more of the selective ROCK inhibiting compounds selectively inhibit ROCK1 activity over ROCK2 activity. For example, in some embodiments, one or more of the selective ROCK inhibiting compounds selectively inhibit ROCK2 activity over ROCK1 activity (see, e.g., compounds 1-5 as described in Table 1 and Example II). Moreover, in some embodiments, one or more of the selective ROCK inhibiting compounds selectively inhibit both ROCK1 activity and ROCK2 activity with similar capability.

As used herein, the term "benzodiazepine" refers to a seven membered non-aromatic heterocyclic ring fused to a phenyl ring wherein the seven-membered ring has two nitrogen atoms, as part of the heterocyclic ring. In some aspects, the two nitrogen atoms are in the 1 and 4 positions or the 1 and 5 positions, as shown in the general structures below:

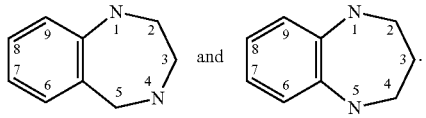 [SMILES: c1ccc2c(c1)CNCCN2 ; c1ccc2c(c1)NCCCN2]

The term "larger than benzene" refers to any chemical group containing 7 or more non-hydrogen atoms.

The term "chemical moiety" refers to any chemical compound containing at least one carbon atom. Examples of chemical moieties include, but are not limited to, aromatic chemical moieties, chemical moieties comprising Sulfur, chemical moieties comprising Nitrogen, hydrophilic chemical moieties, and hydrophobic chemical moieties.

As used herein, the term "aliphatic" represents the groups including, but not limited to, alkyl, alkenyl, alkynyl, and acyclic.

As used herein, the term "aryl" represents a single aromatic ring such as a phenyl ring, or two or more aromatic rings (e.g., biphenyl, naphthalene, anthracene), or an aromatic ring and one or more non-aromatic rings. The aryl group can be optionally substituted with a lower aliphatic group (e.g., alkyl, alkenyl, alkynyl, or acyclic). Additionally, the aliphatic and aryl groups can be further substituted by one or more functional groups including, but not limited to, chemical moieties comprising N, S, O, —NH$_2$, —NHCOCH$_3$, —OH, lower alkoxy (C$_1$-C$_4$), and halo (—F, —Cl, —Br, or —I).

As used herein, the term "substituted aliphatic" refers to an alkane, alkene, alkyne, or alcyclic moiety where at least one of the aliphatic hydrogen atoms has been replaced by, for example, a halogen, an amino, a hydroxy, an ether, a nitro, a thio, a ketone, a sulfone, a sulfonamide, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ether, an ester, an amide, a sulfone, a sulfonamide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a heteroatom, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Nonlimiting examples of heterocyclic rings containing two different heteroatoms include, but are not limited to, phenothiazine, morpholine, parathiazine, oxazine, oxazole, thiazine, and thiazole. The heterocyclic ring is optionally further substituted with one or more groups selected from aliphatic, nitro, acetyl (i.e., —C(=O)—CH$_3$), or aryl groups.

As used herein, the term "substituted heterocyclic" refers to a heterocylic structure where at least one of the ring hydrogen atoms is replaced by oxygen, nitrogen or sulfur, and where at least one of the aliphatic hydrogen atoms has been replaced by a halogen, hydroxy, a thio, nitro, an amino, an ether, a sulfone, a sulphonamide, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "electron-rich heterocycle," means cyclic compounds in which one or more ring atoms is a heteroatom (e.g., oxygen, nitrogen or sulfur), and the heteroatom has unpaired electrons which contribute to a 6-π electronic system. Exemplary electron-rich heterocycles include, but are not limited to, pyrrole, indole, furan, benzofuran, thiophene, benzothiophene and other similar structures.

As used herein, the term "linker" refers to a chain containing up to and including eight contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

As used herein, the term "a moiety that participates in hydrogen bonding" as used herein represents a group that can accept or donate a proton to form a hydrogen bond thereby. Some specific non-limiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups ($C_1$-$C_4$) to which the respective oxygen-containing functional group is attached. Thus, for example, the term "lower carbonyl" refers to inter alia, formaldehyde, acetaldehyde. Some nonlimiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups. It is also possible that the hydrogen-bond acceptor in the present invention can be the π electrons of an aromatic ring.

The term "derivative" of a compound, as used herein, refers to a chemically modified compound wherein the chemical modification takes place either at a functional group of the compound (e.g., aromatic ring) or benzodiazepine backbone. Such derivatives include, but are not limited to, esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein, the term "immune disorder" refers to any condition in which an organism produces antibodies or immune cells which recognize the organism's own molecules, cells or tissues. Non-limiting examples of immune disorders include autoimmune disorders, immune hemolytic anemia, immune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, tuberculosis, and the like.

As used herein, an "inflammatory disorder" refers to disorders characterized by, caused by, resulting from, or becoming affected by inflammation. An inflammatory disorder may be caused by or be associated with biological and pathological processes associated with, for example, pro-inflammatory cytokine expression (e.g., IL-17 and/or IL-21) (e.g., pathways related to IL-17 and/or IL-21 expression (e.g., IRF4)). Examples of inflammatory diseases or disorders include, but are not limited to, acute and chronic inflammatory disorders such as asthma, psoriasis, rheumatoid arthritis, osteoarthritis, psoriatic arthritis, inflammatory bowel disease (Crohn's disease, ulcerative colitis), ankylosing spondylitis, sepsis, vasculitis, and bursitis, autoimmune diseases such as Lupus, Polymyalgia, Rheumatica, Scleroderma, Wegener's granulomatosis, temporal arteritis, cryoglobulinemia, and multiple sclerosis, transplant rejection, osteoporosis, cancer, including solid tumors (e.g., lung, CNS, colon, kidney, and pancreas), Alzheimer's disease, atherosclerosis, viral (e.g., HIV or influenza) infections, and chronic viral (e.g., Epstein-Barr, cytomegalovirus, herpes simplex virus) infection.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans.

In the context of the invention, the term "subject" generally refers to an individual who will receive or who has received treatment (e.g., administration of a compound of the present invention and optionally one or more other agents) for a condition associated with aberrant Rho kinase activity.

The term "diagnosed," as used herein, refers to the to recognition of a disease by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

In preferred embodiments, the "target cells" of the compositions and methods of the present invention include, refer to, but are not limited to, cells having aberrant or non-aberrant Rho kinase activity.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "co-administration" refers to the administration of at least two agent(s) (e.g., a compound of the present invention) or therapies to a subject. In some embodiments, the co-administration of two or more agents/ therapies is concurrent. In other embodiments, a first agent/ therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "modulate" refers to the activity of a compound (e.g., a compound of the present invention) to affect (e.g., to promote or retard) an aspect of cellular function, including, but not limited to, inhibiting Rho kinase activity.

DETAILED DESCRIPTION OF THE INVENTION

Rho-Kinase (ROCK) is a member of the serine-threonine protein kinase family. ROCK exists in two isoforms, ROCK1 and ROCK2 (see, e.g., T. Ishizaki et al., EMBO J., 1996, 15, 1885-1893; herein incorporated by reference in its entirety). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as acting organization, cell adhesion, cell migration, and cytokinesis (see, e.g., K. Riento and A. J. Ridley, Nat Rev Mol Cell Biol, 2003, 4, 446-56; herein incorporated by reference in its entirety). It is also directly involved in regulating smooth muscle contraction (see, e.g., A. P. Somlyo, Nature, 1997, 389, 908-911; herein incorporated by reference in its entirety). Upon activation of its receptor, RhoA is activated and in turn it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension. In addition, activated ROCK (e.g., ROCK2) has been shown to inhibit phosphorylation of IRF4 which in turn results in decreased pro-inflammatory cytokine (e.g., IL-17 and/or IL-21) expression (see, e.g., Biswas, et al., J. Clin. Inv. 2010, 120(9), 3280-3295; herein incorporated by reference in its entirety). There is considerable evidence in the literature that the RhoA/ROCK signaling pathway plays an important role in signal transduction initiated by several vasoactive factors, for example angiotensin II, urotension II, endothelin-1, serotonin, norepinephrine and platelet-derived growth factor (PDGF). Many of these factors are implicated in the pathogenesis of cardiovascular disease.

Additional studies in the literature, some using known ROCK inhibitors fasudil (see, e.g., T. Asano et al., J. Pharmacol. Exp. Ther., 1987, 24, 1033-1040; herein incorporated by reference in its entirety) or Y-27632 (see, e.g., M. Uehata et al., Nature, 1997, 389, 990-994; herein incorporated by reference in its entirety) further illustrate the link between ROCK and cardiovascular disease. For example, ROCK expression and activity have been shown to be elevated in spontaneously hypertensive rats, suggesting a link to the development of hypertension in these animals. The ROCK inhibitor Y-27632 (see, e.g., M. Uehata et al., Nature, 1997, 389, 990-994; herein incorporated by reference in its entirety) was shown to significantly decrease blood pressure in three rat models of hypertension, including the spontaneously hypertensive rat, renal hypertensive rat and deoxycortisone acetate salt hypertensive rat models while having only a minor effect on blood pressure in control rats, reinforcing the link between ROCK and hypertension.

Other studies suggest a link between ROCK and atherosclerosis. For example, gene transfer of a dominant negative form of ROCK suppressed neointimal formation following balloon injury in porcine femoral arteries. In a similar model, ROCK inhibitor Y-27632 also inhibited neointimal formation in rats. In a porcine model of IL-1 beta-induced coronary stenosis, long term treatment by ROCK inhibitor fasudil was shown to progressively reduce coronary stenosis as well as promote a regression of coronary constrictive remodeling. A link between ROCK and pro-inflammatory cytokine expression (e.g., IL-17 and/or IL-21) has been demonstrated. For example, it has been demonstrated that inhibition of ROCK2 inhibits expression of pro-inflammatory cytokines (e.g., IL-17 and/or IL-21) (see, e.g., Biswas, et al., J. Clin. Inv. 2010, 120(9), 3280-3295; herein incorporated by reference in its entirety) (e.g., activated ROCK (e.g., ROCK2) was shown to inhibit phosphorylation of IRF4 which in turn resulted in decreased pro-inflammatory cytokine (e.g., IL-17 and/or IL-21) expression). Accordingly, the present invention provides methods for inhibiting pro-inflammatory cytokine expression (e.g., IL-17 and/or IL-21) and/or disorders related to such pro-inflammatory cytokine expression through use of the compounds of the present invention.

Additional investigations suggest that a ROCK inhibitor would be useful in treating other cardiovascular diseases. For example, in a rat stroke model, fasudil was shown to reduce both the infarct size and neurologic deficit. The ROCK inhibitor Y-27632 was shown to improve ventricular hypertrophy and function in a model of congestive heart failure in Dahl salt-sensitive rats.

Other animal or clinical studies have implicated ROCK in additional diseases including coronary vasospasm, cerebral vasospasm, ischemia/reperfusion injury, pulmonary hypertension, angina, renal disease and erectile dysfunction.

The above studies provide evidence for a link between ROCK and cardiovascular diseases including hypertension, atherosclerosis (see, e.g., Retzer, et al. FEBS Lett 2000, 466, 70; herein incorporated by reference in its entirety), restenosis (see, e.g., Eto, et al. Am J Physiol Heart Circ Physiol 2000, 278, H1744; Negoro, et al. Biochem Biophys Res Commun 1999, 262, 211; each of which are herein incorporated by reference in their entireties), stroke, heart failure, coronary vasospasm, cerebral vasospasm, ischemia/reperfusion injury (see, e.g., Uehata, et al. Nature 1997, 389, 990; Seasholtz, et al. Circ Res 1999, 84, 1186; Hitomi, et al. Life Sci 2000, 67, 1929; Yamamoto, et al. J Cardiovasc Pharmacol 2000, 35, 203; each of which are herein incorporated by reference in their entireties), pulmonary hypertension and angina, as well as renal disease and erectile dysfunction (see, e.g., Chitaley, et al. Nat Med 2001, 7, 119; herein incorporated by reference in its entirety). Given the demonstrated effect of ROCK on smooth muscle, ROCK inhibitors may also be useful in other diseases involving smooth muscle hyper reactivity, including asthma and glaucoma. Furthermore, Rho-kinase has been indicated as a drug target for the treatment of various other diseases (e.g., cerebral vasospasm (see, e.g., Sato, et al. Circ Res 2000, 87, 195; Kim, et al. Neurosurgery 2000, 46, 440; herein incorporated by reference in its entirety), central nervous system disorders such as neuronal degeneration and spinal cord injury (see, e.g., Hara, et al. J Neurosurg 2000, 93, 94; Toshima, et al. Stroke 2000, 31, 2245; each of which are herein incorporated by reference in their entireties), in neoplasias where inhibition of Rho kinase has been shown to inhibit tumor cell growth and metastasis (see, e.g., Itoh, et al. Nat Med 1999, 5, 221; Somlyo, et al. Biochem Biophys Res Commun 2000, 269, 652; each of which are herein incorporated by reference in their entireties), angiogenesis (see, e.g., Uchida, et al. Biochem Biophys Res Commun 2000, 269, 633; Gingras, et al. Biochem J 2000, 348 Pt 2, 273; each of which are herein incorporated by reference in their entireties), arterial thrombotic disorders such as platelet aggregation (see, e.g., Klages, et al. J Cell Biol 1999, 144, 745; Retzer, et al. Cell Signal 2000, 12, 645; each of which are herein incorporated by reference in their entireties), leukocyte aggregation (see, e.g., Kawaguchi, et al. Eur J Pharmacol 2000, 403, 203; Sanchez-Madrid, et al. Embo J 1999, 18, 501; each of which are herein incorporated by reference in their entireties), asthma (see, e.g., Setoguchi, et al. Br J Pharmacol 2001, 132, 111; Nakahara, et al. Eur J Pharmacol 2000, 389, 103; each of which are herein incorporated by reference in their entireties), regulation of intraocular pressure (see, e.g., Honjo, et al. Invest Opthalmol V is Sci 2001, 42, 137; herein incorporated by reference in its entirety), and bone resorption (see, e.g., Chellaiah, et al. J Biol Chem 2000, 275, 11993; Zhang, et al. J Cell Sci 1995, 108, 2285; each of which are herein incorporated by reference in their entireties)).

Although there are many reports of ROCK inhibitors under investigation (see, e.g., E. Hu and D. Lee, Expert Opin. Ther. Targets, 2005, 9, 715-736; herein incorporated by reference in its entirety), so far fasudil is the only marketed ROCK inhibitor. Accordingly, there remains a need for new therapeutics, including ROCK inhibitors, for the treatment of disorders involving ROCK activity (e.g., cardiovascular disorders (e.g., angina (e.g., angina pectoris), atherosclerosis, stroke, cerebrovascular disease (e.g., cerebral thrombosis, cerebral embolism, and cerebral hemorrhage), congestive heart failure, coronary artery disease, myocardial infarction, peripheral vascular disease, stenosis (e.g., coronary artery stenosis, aortic stenosis, restenosis, pulmonary stenosis), vasospasm (e.g., cerebral artery vasospasm, coronary artery vasospasm), hypertension (e.g., pulmonary artery hypertension, systemic arterial hypertension)), smooth muscle related disorders (e.g., glaucoma, erectile dysfunction, bronchial asthma), granulomatosus disorders (e.g., sarcoidosis, Wegener's granulomatosus), acute macrophage-mediated diseases (e.g., adult respiratory distress syndrome), and autoimmune disorders (e.g., rheumatoid arthritis, systemic lupus erythematosus, multiple sclerosis, irritable bowel syndrome, and systemic sclerosis)).

The present invention provides novel chemical compounds characterized as Rho kinase (ROCK) inhibitors, methods for their discovery, and their therapeutic, research, and diagnostic use. In particular, the present invention provides 1,4-benzodiazepine-2,5-dione compounds and related compounds having ROCK inhibitory activity, and methods of using such compounds as therapeutic agents to treat a number of conditions associated with ROCK activity (e.g., cardiovascular disorders (e.g., angina (e.g., angina pectoris), atherosclerosis, stroke, cerebrovascular disease (e.g., cerebral thrombosis, cerebral embolism, and cerebral hemorrhage), congestive heart failure, coronary artery disease, myocardial infarction, peripheral vascular disease, stenosis (e.g., coronary artery stenosis, aortic stenosis, restenosis, pulmonary stenosis), vasospasm (e.g., cerebral artery vasospasm, coronary artery vasospasm), hypertension (e.g., pulmonary artery hypertension, systemic arterial hypertension)), smooth muscle related disorders (e.g., glaucoma, erectile dysfunction, bronchial asthma), granulomatosus disorders (e.g., sarcoidosis, Wegener's granulomatosus), acute macrophage-mediated diseases (e.g., adult respiratory distress syndrome), and autoimmune disorders (e.g., rheumatoid arthritis, systemic lupus erythematosus, multiple sclerosis, irritable bowel syndrome, and systemic sclerosis)).

In some embodiments, the disorder is an autoimmune disorder. Examples of autoimmune disorders include, but are not limited to, rheumatoid arthritis, psoriasis, chronic graft-versus-host disease, acute graft-versus-host disease, Crohn's disease, multiple sclerosis, systemic lupus erythematosus, Celiac Sprue, idiopathic thrombocytopenic thrombotic purpura, myasthenia gravis, Sjogren's syndrome, scleroderma, or psoriatic epidermal hyperplasia. In certain other embodiments, the autoimmune disorder is psoriasis, chronic graft-versus-host disease, acute graft-versus-host disease, Crohn's disease, systemic lupus erythematosus, or psoriatic epidermal hyperplasia. In some embodiments, the autoimmune disorder is a type of psoriasis selected from the group consisting of plaque psoriasis, guttate psoriasis, inverse psoriasis, pustular psoriasis, and erythrodermic psoriasis. In some embodiments, the immune disorder is inflammatory bowel disease or ulcerative colitis. In some embodiments, the immune disorder is an immune disorder associated with or arising from activity of pathogenic lymphocytes. In some embodiments, the immune disorder is an immune disorder susceptible to treatment by administering to a patient with the immune disorder an active agent that inhibits mitochondrial respiration.

In some embodiments, the autoimmune disorder is arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, uveitis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, ploymyalgia rheumatica, sarcoidosis, sclerosis, primary biliary sclerosis, sclerosing cholangitis, dermatitis, atopic dermatitis, Still's disease, chronic obstructive pulmonary disease, Guillain-Barre disease, Graves' disease, Addison's disease, Raynaud's phenomenon, or autoimmune hepatitis.

In certain embodiments, the present invention provides methods for inhbiting pro-inflammatory cytokine expression (e.g., IL-17 and/or IL-21) and/or disorders related to pro-inflammatory cytokine expression (e.g., IL-17 and/or IL-21) (e.g., inflammatory disorders). The present invention is not limited to a particular technique. The methods are not limited to a particular manner of pro-inflammatory cytokine expression (e.g., IL-17 and/or IL-21) inihibition. For example, in some embodiments, pro-inflammatory cytokine expression (e.g., IL-17 and/or IL-21) inihibition is achieved through inhibition of ROCK2 which, for example, thereby inhibits IRF4 expression (e.g., through prevention of IRF4 phosphorylation) which, for example, inhibits IL17 and/or IL-21 expression.

Exemplary compositions and methods of the present invention are described in more detail in the following sections: I. Exemplary Compounds; II. Pharmaceutical compositions, formulations, and exemplary administration routes and dosing considerations; III. Drug screens; and IV. Therapeutic Applications.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Exemplary Compounds

Exemplary compounds of the present invention are provided below. Certain 1,4-benzodiazepine-2,5-dione derivatives have been described (see, e.g., U.S. patent application Ser. No. 09/700,101; U.S. Pat. No. 6,506,744; Kamal, et al., 2004 Synlett 14:2533-2535; Hulme, et al., 1998 J. Org. Chem. 63:8021-8022; Raboisson et al., 2005 Bioorg. Med. Chem. Lett. 15:1857-1861; Raboisson et al., 2005 Bioorg. Med. Chem. Lett. 15:765-770; Rabiosson et al., 2005 J. Med. Chem. 48:909-912; U.S. Patent Application Publication No. 2007/0111994; each herein incorporated by reference in their entireties). The present invention provides novel 1,4-benzodiazepine-2,5-dione compounds and related compounds, and uses for such compounds.

In certain embodiments, the present invention provides compounds configured to inhibit Rho kinase activity. The present invention is not limited to a particular type or kind of Rho kinase inhibitor. Experiments conducted during the course of developing embodiments for the present invention identified compounds capable of inhibiting ROCK activity (e.g., inhibiting ROCK1 and/or ROCK2 activity). In addition, experiments conducted during the course of developing embodiments for the present invention identified compounds as selective ROCK inhibitors (e.g., compounds that selectively inhibit ROCK1 activity over ROCK2 activity) (e.g., compounds that selectively inhibit ROCK2 activity over ROCK1 activity; see, e.g., compounds 1-5 as described in Table 1 and Example II). While not limited to the particular compounds, the present invention provides Rho kinase activity inhibiting compounds described by a formula selected from the group consisting of:

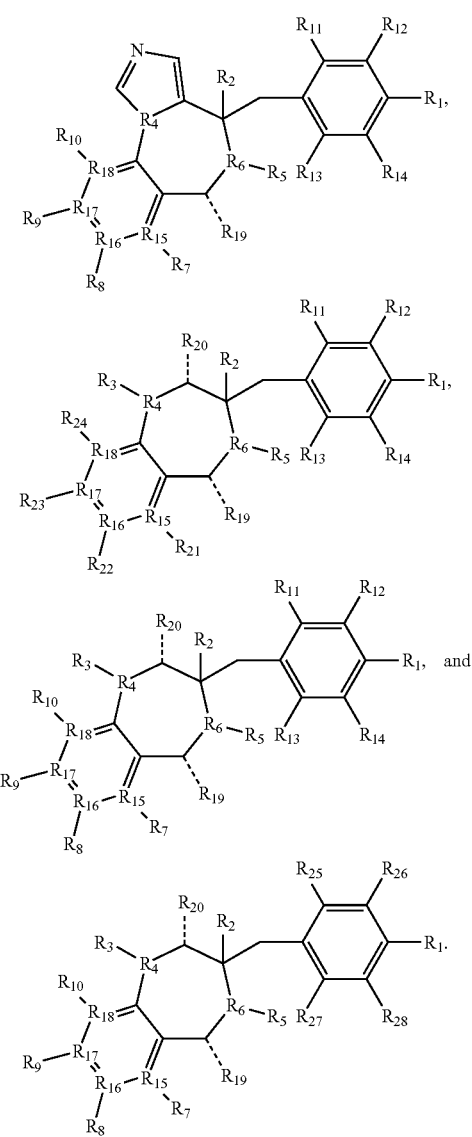

In some embodiments, R1 is a chemical group comprising at least two carbon molecules. In some embodiments, R1 is not pyridine.

In some embodiments, R1 is selected from the group consisting of: hydrogen, alkyl, substituted alkyl,

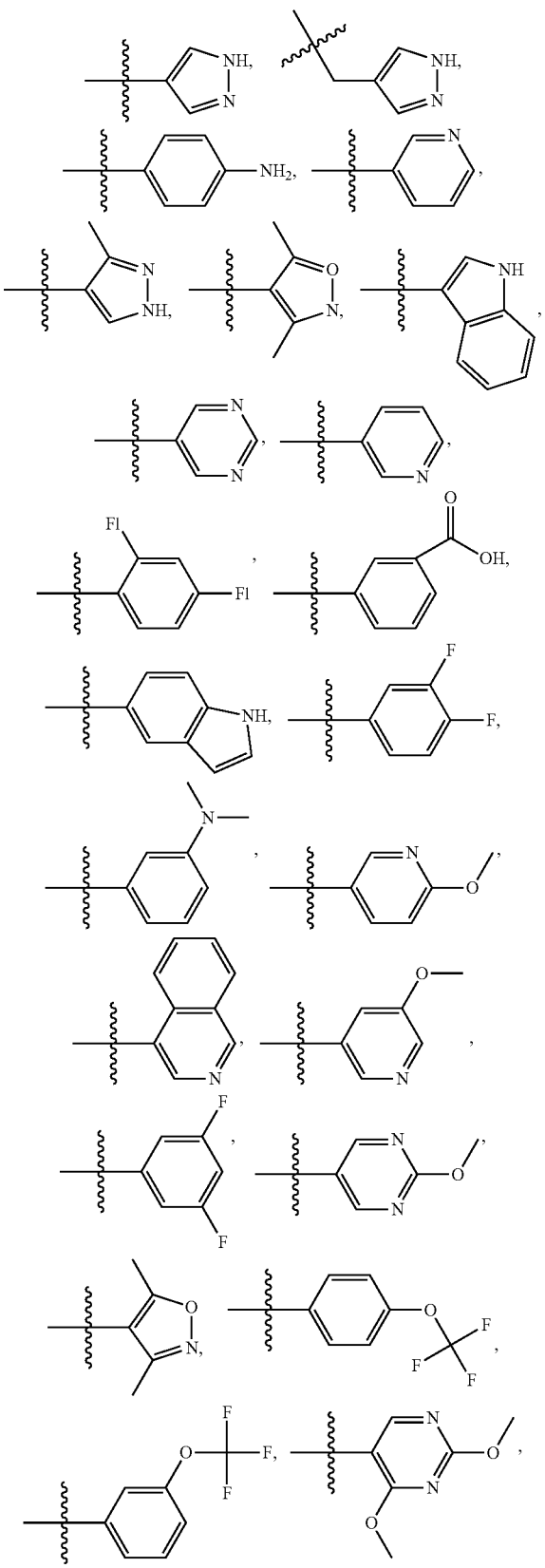

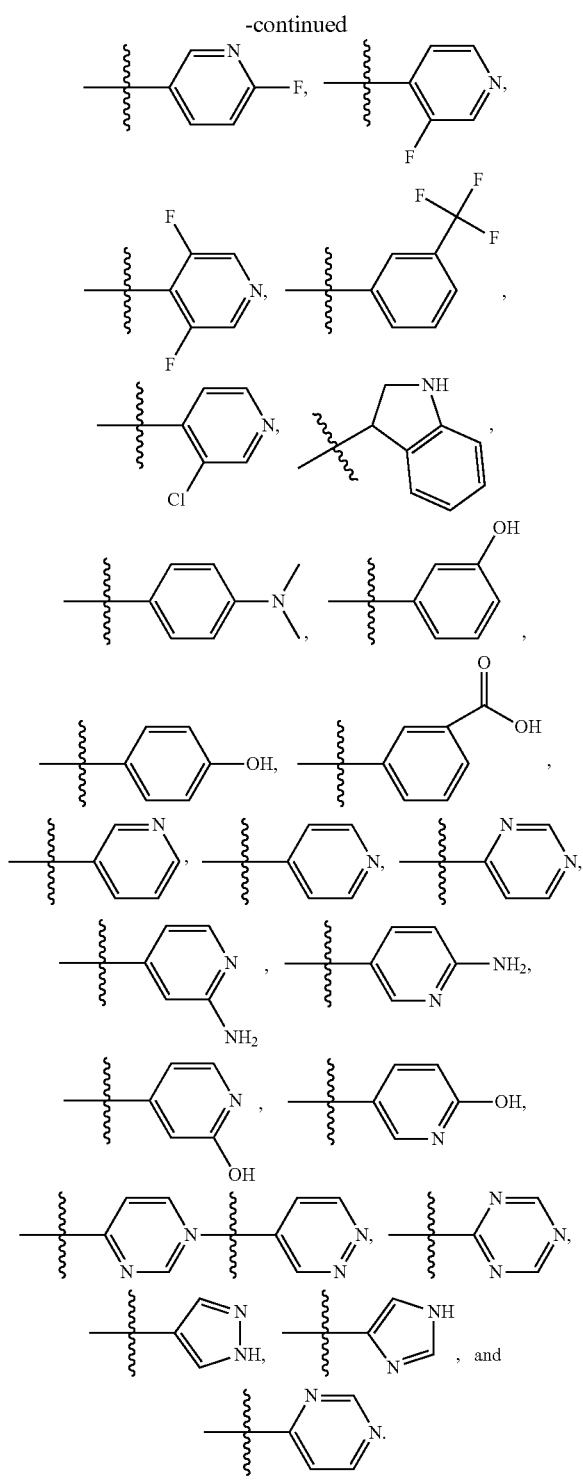

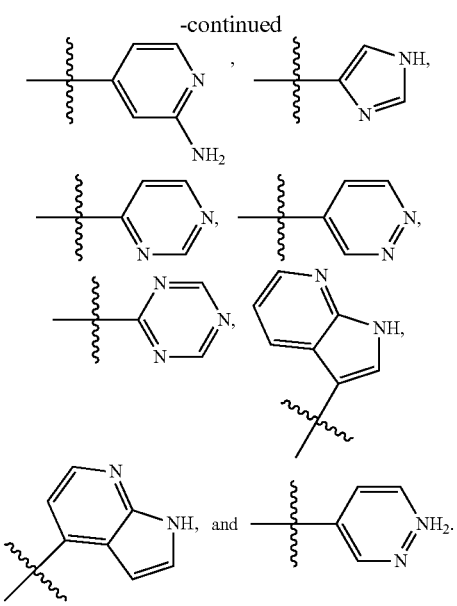

In some embodiments, $R_2$ is selected from the group consisting of H, alkyl, substituted alkyl, and $R_1$.

In some embodiments, $R_3$ is selected from the group consisting of H, alkyl (e.g., methyl, ethyl, hexyl, isopropyl), and substituted alkyl.

In some embodiments, R3 is selected from the group consisting of hydrogen; H; $CH_3$; ethyl; hexyl; isopropyl; halogen (e.g., fluorine, chlorine, bromine, iodine, astatine); OH; a chemical moiety comprising an aryl subgroup; a chemical moiety comprising a substituted aryl subgroup; a chemical moiety comprising a cycloaliphatic subgroup; a chemical moiety comprising a substituted cycloaliphatic subgroup; a chemical moiety comprising a heterocyclic subgroup; a chemical moiety comprising a substituted heterocyclic subgroup; a chemical moiety comprising at least one ester subgroup; a chemical moiety comprising at least one ether subgroup; a linear or branched, saturated or unsaturated, substituted or non-substituted, aliphatic chain having at least 2 carbons; a chemical moiety comprising Sulfur; a chemical moiety comprising Nitrogen; —OR—, wherein R is selected from the group consisting of a chemical moiety comprising an aryl subgroup; a chemical moiety comprising a substituted aryl subgroup; a chemical moiety comprising a cycloaliphatic subgroup; a chemical moiety comprising a substituted cycloaliphatic subgroup; a chemical moiety comprising a heterocyclic subgroup; a chemical moiety comprising a substituted heterocyclic subgroup; a linear or branched, saturated or unsaturated, substituted or non-substituted, aliphatic chain having at least 2 carbons; a chemical moiety comprising at least one ester subgroup; a chemical moiety comprising at least one ether subgroup; a chemical moiety comprising Sulfur; a chemical moiety comprising Nitrogen.

In some embodiments, the R1 and R3 groups may be interchanged (e.g., in some embodiments, the R1 group is positioned at the first position of the benzodiazepine ring and the R3 group is positioned at the third position of the benzodiazepine ring; in some embodiments, the R1 group is positioned at the third position of the benzodiazepine ring and the R3 group is positioned at the first position of the benzodiazepine ring).

In some embodiments, R4 is selected from the group consisting of C, N, S and O.

In some embodiments, R1' is selected from the group consisting of

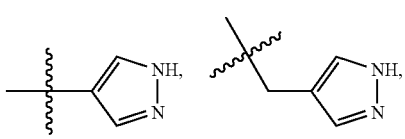

In some embodiments, R5 is selected from the group consisting of H, alkyl, substituted alkyl, mono-substituted aryl, di-substituted aryl, and tri-substituted aryl.

In some embodiments, R6 is selected from the group consisting of C, N, S and O.

In some embodiments, R7, R8, R9, and R10 are independently selected from the group consisting of being absent, H, halogen, CF3

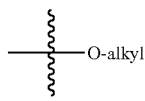

(e.g., substituted alkyl) (e.g., unsubstituted alkyl),

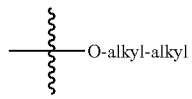

(e.g., substituted alkyl) (e.g., unsubstituted alkyl), OH, fluoroalkyl, sulfonamide, sulfone, $OCH_3$, $CH_3$, $SO_2R_{28}$, $SO_2N(R_{7'})_2$, $OR_{7'}$, $N(R_{7'})_2$, $CON(R_{7'})_2$, $NHCOR_{7'}$, $NHSO_2R_{7'}$, alkyl, mono-substituted alkyl, di-substituted alkyl, tri-substituted alkyl; wherein $R_{7'}$ is selected from the group consisting of halogen, H, alkyl, mono-substituted alkyl, di-substituted alkyl, tri-substituted alkyl, aryl, mono-substituted aryl, di-substituted aryl, tri-substituted aryl, cycloalipathic, mono-substituted cycloalipathic, di-substituted cycloalipathic, and tri-substituted cycloalipathic.

In some embodiments, R11, R12, R13, and R14, are independently selected from the group consisting of H, alkyl (e.g., substituted alkyl) (e.g., unsubstituted alkyl), fluoroalkyl,

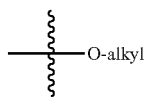

(e.g., substituted alkyl) (e.g., unsubstituted alkyl), aminoalkyl,

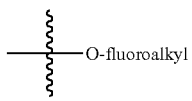

(e.g., substituted alkyl) (e.g., unsubstituted alkyl),

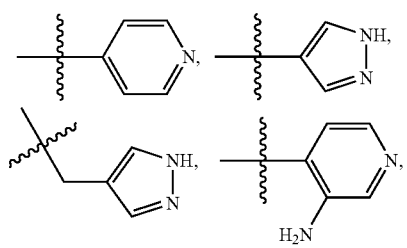

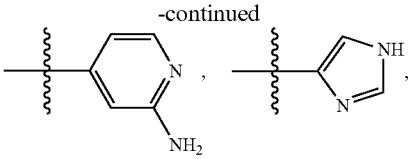

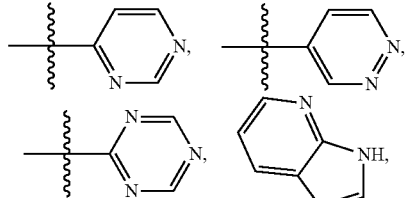

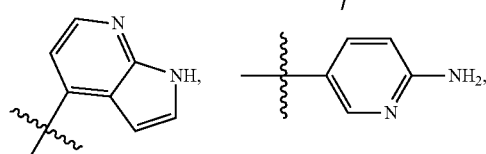

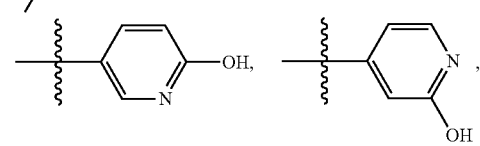

and substituted and unsubstituted, and derivatives thereof.

In some embodiments, R15, R16, R17, and R18 are independently selected from the group consisting of C, N, O, and S.

In some embodiments, R19 is selected from the group consisting of H, alkyl (e.g., substituted alkyl) (unsubstituted alkyl), ketone, a chemical moiety (e.g., substituted alkyl) (unsubstituted alkyl) comprising nitrogen, a chemical moiety (e.g., substituted alkyl) (unsubstituted alkyl) comprising oxygen, and a chemical moiety (e.g., substituted alkyl) (unsubstituted alkyl) comprising sulfur.

In some embodiments, R20 is selected from the group consisting of H, alkyl (e.g., substituted alkyl) (unsubstituted alkyl), ketone, a chemical moiety (e.g., substituted alkyl) (unsubstituted alkyl) comprising nitrogen, a chemical moiety (e.g., substituted alkyl) (unsubstituted alkyl) comprising oxygen, and a chemical moiety (e.g., substituted alkyl) (unsubstituted alkyl) comprising sulfur.

In some embodiments, R21, R22, R23, and R24 are independently selected from the group consisting of being absent, H, halogen, CF3,

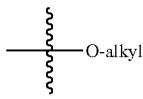

(e.g., substituted alkyl) (e.g., unsubstituted alkyl),

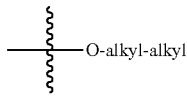

(e.g., substituted alkyl) (e.g., unsubstituted alkyl), OH, fluoroalkyl, sulfonamide, sulfone, $OCH_3$, $CH_3$, $SO_2R_{7'}$, $SO_2N$ (R7')2, OR7', N(R7')2, CON(R7')2, NHCOR7', NHSO2R7', alkyl, mono-substituted alkyl, di-substituted alkyl, tri-substituted alkyl; wherein R7' is selected from the group consisting of halogen, H, alkyl, mono-substituted alkyl, di-substituted alkyl, tri-substituted alkyl, aryl, mono-substituted aryl, di-substituted aryl, tri-substituted aryl, cycloalipathic, mono-substituted cycloalipathic, di-substituted cycloalipathic, and tri-substituted cycloalipathic; wherein no more than two of R21, R22, R23 and R24 can be hydrogen.

In some embodiments, R25, R26, R27, and R28, are independently selected from the group consisting of hydrogen, alkyl (e.g., substituted alkyl) (e.g., unsubstituted alkyl), fluoroalkyl,

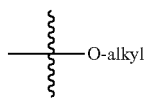

(e.g., substituted alkyl) (e.g., unsubstituted alkyl), aminoalkyl,

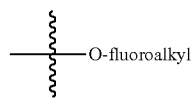

(e.g., substituted alkyl) (e.g., unsubstituted alkyl),

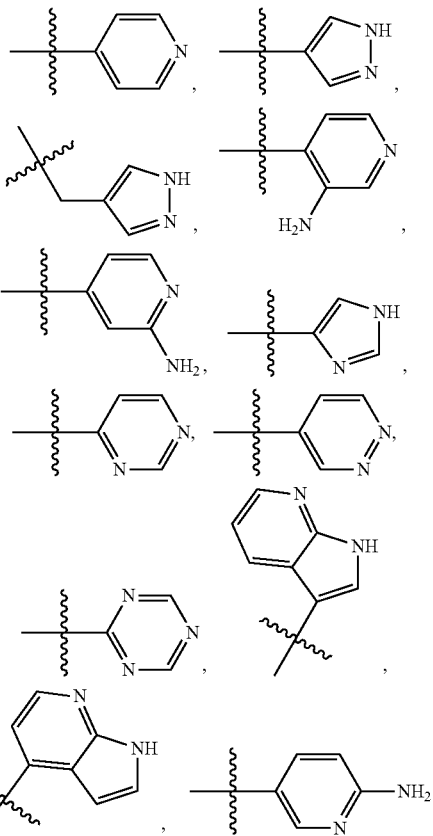

-continued

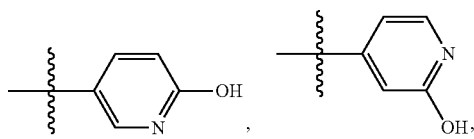

and substituted and unsubstituted, and derivatives thereof; wherein no more than three of R25, R26, R27 and R28 can be hydrogen.

In some embodiments, the formula is selected from the group consisting of:

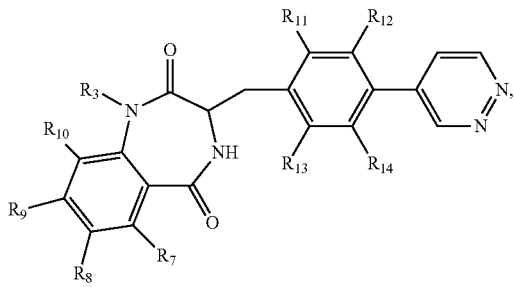

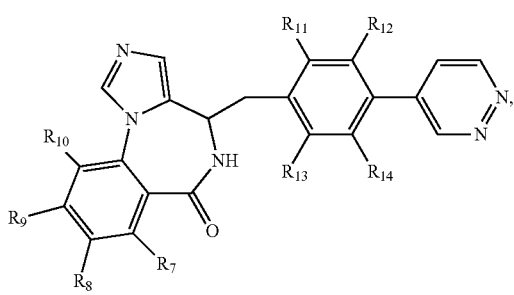

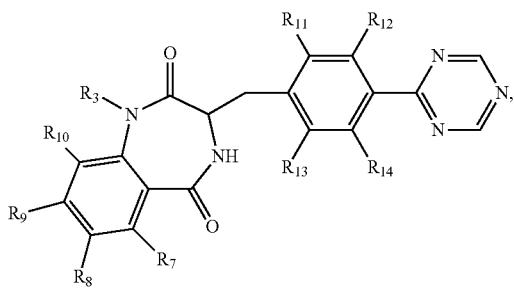

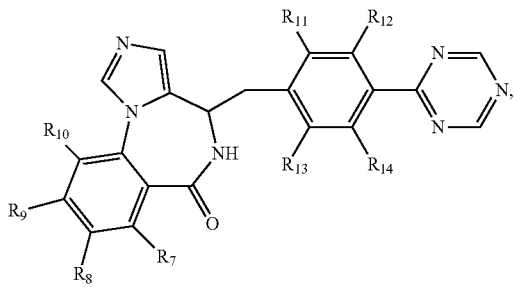

51
-continued
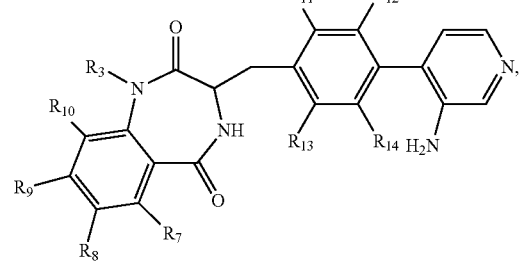
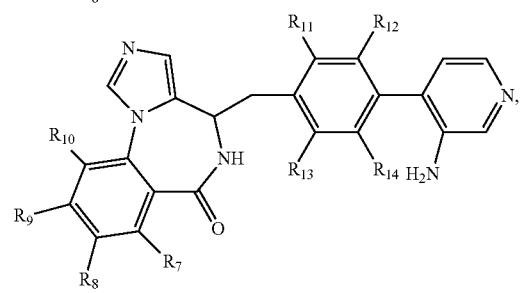
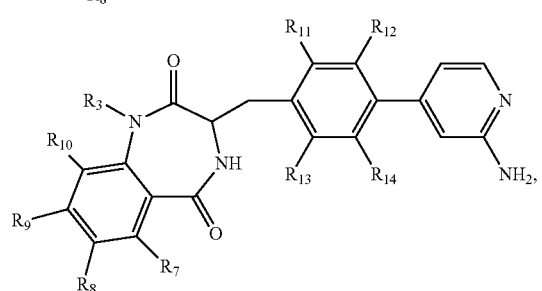
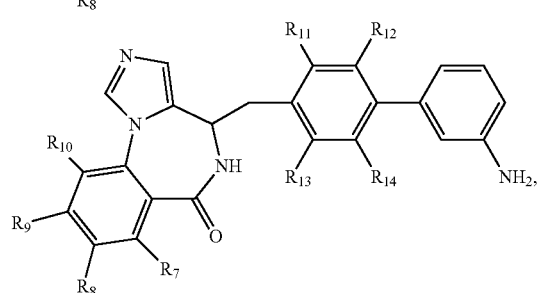
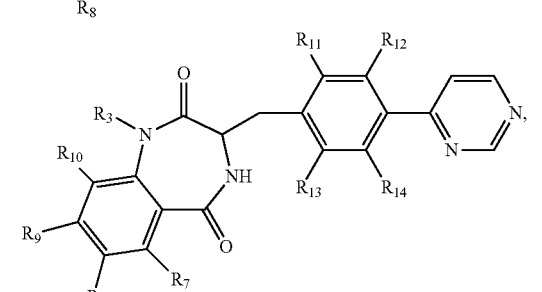
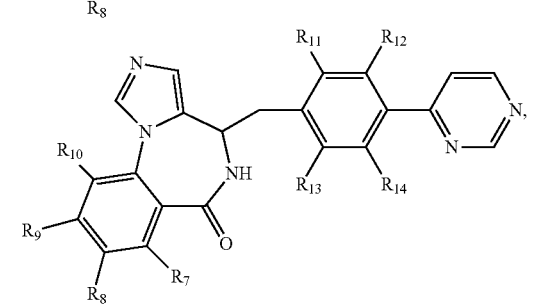
52
-continued
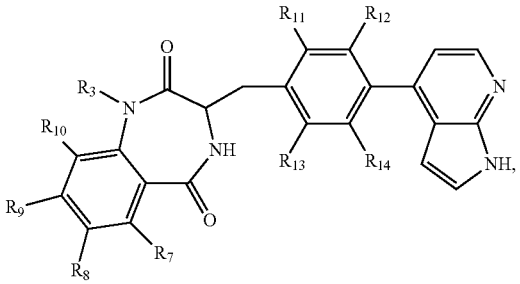
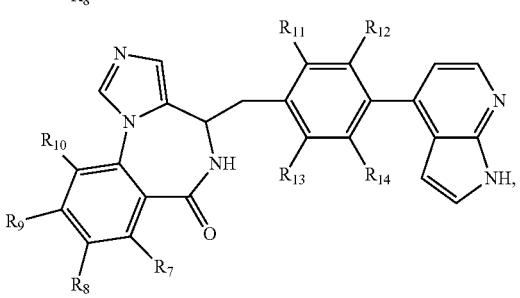
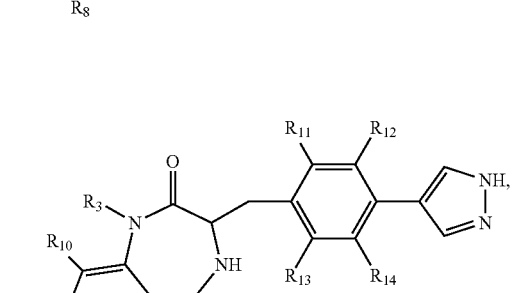
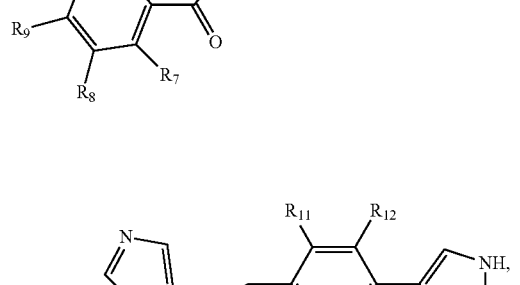
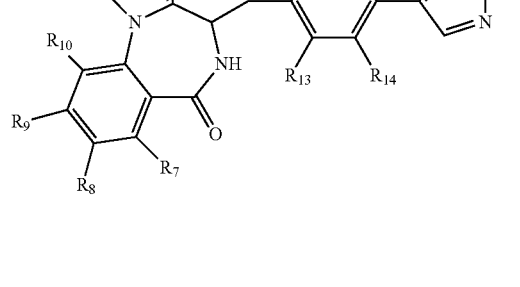
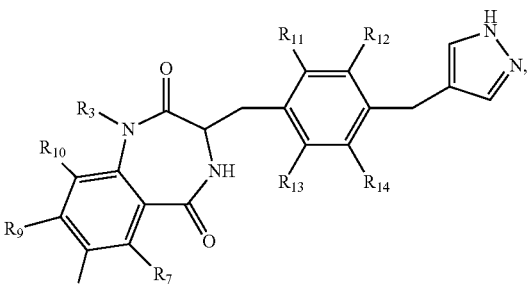

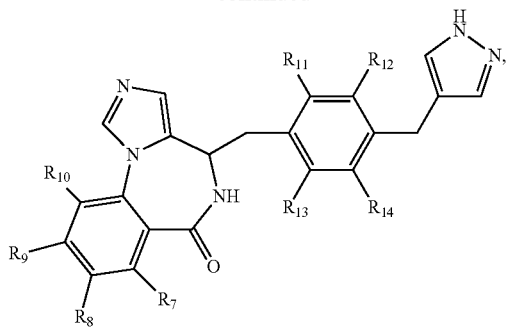
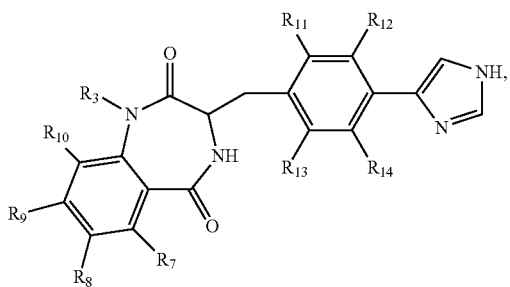
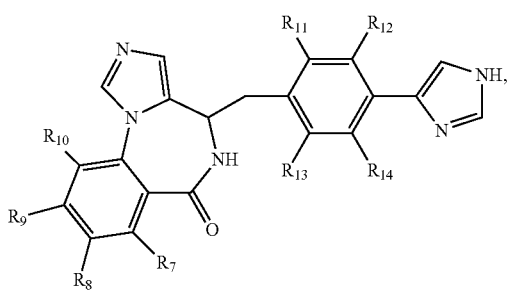
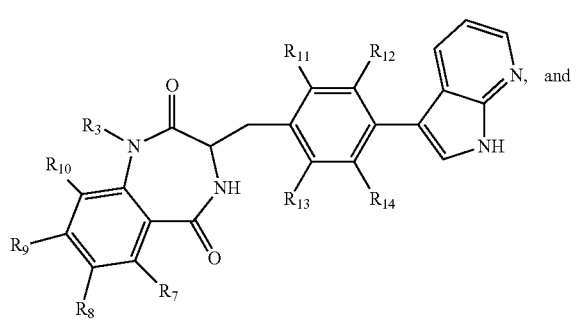
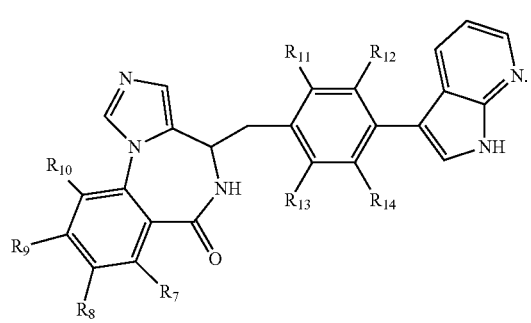
Certain compounds of the present invention include, but are not limited to,
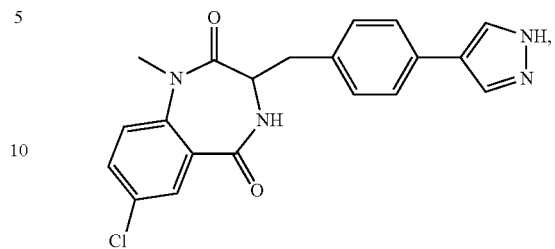
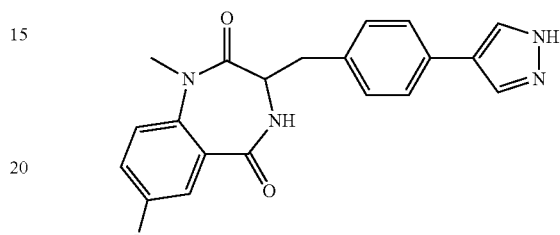
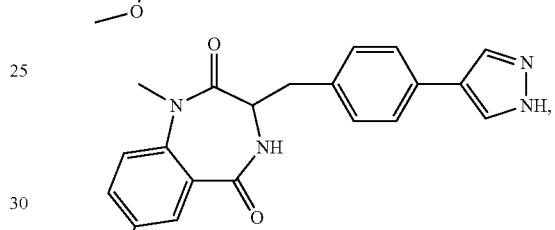
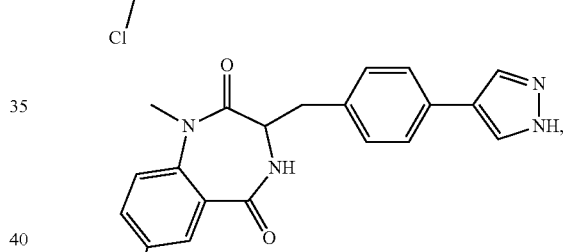
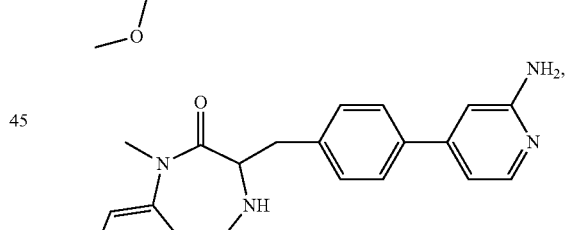
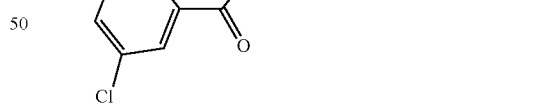
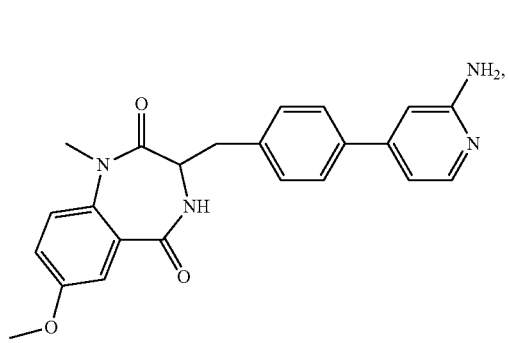

55
-continued
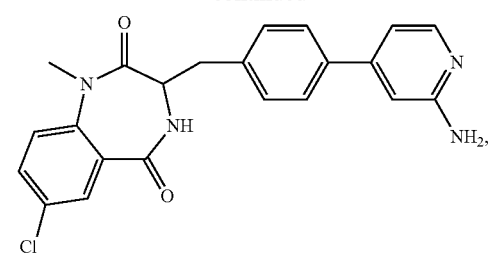
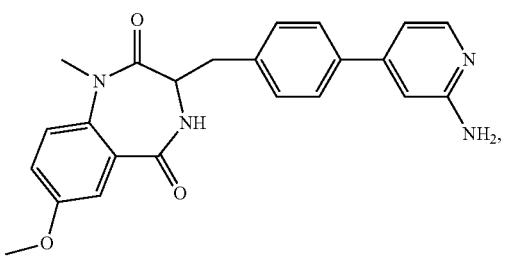
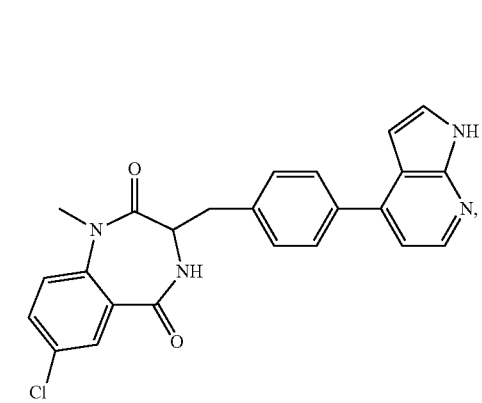
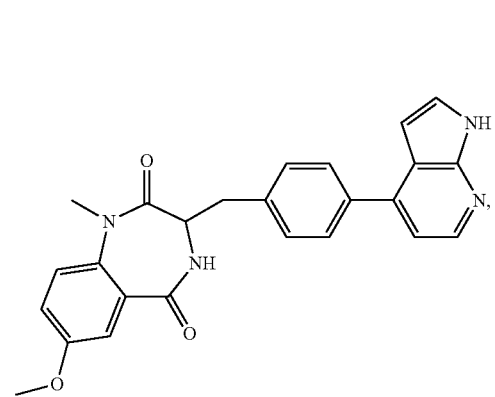
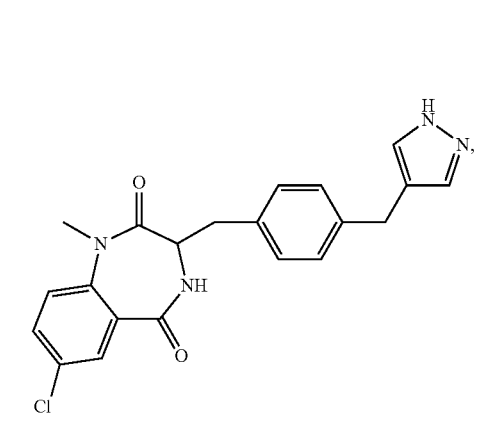
56
-continued
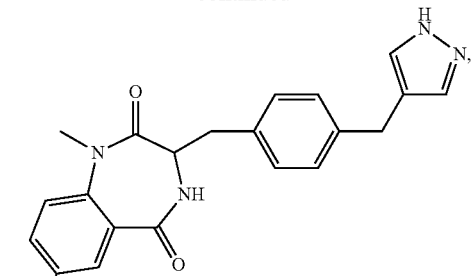
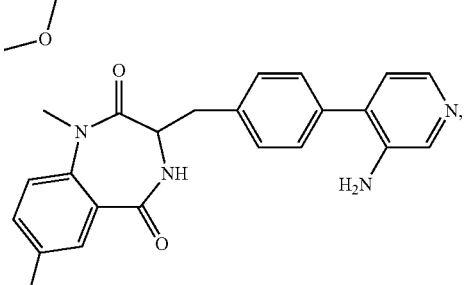
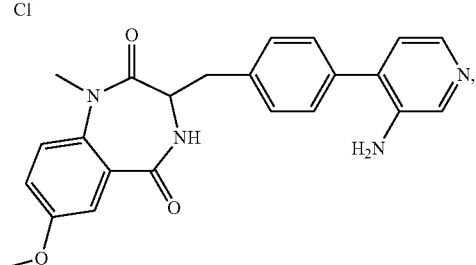
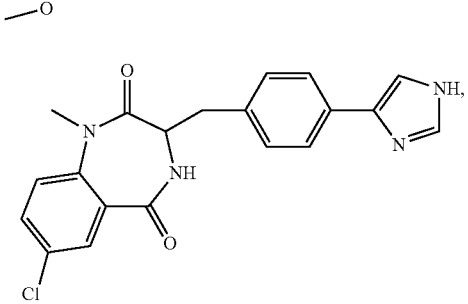
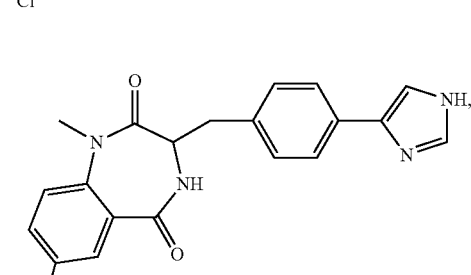
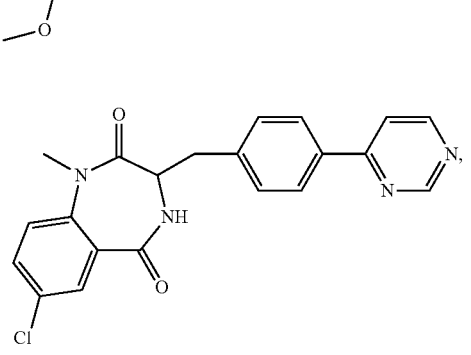

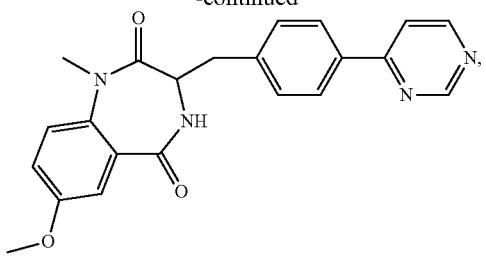
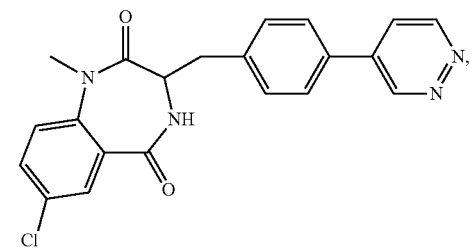
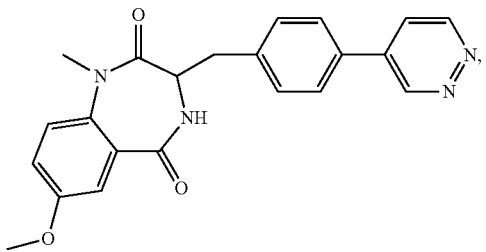
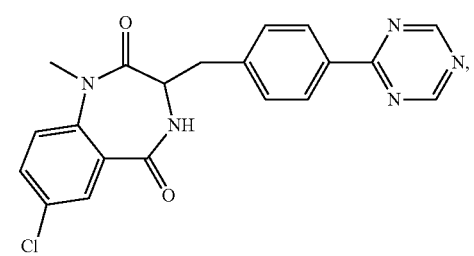
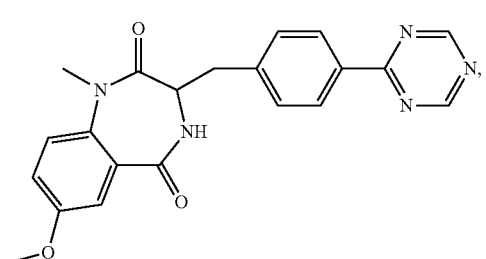
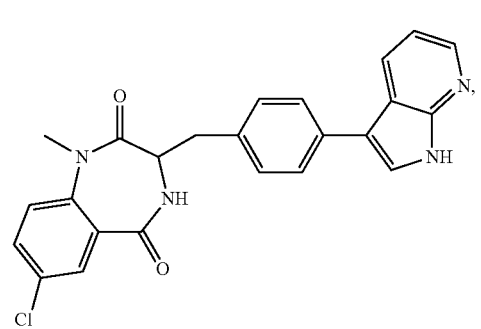
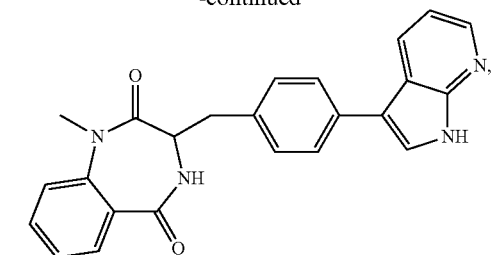
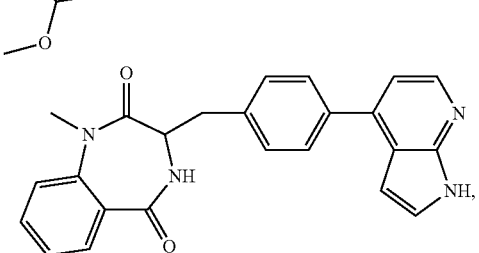
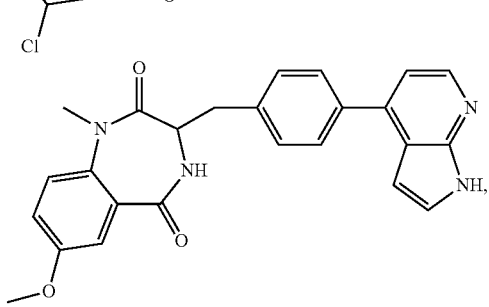
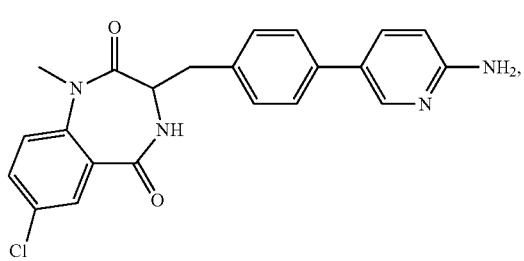
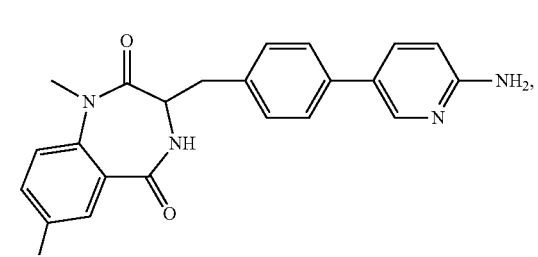
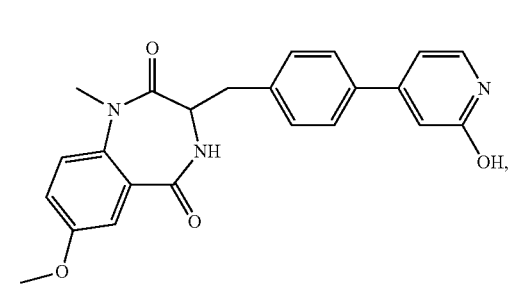

59
-continued
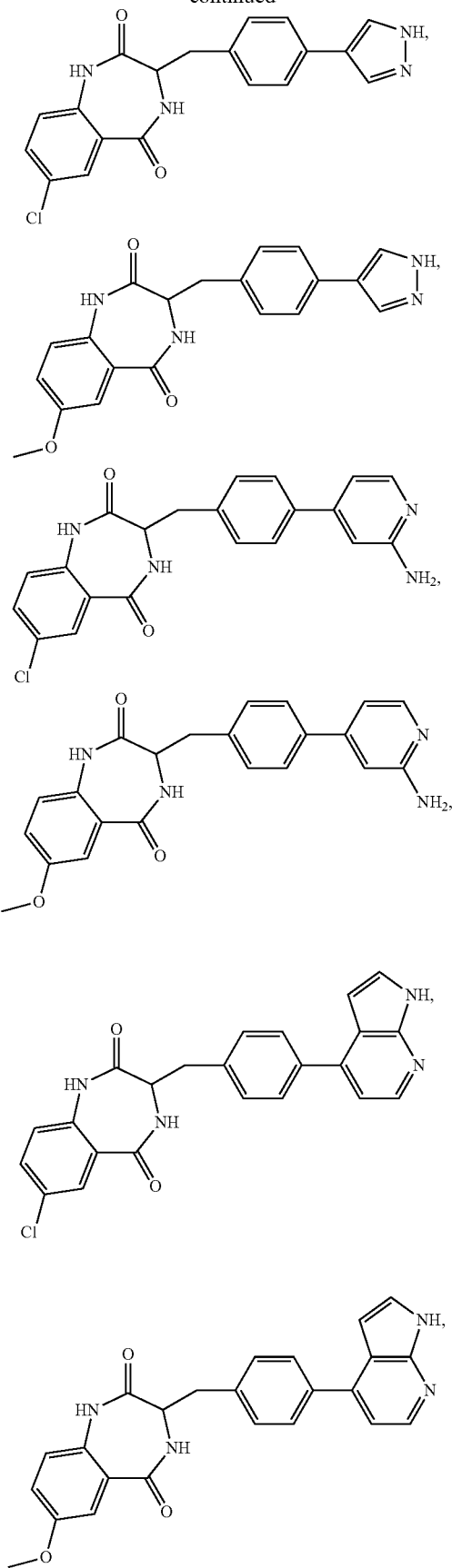
60
-continued
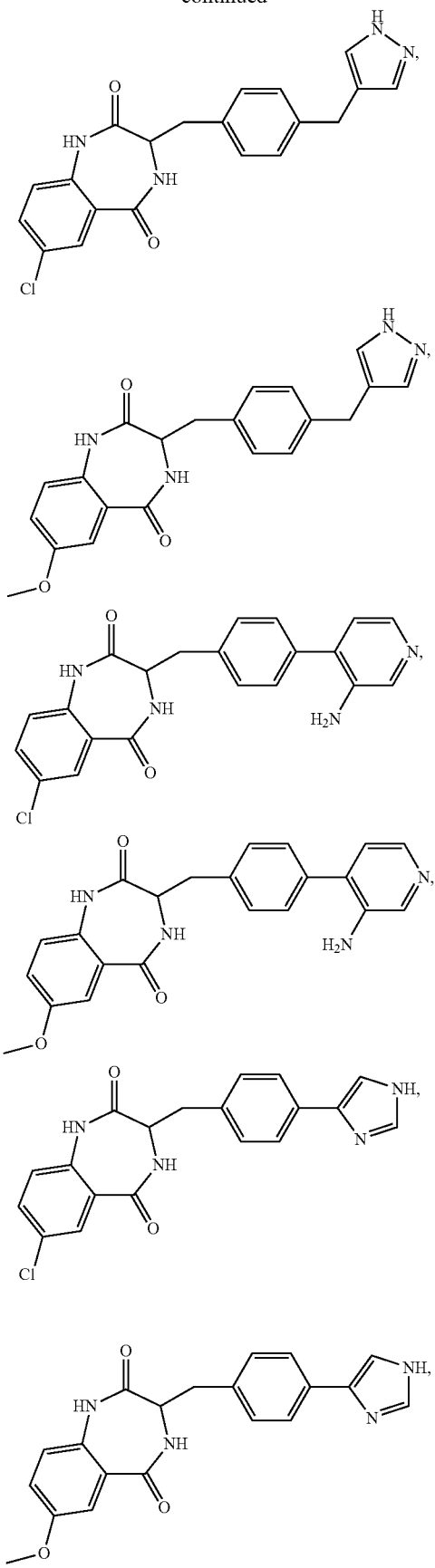

61
-continued
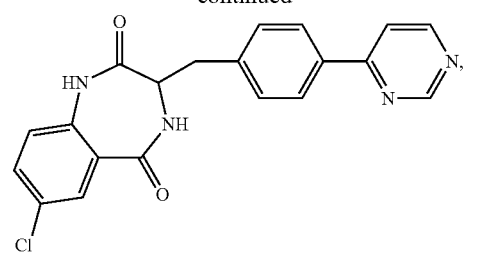
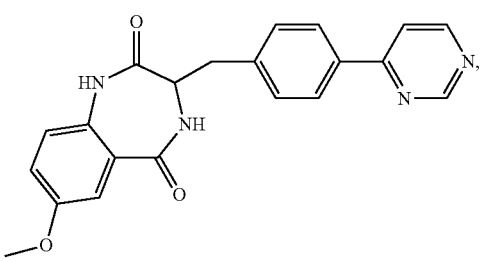
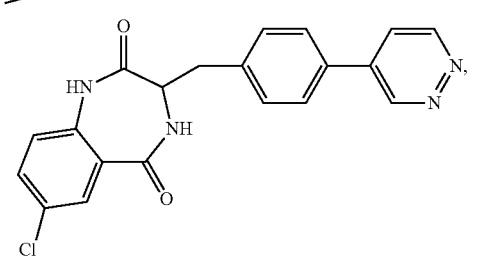
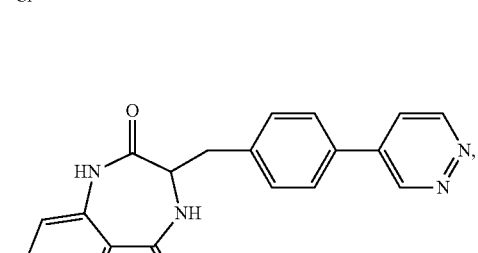
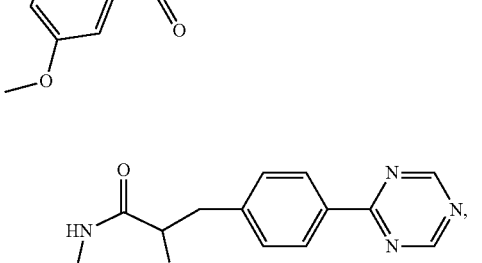
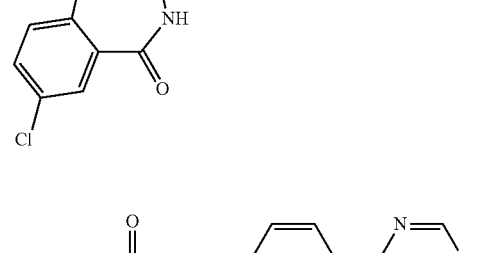
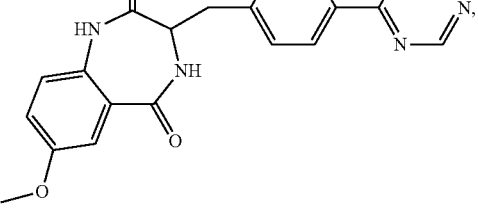
62
-continued
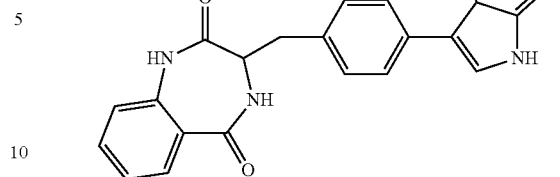
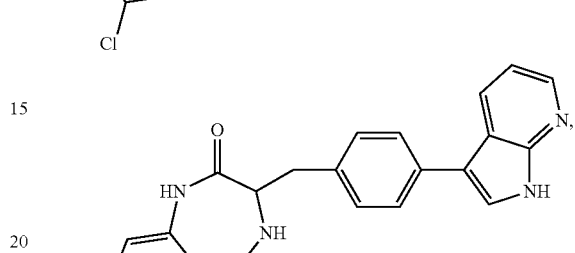
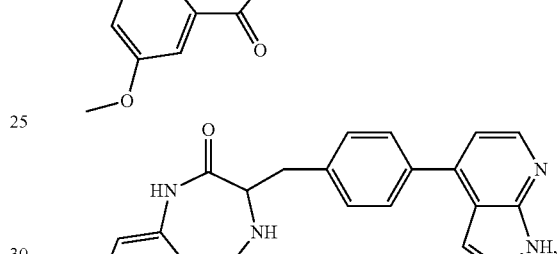
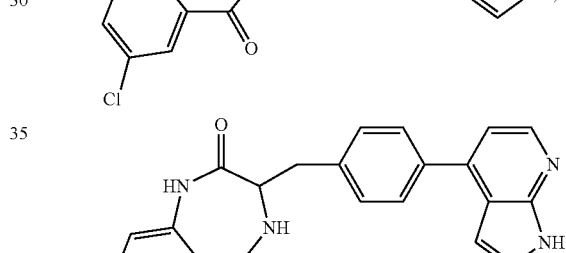
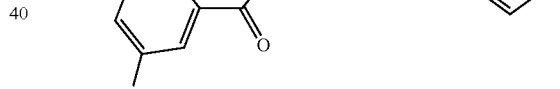
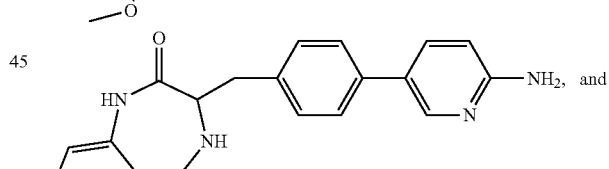
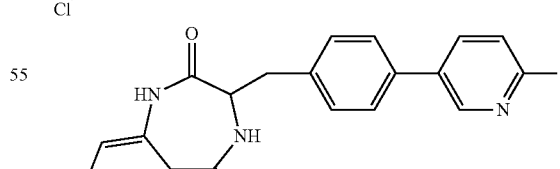
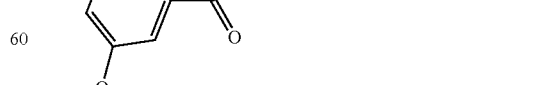
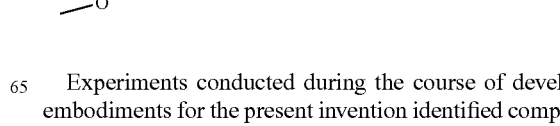
Experiments conducted during the course of developing embodiments for the present invention identified compounds that selectively inhibit ROCK2 activity over ROCK1 (see, e.g., Table 1 and Example II). As such, the present invention provides the following compounds that selectively ROCK2 activity over ROCK1:

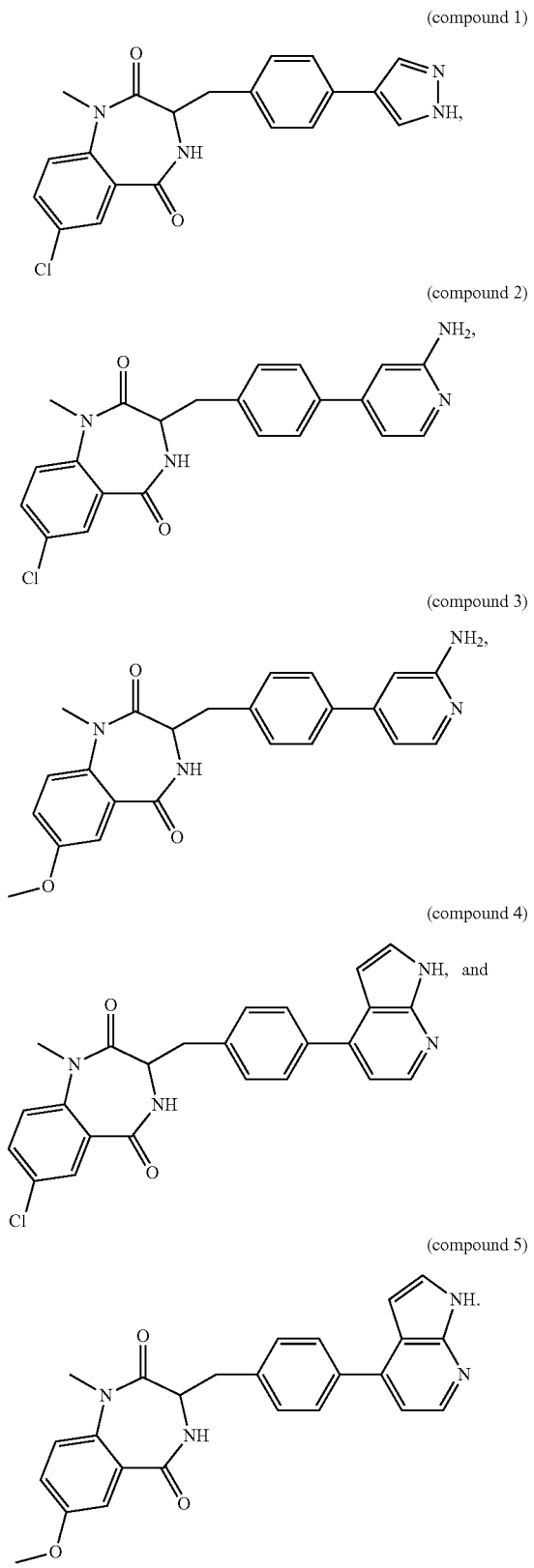

(compound 1)

(compound 2)

(compound 3)

(compound 4)

(compound 5)

From the above description, it is apparent that many specific examples are represented by the generic formulas presented above. A wide variety of sub combinations arising from selecting a particular group at each substituent position are possible and all such combinations are within the scope of this invention. The experimental examples, provided below, describe biological activities of these compounds and provide assays for assessing activities of derivatives or other related compounds.

In summary, a large number of compounds are presented herein. Any one or more of these compounds can be used to treat a variety of disorders related to ROCK activity as described elsewhere herein (e.g., cardiovascular disorders (e.g., angina (e.g., angina pectoris), atherosclerosis, stroke, cerebrovascular disease (e.g., cerebral thrombosis, cerebral embolism, and cerebral hemorrhage), congestive heart failure, coronary artery disease, myocardial infarction, peripheral vascular disease, stenosis (e.g., coronary artery stenosis, aortic stenosis, restenosis, pulmonary stenosis), vasospasm (e.g., cerebral artery vasospasm, coronary artery vasospasm), hypertension (e.g., pulmonary artery hypertension, systemic arterial hypertension)), smooth muscle related disorders (e.g., glaucoma, erectile dysfunction, bronchial asthma), granulomatosus disorders (e.g., sarcoidosis, Wegener's granulomatosus), acute macrophage-mediated diseases (e.g., adult respiratory distress syndrome), and autoimmune disorders (e.g., rheumatoid arthritis, systemic lupus erythematosus, multiple sclerosis, irritable bowel syndrome, and systemic sclerosis)). Additionally, any one or more of these compounds can be used in combination with at least one other therapeutic agent (e.g., potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, and vasopepsidase inhibitors, or an antiplatelet agent selected from GPIIb/IIIa blockers, $P2Y_1$ and $P2Y_{12}$ antagonists, thromboxane receptor antagonists, and aspirin) along with a pharmaceutically-acceptable carrier or diluent in a pharmaceutical composition. The above-described compounds can also be used in drug screening assays and other diagnostic and research methods.

III. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat a variety of conditions associated with ROCK activity (e.g., cardiovascular diseases, cancer, neurological diseases, renal diseases, bronchial asthma, erectile dysfunction, and glaucoma). In addition, the compounds are also useful for preparing medicaments for treating other disorders wherein the effectiveness of the compounds are known or predicted. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In preferred embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In preferred embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer therapeutic agents (e.g., exemplary compounds as described in Section I above) of the present invention, e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To identify patients that can be beneficially treated, a tissue sample is removed from the patient and the cells are assayed for sensitivity to the agent. Therapeutic amounts are empirically determined and vary with the pathology being treated, the subject being treated and the efficacy and toxicity of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is cancer, the additional agent can be a chemotherapeutic agent or radiation. When the condition being treated is an autoimmune disorder, the additional agent can be an immunosuppressant or an anti-inflammatory agent. When the condition being treated is chronic inflammation, the additional agent can be an anti-inflammatory agent. The additional agents to be co-administered, such as anticancer, immunosuppressant, anti-inflammatory, and can be any of the well-known agents in the art, including, but not limited to, those that are currently in clinical use. The determination of appropriate type and dosage of radiation treatment is also within the skill in the art or can be determined with relative ease.

III. Drug Screens

In some embodiments of the present invention, the compounds of the present invention, and other potentially useful compounds, are screened for ROCK modulating (e.g., activating, inhibiting) activity. In some embodiments of the present invention, the compounds of the present invention, and other potentially useful compounds, are screened for ROCK modulating (e.g., activating, inhibiting) activity through assessment of pro-inflammatory cytokine activity (e.g., IL-17 and/or IL-21, and/or pathways related to pro-inflammatory cytokine activity (eg., IRF-4)).

A number of suitable screens for measuring the binding affinity of drugs and other small molecules to receptors are known in the art. In some embodiments, binding affinity screens are conducted in in vitro systems. In other embodiments, these screens are conducted in in vivo or ex vivo systems.

IV. Therapeutic Application

In particularly preferred embodiments, the compositions of the present invention are contemplated to provide therapeutic benefits to patients suffering from any one or more of a number of conditions associated with ROCK activity (e.g., cardiovascular diseases, cancer, neurological diseases, renal diseases, bronchial asthma, erectile dysfunction, and glaucoma) by modulating (e.g., inhibiting or promoting) ROCK activity in affected cells or tissues. In further preferred embodiments, the compositions of the present invention are used to treat conditions and/or disorders associated with ROCK activity (e.g., cardiovascular diseases, cancer, neurological diseases, renal diseases, bronchial asthma, erectile dysfunction, and glaucoma).

In certain embodiments, the present invention provides methods (e.g., therapeutic applications) for regulating inhibiting Rho kinase activity comprising: a) providing: i. target cells having Rho kinase activity; and ii. a composition (e.g., exemplary compounds as described in Section I above); and b) exposing the target cells to the composition under conditions such that the exposure results in inhibition (e.g., reduction, cessation) of Rho kinase activity. The methods of the present invention are not limited to particular target cells. In some embodiments, the target cells are selected from the group consisting of in vitro cells, in vivo cells, ex vivo cells, smooth muscle cells, non-smooth muscle cells, and cancer cells. The present invention is not limited to a particular therapeutic application.

In some embodiments, the compositions of the present invention are contemplated to provide therapeutic benefits to patients suffering from any one or more of a number of conditions associated with aberrant ROCK activity (e.g., cardiovascular disorders (e.g., angina (e.g., angina pectoris), atherosclerosis, stroke, cerebrovascular disease (e.g., cerebral thrombosis, cerebral embolism, and cerebral hemorrhage), congestive heart failure, coronary artery disease, myocardial infarction, peripheral vascular disease, stenosis (e.g., coronary artery stenosis, aortic stenosis, restenosis, pulmonary stenosis), vasospasm (e.g., cerebral artery vasospasm, coronary artery vasospasm), hypertension (e.g., pulmonary artery hypertension, systemic arterial hypertension)), smooth muscle related disorders (e.g., glaucoma, erectile dysfunction, bronchial asthma), granulomatosus disorders (e.g., sarcoidosis, Wegener's granulomatosus), acute macrophage-mediated diseases (e.g., adult respiratory distress syndrome), and autoimmune disorders (e.g., rheumatoid arthritis, systemic lupus erythematosus, multiple sclerosis, irritable bowel syndrome, and systemic sclerosis)) by modulating (e.g., inhibiting or promoting) the activity of ROCK in affected cells or tissues.

In some embodiments, the condition associated with aberrant ROCK activity is related to pro-inflammatory cytokine expression (e.g., IL-17 and/or IL-21) (e.g., pathways related to IL-17 and/or IL-21 expression (e.g., IRF4)) (e.g., inflammatory disorders). For example, it has been demonstrated that inhibition of ROCK2 results in inhibited expression of pro-inflammatory cytokines (e.g., IL-17 and/or IL-21) (see, e.g., Biswas, et al., J. Clin. Inv. 2010, 120(9), 3280-3295; herein incorporated by reference in its entirety). Accordingly, in some embodiments, pro-inflammatory cytokine expression (e.g., IL-17 and/or IL-21) (e.g., pathways related to IL-17 and/or IL-21 expression (e.g., IRF4)) inihibition is accomplished through use of any of the compounds of the present invention that selectively inhibits ROCK2 activity over ROCK1 (see, e.g., compounds 1-5 as shown in Table 1 and Example II). The methods are not limited to a particular manner of pro-inflammatory cytokine expression (e.g., IL-17 and/or IL-21) (e.g., pathways related to IL-17 and/or IL-21 expression (e.g., IRF4)) inihibition. For example, in some embodiments, pro-inflammatory cytokine expression (e.g., IL-17 and/or IL-21) inihibition is achieved through inhibition of ROCK2 which, for example, thereby inhibits IRF4 expression (e.g., through prevention of IRF4 phosphorylation) which, for example, inhibits IL17 and/or IL-21 expression.

In some embodiments, the compositions of the present invention provide methods for treating a subject with a disorder and/or condition associated with aberrant ROCK activity. In some embodiments, the methods involve administering to a subject suffering from a disorder and/or condition associated with aberrant ROCK activity a ROCK inhibitor of the present invention (e.g., a compound described in Section I) under conditions such that ROCK activity is modulated (e.g., increased or diminished).

The present invention is not limited to treating particular disorders and/or conditions associate with aberrant ROCK activity. In certain embodiments, said compounds find use in treating acute and chronic pain and inflammation. For example, the compounds of the present invention find use in treating subjects with neuropathy, neuropathic pain, or inflammatory pain such as reflex sympathetic dystrophy/causalgia (nerve injury), peripheral neuropathy (including diabetic neuropathy), intractable cancer pain, complex regional pain syndrome, and entrapment neuropathy (carpel tunnel syndrome). The compounds may also be useful in the treatment of pain associated with acute herpes zoster (shingles), postherpetic neuralgia (PHN), and associated pain syndromes such as ocular pain. The compounds may further be useful as analgesics in the treatment of pain such as surgical analgesia, or as an antipyretic for the treatment of fever. Pain indications include, but are not limited to, post-surgical pain for various surgical procedures including post-cardiac surgery, dental pain/dental extraction, pain resulting from cancer, muscular pain, mastalgia, pain resulting from dermal injuries, lower back pain, headaches of various etiologies, including migraine, and the like. The compounds may also be useful for the treatment of pain-related disorders such as tactile allodynia and hyperalgesia. The pain may be somatogenic (either nociceptive or neuropathic), acute and/or chronic. The compounds of the present invention may also be useful in conditions where NSAIDs, morphine or fentanyl opiates and/or other opioid analgesics would traditionally be administered.

In some embodiments, the compounds of the present invention are used in the treatment or prevention of opiate tolerance in subjects needing, for example, protracted opiate analgesics, and benzodiazepine tolerance in patients taking benzodiazepines, and other addictive behavior, for example, nicotine addiction, alcoholism, and eating disorders. Moreover, the compounds and methods of the present invention are used in the treatment or prevention of drug withdrawal symptoms, for example treatment or prevention of symptoms of withdrawal from opiate, alcohol, or tobacco addiction.

In some embodiments, the compounds of the present invention are used to treat insulin resistance and other metabolic disorders such as atherosclerosis that are typically associated with an exaggerated inflammatory signaling.

In some embodiments, the compounds of the present invention are used to treat or prevent respiratory disease or conditions, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; asthma-related diseases such as airway hyperreactivity and small airway disease; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchiolitis, bronchioectasis, cystic fibrosis, pigeon fancier's disease, farmer's lung, acute respiratory distress syndrome, pneumonia, pneumonitis, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus, hypoxia, dyspnea, hypercapnea, hyperinflation, hypoxemia, and cough. Further, the compounds of the present invention find use in the treatment of allergic disorders such as delayed type hypersensitivity reaction, allergic contact dermatitis, allergic rhinitis, and chronic sinusitis.

Other disorders or conditions which may be treated by the compounds of the present invention include inflammation and related disorders. For example, the compounds are used to treat arthritis, including but not limited to rheumatoid arthritis, spondyloarthropathies, gouty arthritis, osteoarthritis, juvenile arthritis, acute rheumatic arthritis, enteropathic arthritis, neuropathic arthritis, psoriatic arthritis, reactive arthritis (Reiter's syndrome), and pyogenic arthritis, and autoimmune diseases, including systemic lupus erythematosus, hemolytic syndromes, autoimmune hepatitis, autoimmune neuropathy, vitiglio (autoimmune thyroiditis), Hashimoto's thyroiditis, anemias, myositis including polymyositis, alopecia greata, Goodpasture's syndrome, hypophytis, and pulmonary fibrosis.

In some embodiments, the compounds are used in treating osteoporosis and other related bone disorders.

In some embodiments, the compounds of the present invention are used to treat gastrointestinal conditions such as reflux esophagitis, diarrhea, inflammatory bowel disease, Crohn's disease, gastritis, irritable bowel syndrome, Graves' disease (hyperthyroidism), necrotizing enterocolitis, and ulcerative colitis. The compounds may also be used in the treatment of pulmonary inflammation, such as that associated with viral infections and cystic fibrosis.

In some embodiments, the compounds of the present invention are used treating organ transplant patients either alone or in combination with conventional immunomodulators. Examples of conditions to be treated in said patients include graft vs. host reaction (i.e., graft vs. host disease), allograft rejections (e.g., acute allograft rejection, and chronic allograft rejection), transplant reperfusion injury, and early transplantation rejection (e.g., acute allograft rejection).

In some embodiments, the compounds of the present invention are used in the treatment of pruritis and vitaligo.

In some embodiments, the compounds of the present invention are used in treating tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Langerhans' cell histiocytosis, glomerulonephritis, reperfusion injury, pancreatitis, interstitial cystitis, Behcet's syndrome, polymyositis, gingivitis, periodontis, hypersensitivity, swelling occurring after injury, ischemias including myocardial ischemia, cardiovascular ischemia, and ischemia secondary to cardiac arrest, cirrhosis, septic shock, endotoxic shock, gram negative sepsis, toxic shock syndrome, stroke, ischemia reperfusion injury, multiorgan dysfunction, restenosis including restenosis following coronary bypass surgery, and the like.

In some embodiments, the compounds of the present invention are used in the treatment of certain diseases and disorders of the nervous system. Central nervous system disorders in which Rho kinase inhibition may be useful include cortical dementias including Alzheimer's disease and mild cognitive impairment (MCI), central nervous system damage resulting from stroke, ischemias including cerebral ischemia (both focal ischemia, thrombotic stroke and global ischemia (for example, secondary to cardiac arrest), and trauma. Neurodegenerative disorders in which Rho kinase inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia (e.g. pre-senile dementia), and AIDS-related dementia, cachexia, Sydenham's chorea, Huntington's disease, Parkinson's Disease, amyotrophic lateral sclerosis (ALS), multiple sclerosis, Korsakoff's syndrome, and imbecility relating to a cerebral vessel disorder. Further disorders in which Rho kinase inhibition might prove useful include neuropathies of the central and peripheral nervous system (including, for example, IgA neuropathy, membranous neuropathy and idiopathic neuropathy), chronic inflammatory demyelinating polyneuropathy, transverse myelitis, Gullain-Barre disease, encephalitis, and cancers of the nervous system. Disorders of CNS function in which Rho kinase inhibitors may find use include sleeping disorders, schizophrenia, depression, depression or other symptoms associated with Premenstrual Syndrome (PMS), and anxiety.

Furthermore, the compounds of the present invention are used in inhibiting Rho kinase activity for the amelioration of systemic disorders including septic and/or toxic hemorrhagic shock induced by a wide variety of agents; as a therapy with cytokines such as TNF, IL-1 and IL-2; and as an adjuvant to short term immunosuppression in transplant therapy.

Still other disorders or conditions which may be treated by the compounds of the present invention include the prevention or treatment of cancer, such as colorectal cancer, and cancer of the breast, lung, prostate, bladder, cervix and skin. Compounds of the invention may be used in the treatment and prevention of neoplasias including but not limited to brain cancer, bone cancer, leukemia, lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present compounds and methods may also be used to treat the fibrosis which occurs with radiation therapy. The present compounds and methods may be used to treat subjects having adenomatous polyps, including those with familial adenomatous polyposis (FAP). Additionally, the present compounds and methods may be used to prevent polyps from forming in patients at risk of FAP.

In some embodiments, the compounds of the present invention are used in the treatment of ophthalmic diseases, such as dry eye, glaucoma, corneal neovascularization, optic neuritis, Sjogren's syndrome, retinal ganglion degeneration, ocular ischemia, retinitis, retinopathies, uveitis, ocular photophobia, and of inflammation and pain associated with acute injury to the eye tissue. In some embodiments, the compounds are used to treat glaucomatous retinopathy and/or diabetic retinopathy. In some embodiments, the compounds are used to treat post-operative inflammation or pain as from ophthalmic surgery such as cataract surgery and refractive surgery.

In some embodiments, the compounds of the present invention are used in the treatment of menstrual cramps, dysmenorrhea, premature labor, endometriosis, tendonitis, bursitis, skin-related conditions such as psoriasis, eczema, burns, sunburn, dermatitis, pancreatitis, hepatitis, lichen planus, scleritis, scleroderma, dermatomyositis, and the like. Other conditions in which the compounds of the present invention are used include diabetes (type I or type II), myocarditis, pathological angiogenesis, and aortic aneurysm.

Moreover, compounds of the present invention are used in the treatment of cardiovascular disease, such as angina, coronary artery vasospasm, myocardial infarction, coronary ischemia, congestive heart failure, cardiac allograft vasculopathy, vein graft disease and vascular restenosis, ischemic reperfusion injury, cerebral artery vasospasm, stroke, cerebral ischemia, essential hypertension, pulmonary hypertension, renal hypertension and other secondary hypertensive disorders, atherosclerosis and erectile dysfunction.

In some embodiments, the compounds of the present invention are used to treat autoimmune disorders. Examples of autoimmune disorders include, but are not limited to, rheumatoid arthritis, psoriasis, chronic graft-versus-host disease, acute graft-versus-host disease, Crohn's disease, multiple sclerosis, systemic lupus erythematosus, Celiac Sprue, idiopathic thrombocytopenic thrombotic purpura, myasthenia gravis, Sjogren's syndrome, scleroderma, or psoriatic epidermal hyperplasia. In certain other embodiments, the autoimmune disorder is psoriasis, chronic graft-versus-host disease, acute graft-versus-host disease, Crohn's disease, systemic lupus erythematosus, or psoriatic epidermal hyperplasia. In some embodiments, the autoimmune disorder is a type of psoriasis selected from the group consisting of plaque psoriasis, guttate psoriasis, inverse psoriasis, pustular psoriasis, and erythrodermic psoriasis. In some embodiments, the immune disorder is inflammatory bowel disease or ulcerative colitis. In some embodiments, the immune disorder is an immune disorder associated with or arising from activity of pathogenic lymphocytes. In some embodiments, the immune disorder is an immune disorder susceptible to treatment by administering to a patient with the immune disorder an active agent that inhibits mitochondrial respiration.

In some embodiments, the autoimmune disorder is arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, uveitis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, ploymyalgia rheumatica, sarcoidosis, sclerosis, primary biliary sclerosis, sclerosing cholangitis, dermatitis, atopic dermatitis, Still's disease, chronic obstructive pulmonary disease, Guillain-Barre disease, Graves' disease, Addison's disease, Raynaud's phenomenon, or autoimmune hepatitis.

In some embodiments, the compounds of the present invention are used to treat disorders related to pro-inflammatory cytokine expression (e.g., IL-17 and/or IL-21) (e.g., pathways related to IL-17 and/or IL-21 expression (e.g., IRF4)). In some embodiments, the disorder is an inflammatory disorder. Inflammatory disorders include but are not limited to arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis. In certain embodiments, disorders and/or conditions associated with aberrant ROCK activity include, but are not limited to, cardiovascular disorders (e.g., angina (e.g., angina pectoris), atherosclerosis, stroke, cerebrovascular disease (e.g., cerebral thrombosis, cerebral embolism, and cerebral hemorrhage), congestive heart failure, coronary artery disease, myocardial infarction, peripheral vascular disease, stenosis (e.g., coronary artery stenosis, aortic stenosis, restenosis, pulmonary stenosis), vasospasm (e.g., cerebral artery vasospasm, coronary artery vasospasm), hypertension (e.g., pulmonary artery hypertension, systemic arterial hypertension)), smooth muscle related disorders (e.g., glaucoma, erectile dysfunction, bronchial asthma), granulomatosus disorders (e.g., sarcoidosis, Wegener's granulomatosus), acute macrophage-mediated diseases (e.g., adult respiratory distress syndrome), and autoimmune disorders (e.g., rheumatoid arthritis, systemic lupus erythematosus, multiple sclerosis, irritable bowel syndrome, and systemic sclerosis).

In some embodiments, the composition comprising a ROCK inhibitor of the present invention is co-administered with an agent configured to treat angina (e.g., antiplatelet agents (e.g., aspirin, ticlopidine, clopidogrel), beta-andrenergic blocking agents (e.g., metoprolol, carvedilol, propranolol, atenolol), calcium channel blockers (e.g., amlodipine, diltiazem, verapamil), short-acting nitroglycerins (e.g., nitroglycerin), long-acting nitroglycerins (e.g., isosorbide), angiotensin-converting enzyme inhibitors (e.g., ramipril), anti-ischemic agents (e.g., ranolazine), If inhibitors (e.g., ivabradine), and statins (e.g., rosuvastatin, atorvastatin, cerivastatin, fluvastatin, lovastatin, mevastatin, pitavastatin, simvastatin, and any combination thereof)).

In some embodiments, the composition comprising a ROCK inhibitor of the present invention is co-administered with an agent configured to treat autoimmune disorders and/or inflammatory disorders (e.g., rheumatoid arthritis). Examples of such agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), and glucocorticoids (e.g., prednisone, methylprednisone), IL-1 inhibitors, and metalloprotease inhibitors.

In some embodiments, the composition comprising a ROCK inhibitor of the present invention is co-administered with an agent configured to treat atherosclerosis (e.g., statin (e.g., rosuvastatin, atorvastatin, cerivastatin, fluvastatin, lovastatin, mevastatin, pitavastatin, simvastatin, and any combination thereof), fibric acid derivatives (e.g., fenofibrate, gemfibrozil), bile acid sequestrants (e.g., cholestyramine, colestipol), antioxidants (e.g., vitamin E), and nicotinic acid derivatives (e.g., niacin)).

In some embodiments, the composition comprising a ROCK inhibitor of the present invention is co-administered with an agent configured to treat stroke (e.g., anticoagulation agents (e.g., heparin, warfarin, enoxaparin, dalteparin, tinzaparin, unfractionated heparin), repurfusion agents (e.g., thrombolytics (e.g., alteplase, urokinase, streptokinase)), fibrinolytic agents (e.g., alteplase, reteplase, urokinase, streptokinase), and antiplatelet agents (e.g., aspirin, ticlopidine, clopidogrel)).

In some embodiments, the composition comprising a ROCK inhibitor of the present invention is co-administered with an agent configured to treat a cerebral thrombosis (e.g., anticoagulant agents (e.g., heparin, warfarin, enoxaparin, dalteparin, tinzaparin, unfractionated heparin), and thrombolytics (e.g., alteplase, reteplase, urokinase, streptokinase)).

In some embodiments, the composition comprising a ROCK inhibitor of the present invention is co-administered with an agent configured to treat a cerebral embolism (e.g., fibrinolytic agents (e.g., alteplase, reteplase, urokinase, streptokinase), anticoagulant agents (e.g., heparin, warfarin, enoxaparin, dalteparin, tinzaparin, unfractionated heparin)).

In some embodiments, the composition comprising a ROCK inhibitor of the present invention is co-administered with an agent configured to treat a cerebral hemorrhage (e.g., antihypertensive agents (e.g., labetalol, nicardipine), osmotic diuretics (e.g., mannitol), antipyretics/analgesics (e.g., acetaminophen), anticonvulsants (e.g., fosphenyloin), antidotes (e.g., phytonadione, vitamin K, protamine sulfate), antiacids (e.g., famotidine)).

In some embodiments, the composition comprising a ROCK inhibitor of the present invention is co-administered with an agent configured to treat congestive heart failure (e.g., diuretics (e.g., furosemide, metolazone), nitrates (e.g., nitroglycerin, nitroprusside sodium), analgesics (e.g., morphine sulfate), inotropic agents (e.g., dopamine, dobutamine), human B-type natriuetic peptides (e.g., nesiritide)).

In some embodiments, the composition comprising a ROCK inhibitor of the present invention is co-administered with an agent configured to treat coronary artery disease (e.g., statin (e.g., rosuvastatin, atorvastatin, cerivastatin, fluvastatin, lovastatin, mevastatin, pitavastatin, simvastatin, and any combination thereof), fibric acid derivatives (e.g., fenofibrate, gemfibrozil), bile acid sequestrants (e.g., cholestyramine, colestipol), antioxidants (e.g., vitamin E), and nicotinic acid derivatives (e.g., niacin)).

In some embodiments, the composition comprising a ROCK inhibitor of the present invention is co-administered with an agent configured to treat myocardial infarction (e.g., antithrombotic agents (e.g., aspirin, heparin, enoxaparin), vasodilators (e.g., nitroglycerin), beta-andrenergic blockers (e.g., metoprolol, esmolol), thrombolytic agents (e.g., alteplase, tenecteplase, anistreplase, streptokinase, reteplase), platelet aggregation inhibitors (e.g., clopidogrel, eptifibatide, tirofiban, abciximab), analgesics (e.g., morphine sulfate), angiotensin-converting enzyme (ACE) inhibitors (e.g., captopril)).

In some embodiments, the composition comprising a ROCK inhibitor of the present invention is co-administered with an agent configured to treat peripheral vascular disease (e.g., anticoagulants (e.g., heparin, warfarin, enoxaparin, dalteparin, tinzaparin, unfractionated heparin)).

In some embodiments, the composition comprising a ROCK inhibitor of the present invention is co-administered with an agent configured to treat stenosis (e.g., coronary artery stenosis, aortic stenosis, restenosis, pulmonary stenosis) (e.g., prostaglandins (e.g., alprostadil), beta-blockers (e.g., atenolol, esmolol, propranolol)).

In some embodiments, the composition comprising a ROCK inhibitor of the present invention is co-administered with an agent configured to treat vasospasm (e.g., cerebral artery vasospasm, coronary artery vasospasm) (e.g., nitrates (e.g., nitroglycerin, isosorbide dintrate, isosorbide mononitrate), calcium channel blockers (e.g., nifedipine, amlodipine, verapamil, diltiazem)).

In some embodiments, the composition comprising a ROCK inhibitor of the present invention is co-administered with an agent configured to treat hypertension (e.g., pulmonary artery hypertension, systemic arterial hypertension) (e.g., parenteral vasodilators (e.g., epoprostenol, treprostinil), phosphodiesterase (type 5) enzyme inhibitors (e.g., sildenafil), inhaled vasodilators (e.g., iloprost), oral pulmonary hypertension agents (e.g., bosentan, ambrisentan), diuretics (e.g., hydroclorothiazide, spironolactone, amiloride, furosemide), alpha-1-adrenergic blockers (e.g., prazosin, terazosin), beta-adrenergic blocking agents (e.g., atenolol, metoprolol, propranolol, nebivolol), alpha/beta-adrenergic blocking agents (e.g., labetalol, carvedilol), periperhal vasodilators (e.g., hydralazine, minoxidil), calcium channel blockers (e.g., diltiazem, verapamil, nifedipine), angiotensin-converting enzyme (ACE) inhibitors (e.g., captopril, enalapril, lisinopril, ramipril), angiotensin II receptor antagonists (e.g., losartan, valsartan, eprosartan, olmesartan), aldosterone antagonists (e.g., eplerenone), alpha-adrenergic agonists (e.g., methyldopa, clonodine), renin inhibitors (e.g., aliskiren)).

In some embodiments, the composition comprising a ROCK inhibitor of the present invention is co-administered with an agent configured to treat glaucoma (e.g., carbonic anhydrase inhibitors (e.g., acetazolamide, methazolamide), beta-andergic blockers (e.g., tomolol, carteolol, levobetaxolol, levobunolol), alpha-andrenergic agonists (e.g., apraclonidine, brimonidine), corticosteroids (e.g., prednisone), ophthalmic agents (e.g., pilocarpine), hyperosmotics (e.g., glycerin, isosorbide, mannitol)).

In some embodiments, the composition comprising a ROCK inhibitor of the present invention is co-administered with an agent configured to treat erectile dysfunction (e.g., phosphodiesterase inhibitors (e.g., sildenafil, vardenafil, tadalafil), injectable agents (e.g., alprostadil, papaverine, phentolamine, alprostadil), androgens (e.g., testosterone)).

In some embodiments, the composition comprising a ROCK inhibitor of the present invention is co-administered with an agent configured to treat bronchial asthma (e.g., beta2-adrenergic agonist agents (e.g., levalbuterol, salmeterol, formoterol, albuterol), corticosteroids (e.g., fluticasone, triamcinolone, beclomethasone, prednisone, budesonide), bronchodilators (e.g., ipratropium, theophylline), combination of beta2-agonist/corticosteroid agents (e.g., salmeterol/fluticasone, budesonide/formoterol), leukotriene receptor antagonists (e.g., montelukast, zafirlukast), mast cell stabilizers (e.g., cromolyn), 5-lipoxygenase inhibitors (e.g., zileuton), monoclonal antibodies (e.g., omalizumab)).

In some embodiments, the composition comprising a ROCK inhibitor of the present invention is co-administered with an agent configured to treat sarcoidosis (e.g., corticosteroids (e.g., prednisone), cytotoxic agents (e.g., methotrexate, azathioprine), antimalarials (e.g., hydroxychloroquine), immunomodulatory agents (e.g., thalidomide), tumor necrosis factor inhibitors (e.g., infliximab)).

In some embodiments, the composition comprising a ROCK inhibitor of the present invention is co-administered with an agent configured to treat Wegener's granulomatosus (e.g., antineoplastics (e.g., cyclophosphamide, methotrexate), corticosteroids (e.g., prednisone), antibiotics (e.g., trimethoprim, sulfamethoxazole), antithyroids (e.g., potassium iodide), biologics/TNF-alpha inhibitors (e.g., infliximab, azathioprine, rituximab)).

In some embodiments, the composition comprising a ROCK inhibitor of the present invention is co-administered with an agent configured to treat adult respiratory distress syndrome (e.g., corticosteroids (e.g., methylprednisone)).

In some embodiments, the composition comprising a ROCK inhibitor of the present invention is co-administered with an agent configured to treat systemic lupus erythematosus (e.g., nonacetylated salicylates (e.g., choline magnesium trisalicylate), nonsteroidal anti-inflammatory drugs (NSAIDs) (e.g., ibuprofen), antimalarials (e.g., hydroxychloroquine), glucocorticoids (e.g., prednisone, methylprednisone), immunosuppressives/cytotoxic agents (e.g., cyclophosphamide, azathioprine)).

In some embodiments, the composition comprising a ROCK inhibitor of the present invention is co-administered with an agent configured to treat multiple sclerosis (e.g., corticosteroids (e.g., methylprednisone, dexamethasone), immunomodulators (e.g., interferon beta-1a, interferon beta-1b, glatiramer acetate, natalizumab), immunosuppressors (e.g., mitoxantrone, cyclophosphamide, azathioprine, methotrexate), antiviral/anti-Parkinson agent (e.g., amantadine dydrochloride), central nervous system stimulants (e.g., modafinil)).

In some embodiments, the composition comprising a ROCK inhibitor of the present invention is co-administered with an agent configured to treat irritable bowel syndrome (e.g., anticholinergics (e.g., dicyclomine hydrochloride), hyoscyamine sulfate), antidiarrheals (e.g., diphenoxylate hydrochloride with atropine sulfate, loperamide), tricyclic antidepressants (e.g., imipramine, amitriptyline), prokinetics (e.g., cisapride monohydrate, tegaserod), serotonin (5-HT3) receptor antagonists (e.g., alosetron), chloride-channel activator (e.g., lubiprostone), bulk-forming laxatives (e.g., methylcellulose, psyllium)).

In some embodiments, the composition comprising a ROCK inhibitor of the present invention is co-administered with an agent configured to treat systemic sclerosis (e.g., immunomodulatory agents (e.g., prednisone, methotrexate, chlorambucil, cyclosporine, tacrolimus, cyclophosphamide), antifibrotic agents (e.g., penicillamine, colchicines), vasoreactive agents (e.g., nifedipine), antiplatelet agents (e.g., aspirin), antihypertensive agents (e.g., reserpine, methyldopa)).

In some embodiments, the composition comprising a ROCK inhibitor of the present invention is co-administered with an agent configured to treat rheumatoid arthritis (e.g., nonsteroidal anti-inflammatory agents (NSAIDs) (e.g., nabumetone, aspirin, celecoxib, ibuprofen), gold compounds (e.g., auranofin), immunosuppressive agents (e.g., methotrexate), antimalarial agents (e.g., hydroxychloriquine), anti-inflammatory agents (e.g., sulfasalazine), corticosteroids (e.g., betamethasone), disease-modifying agents (e.g., penicillamine, adalimumab), immunomodulators (e.g., abatacept)).

In some embodiments, a ROCK inhibitor (see, e.g., Section I—Exemplary Compounds) is used to treat a subject suffering from a disease involving aberrant angiogenesis. In some embodiments, more than one of the compounds of the present invention are used to treat diseases involving aberrant angiogenesis through modulating (e.g., inhibiting or promoting) the activity of Rho kinase (ROCK) in affected cells or tissues undergoing aberrant angiogenesis. The present invention is not limited to particular types of disease involving aberrant angiogenesis. Examples of diseases involving aberrant angiogenesis include, but are not limited to, cancers (e.g., cancers involving solid tumors), psoriasis, diabetic retinopathy, macular degeneration, atherosclerosis and rheumatoid arthritis.

In some embodiments, the composition comprising a ROCK inhibitor of the present invention is co-administered with an agent configured to treat a disease involving aberrant angiogenesis (e.g., Dalteparin, ABT-510, CNGRC peptide TNF alpha conjugate (NGR-TNF), Combretastatin A4 Phosphate, Dimethylxanthenone Acetic Acide, Lenalidomide, LY317615, PPI-2458, Soy Isoflavone (Genistein; Soy Protein Isolate), Tamoxifen Citrate, Thalidomide, ADH-1, AG-013736, AMG-706, Anti-VEGF Antibody, AZD2171, Bay 43-9006, GW786034, CHIR-265, PI-88, PTK787/ZK 222584, RAD001, Suramin, SU11248, XL184, ZD6474, ATN-161, EMD 121974, and Celecoxib).

In some embodiments, the composition comprising a ROCK inhibitor of the present invention is co-administered with an agent configured to treat cancer (e.g., Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino) ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl- N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nit-rosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; CI-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda). Other anti-cancer agents include, but are not limited to, Antiproliferative agents (e.g., Piritrexim Isothionate), Antiprostatic hypertrophy agent (e.g., Sitogluside), Benign prostatic hyperplasia therapy agents (e.g., Tamsulosin Hydrochloride), Prostate growth inhibitor agents (e.g., Pentomone), and Radioactive agents: Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131. Additional anti-cancer agents include, but are not limited to anti-cancer Supplementary Potentiating Agents Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); Ca++ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. Still other anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2' deoxyadenosine; Fludarabine-PO$_4$; mitoxantrone; mitozolomide; Pentostatin; and Tomudex. One particularly preferred class of anticancer agents are taxanes (e.g., paclitaxel and docetaxel). Another important category of anticancer agent is annonaceous acetogenin.

In some embodiments, the ROCK inhibitors (see, e.g., Section I—Exemplary Compounds) are used to regulate a subject's blood pressure. In some embodiments, more than one of the compounds of the present invention are used to regulate a subject's blood pressure (e.g., maintain a subject's blood pressure within a desired range). In some embodiments, the compounds of the present invention regulate blood pressure through modulating (e.g., inhibiting or promoting) the activity of Rho kinase (ROCK) in affected cells or tissues. In some embodiments, the compounds of the present invention are co-administered with at least one additional agent for purposes of regulating a subject's blood pressure (e.g., thiazides and related diuretics (e.g., hydrochlorothiazide, chlorthalidone), alpha/beta-adrenergic blocking agents (e.g., carvedilol), beta-adrenergic blocking agents (e.g., bisoprolol, atenolol, metoprolol), angiotensin-converting enzyme inhibitors (e.g., captopril, fosinopril, benazepril, quinapril, ramipril), angiotensin II receptor antagonists (e.g., losartan, valsartan, candesartan, irbesartan, eprosartan, and olmesartan), calcium channel blockers—nondihydropyridines (e.g., diltiazem, and verapamil), calcium channel blockers—dihydropyridines (e.g., Amlodipine, nifedipine, felodipine), vasodilators—peripheral (e.g., hydralazine), aldosterone antagonists (e.g., spironolactone)).

In some embodiments, a ROCK inhibitor (see, e.g., Section I—Exemplary Compounds) is used to regulate a subject's HDL/LDL levels. In some embodiments, more than one of the compounds of the present invention are used to treat regulate a subject's HDL/LDL levels (e.g., lower a subject's LDL levels, raise a subject's HDL levels). In some embodiments, the compounds of the present invention regulate HDL/LDL levels through modulating (e.g., inhibiting or promoting) the activity of Rho kinase (ROCK) in affected cells or tissues. In some embodiments, the compounds of the present invention are co-administered with at least one additional agent for purposes of regulating a subject's HDL/LDL levels. Examples of additional agents for purposes of regulating a subject's HDL/LDL levels include, but are not limited to, antilipemic agents (e.g., niacin, nicotinic acid, gemfibrozil, fenofibrate), and HMG-CoA reductase inhibitors (e.g., atorvastatin, simvastatin, pravastatin, lovastatin, fluvastatin, and rosuvastatin).

EXAMPLES

The following examples are provided to demonstrate and further illustrate certain preferred embodiments of the present invention and are not to be construed as limiting the scope thereof.

Example 1

Preparation of Compound 1

Intermediate A: (R)-7-chloro-3-(4-iodobenzyl)-3,4-dihydro-1H-benzo[e][1,4]diazepine-2,5-dione

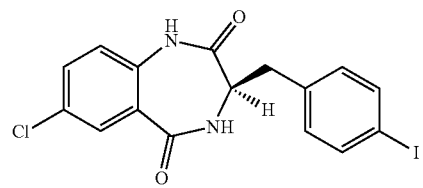 [SMILES: O=C1N[C@H](Cc2ccc(I)cc2)C(=O)Nc2ccc(Cl)cc21]

A 500-mL round bottom flask was charged with 4-iodo-D-phenylalanine (2 g, 0.007 mol) dissolved in acetonitrile/H₂O (1:1, 150 mL). Triethylamine (0.94 mL, 0.007 mol, 1 equiv) was added to the solution and the mixture was stirred at room temperature for 30 min. 5-chloro-isatoic anhydride (1.45 g, 0.007 mol, 1 equiv) was added to the stirred solution, and the reaction was heated at 80° C. and stirred overnight. The reaction mixture was cooled, diluted with ethyl acetate (300 mL), and washed with water (2×200 mL). The solvent was removed in vacuo. To the yellow solid was added glacial acetic acid (300 mL). The stirred solution was heated at 130° C. overnight. After cooling to room temperature, the reaction mixture was again diluted with ethyl acetate (300 mL), washed with water (2×200 mL). The solvent was removed in vacuo and flash chromatography of the residue on silica gel (6 inches×150 mm, step gradient of hexanes to hexanes-ethyl acetate (50:50) increasing in 1 column volume increments of 5% ethyl acetate as eluant) afforded a white solid (1.2 g, 44%). TLC (silica gel, hexanes-ethyl acetate (50:50)) R$_f$=0.5. Optical rotation (acetone, 0.998 dm)=−164.9°.

$^1$H NMR (DMSO, 500 MHz): δ (ppm) 2.79-2.82 (1H, dd, J=9.3, 14.2 Hz), 3.04-3.08 (1H, dd, J=5.2, 14.2 Hz), 3.93-3.95 (1H, m), 7.10-7.15 (3H, m), 7.56-7.61 (4H, m), 8.66 (1H, dd, J=6.0 Hz), 10.50 (1H, s).

Intermediate B: (R)-7-chloro-3-(4-iodobenzyl)-1-methyl-3,4-dihydro-1H-benzo[e][1,4]diazepine-2,5-dione

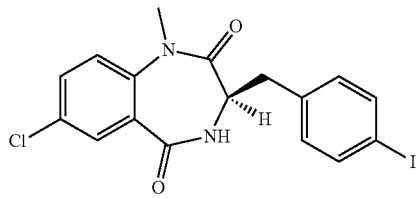 [SMILES: CN1C(=O)[C@@H](Cc2ccc(I)cc2)NC(=O)c2cc(Cl)ccc21]

A 250-mL round bottom flask was charged with intermediate A (1.2 g, 3.00 mmol) dissolved in dimethylformamide (100 mL), and cooled to 0° C. Sodium hydride (60% dispersed in mineral oil, 0.120 g, 3.00 mmol, 1 equiv) was added to the solution and the mixture was stirred for 30 min at 0° C. Iodomethane (0.19 mL, 3.00 mmol, 1 equiv) was added and the solution was stirred for 4 h and allowed to warm to room temperature. The reaction was quenched by the addition of water (30 mL). The solution was poured into ethyl acetate (30 mL), and the organic and aqueous layers were separated. The aqueous layer was extracted with ethyl acetate (3×30 mL), washed with water (2×20 mL) and brine (1×20 mL), and dried over magnesium sulfate. The solvent was in vacuo affording a yellow oil.

Flash chromatography of the residue on silica gel (6 inches×150 mm, step gradient of hexanes to hexanes-ethyl acetate (50:50) increasing in 1 column volume increments of 5% ethyl acetate as eluant) afforded a yellow/white solid (0.877 g, 66%). TLC (silica gel, hexanes-ethyl acetate (50:50)) R$_f$=0.61. Optical rotation (acetone, 0.998 dm)=−143.8°.

$^1$H NMR (Acetone, 400 MHz): δ (ppm) 3.05-3.09 (1H, dd, J=8.5, 14.4 Hz), 3.33-3.37 (4H, m), 4.22-4.25 (1H, m), 7.20-7.21 (2H, d, J=8.1 Hz), 7.42-7.43 (1H, d, J=8.8 Hz), 7.59-7.63 (3H, m), 7.69 (1H, d, J=2.4 Hz), 7.97 (1H, bs).

Compound 1: (R)-3-(4-(1H-pyrazol-4-yl)benzyl)-7-chloro-1-methyl-3,4-dihydro-1H-benzo[e][1,4]diazepine-2,5-dione

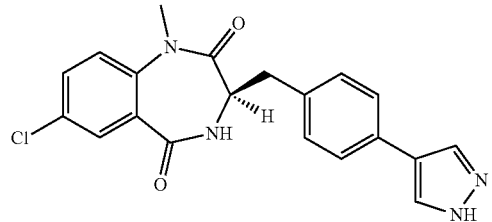 [SMILES: CN1C(=O)[C@@H](Cc2ccc(-c3cn[nH]c3)cc2)NC(=O)c2cc(Cl)ccc21]

To a solution of intermediate B (0.197 g, 0.45 mmol) dissolved in dimethylformamide (25 mL) was added 4-pyrazole boronic acid pinnacle ester (0.174 g, 0.90 mmol, 2 equiv), [1,1'-bis(diphenylphosphino)ferrocene]dichloropalladium (II) (0.037 g, 0.045 mmol, 0.1 equiv), and sodium carbonate (1.80 mL of 2 M aqueous solution, 3.60 mmol, 8 equiv). The solution was heated at 130° C. for 30 min and then cooled to room temperature. The mixture was poured into water (15 mL), and extracted with dichloromethane (3×15 mL). The organic layers were collected, washed with water (2×15 mL), brine (1×15 mL) and dried over magnesium sulfate. The solution was concentrated, and purified by flash chromatography of the residue on silica gel (2 inches×20 mm, step gradient of hexanes to hexanes-ethyl acetate (50:50) increasing in 1 column volume increments of 5% ethyl acetate as eluent) affording a yellow solid (23 mg, 11%). TLC (silica gel, dichloromethane-methanol (90:10)) R$_f$=0.38. HPLC trace on Chiracel OJ-H analytical column with 100% MeOH as an eluent at 20° C. afforded two peaks at 26.1 min and 27.9 min (95.0:5.0, R:S).

$^1$H NMR (Acetone, 500 MHz): δ (ppm) 3.06-3.10 (1H, dd, J=8.6, 14.4 Hz), 3.35-3.41 (4H, m), 4.20-4.24 (1H, m), 7.35-7.37 (2H, d, J=8.1 Hz), 7.45-7.52 (3H, m), 7.59-7.62 (1H, dd, J=2.7, 8.8 Hz), 7.66 (1H, dd, J=2.4 Hz), 7.67 (1H, d, J=2.7 Hz), 7.81 (bd, 1H), 7.97 (bs, 2H).

$^{13}$C NMR (500 MHz, Acetone): δ (ppm) 34.0, 34.7, 53.9, 69.4, 121.7, 124.0, 125.3, 129.2, 129.9, 130.5, 131.6, 131.9, 135.4, 136.2, 140.2, 154.8, 166.4, 170.1.

Preparation of Compound 2

Compound 2: (R)-3-(4-(2-aminopyridin-4-yl)benzyl)-7-chloro-1-methyl-3,4-dihydro-1H-benzo[e][1,4]diazepine-2,5-dione

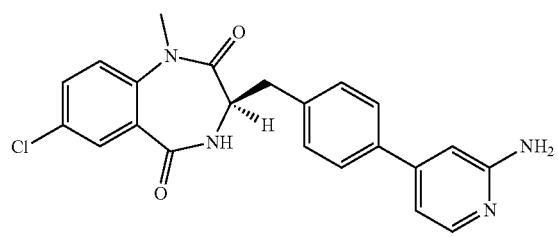 [SMILES: CN1C(=O)[C@@H](Cc2ccc(-c3ccnc(N)c3)cc2)NC(=O)c2cc(Cl)ccc21]

To a solution of intermediate B (0.200 g, 0.44 mmol) dissolved in dimethylformamide (50 mL) was added 3-amino-4-pyridine boronic acid pinnacle ester (0.200 g, 0.88 mmol, 2 equiv), [1,1' bis(diphenylphosphino)ferrocene]dichloropalladium(II) (0.036 g, 0.044 mmol, 0.1 equiv), and sodium carbonate (1.76 mL of 2 M aqueous solution, 3.52 mmol, 8 equiv). The solution was heated at 130° C. for 30 min and then cooled to room temperature. The mixture was poured into water (15 mL), and extracted with dichloromethane (3×15 mL). The organic layers were collected, washed with water (2×15 mL), brine (1×15 mL) and dried over magnesium sulfate. The solution was concentrated, and purified by flash chromatography of the residue on silica gel (4 inches×20 mm, step gradient of hexanes to hexanes-ethyl acetate (50:50) increasing in 1 column volume increments of 5% ethyl acetate as eluant) affording a yellow solid (25.7 mg, 14%). TLC (silica gel, dichloromethane-methanol (90:10)) $R_f$=0.22. Optical rotation (acetone, 0.998 dm)=−214°. HPLC trace on Chiracel OJ-H analytical column with 100% MeOH as an eluent at 10° C. afforded two peaks at 54.8 min and 58.3 min (1.5:98.5, S:R).

$^1$H NMR (500 MHz, Acetone): δ (ppm) 3.14-3.17 (1H, dd, J=8.5 Hz), 3.41-3.45 (4H, m), 4.26-4.28 (1H, ABq), 5.46 (2H, bs), 6.80-8.62 (2H, m), 7.44-7.47 (3H, m), 7.55-7.56 (2H, dd, J=1.7, 6.6 Hz), 7.55-7.56 (1H, dd, J=2.7, 8.8 Hz), 7.67 (1H, d, J=2.7 Hz), 8.00 (2H, m).

$^{13}$C NMR (500 MHz, Acetone): δ (ppm) 34.0, 34.8, 61.5, 69.4, 105.2, 110.8, 124.0, 126.7, 129.3, 129.9, 130.5, 131.9, 137.3, 138.3, 140.1, 148.6, 148.8, 160.5, 166.5, 170.0.

Preparation of Compound 3

Intermediate C:
6-methoxy-1H-benzo[d][1,3]oxazine-2,4-dione

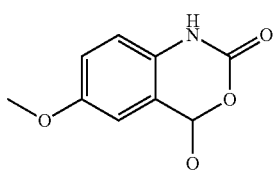

To a stirred solution of 2-amino-5-methoxy benzoic acid (9 g, 0.054 mmol) in acetonitrile (60 mL, 1 M), was added pyridine (8.7 mL, 0.108 mmol, 2 equiv), and triphosgene (15.9 g, 0.054 mmol, 1 equiv) in dichloromethane (85 mL, 0.7 M). The orange reaction solution was heated at 50° C. for two hours then cooled to room temperature. The solution was diluted with water (50 mL), and the organic and aqueous layers were separated. The aqueous layer was washed with dichloromethane (3×50 mL), and the combined organic layers were washed once with brine (50 mL), and dried over magnesium sulfate. The solvent was removed in vacuo leaving a yellow solid. The solid was titrated with hexanes to yield 8-chloro-1H-benzo[d][1,3]oxazine-2,4-dione (8.3 g, 80%) as a white solid.

$^1$H NMR (Acetone, 500 MHz): δ (ppm) 3.80 (3H, s), 7.09-7.11 (1H, t, J=9.0 Hz), 7.33 (1H, s), 7.37-7.39 (1H, dd, J=2.9, 8.7 Hz), 11.60 (1H, bs).

Intermediate D: (S)-3-(4-iodobenzyl)-7-methoxy-3,4-dihydro-1H-benzo[e][1,4]diazepine-2,5-dione

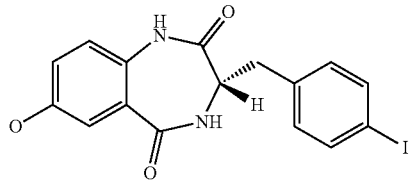 [SMILES: O=C1N[C@@H](Cc2ccc(I)cc2)C(=O)Nc2ccc(O)cc21]

A 500-mL round bottom flask was charged with 4-iodo-L-phenylalanine (2 g, 0.007 mol) dissolved in acetonitrile/H$_2$O (1:1, 150 mL). Triethylamine (0.94 mL, 0.007 mol, 1 equiv) was added to the solution and the mixture was stirred at room temperature for 30 min. Intermediate C (1.31 g, 0.007 mol, 1 equiv) was added to the stirred solution, and the reaction was heated at 80° C. and stirred overnight. The reaction mixture was cooled, diluted with ethyl acetate (300 mL), and washed with water (2×200 mL). The solvent was removed in vacuo. To the yellow solid was added glacial acetic acid (300 mL). The stirred solution was heated at 130° C. overnight. After cooling to room temperature, the reaction mixture was again diluted with ethyl acetate (300 mL), washed with water (2×200 mL). The solvent was removed in vacuo and flash chromatography of the residue on silica gel (6 inches×150 mm, step gradient of hexanes to hexanes-ethyl acetate (50:50) increasing in 1 column volume increments of 5% ethyl acetate as eluent) afforded a yellow solid (0.42 g, 13%). TLC (silica gel, hexanes-ethyl acetate (50:50)) $R_f$=0.53. Optical rotation (DMSO, 0.998 dm)=+122.3°.

$^1$H NMR (DMSO, 500 MHz): δ (ppm) 2.76-2.80 (1H, dd, J=9.5, 14.2 Hz), 3.04-3.08 (1H, dd, J=5.1, 14.1 Hz), 3.32 (3H, s), 3.83-3.85 (1H, m), 7.01-7.02 (1H, d, J=8.7 Hz), 7.09-7.15 (4H, m), 7.59-7.61 (2H, d, J=8.3 Hz), 8.52-8.54 (1H, bd, J=6.1 Hz), 10.23 (1H, bs).

Intermediate E: (S)-3-(4-iodobenzyl)-7-methoxy-1-methyl-3,4-dihydro-1H-benzo[e][1,4]diazepine-2,5-dione

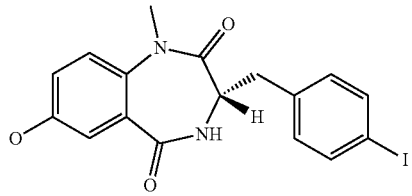 [SMILES: CN1C(=O)[C@H](Cc2ccc(I)cc2)NC(=O)c2cc(O)ccc21]

A 100-mL round bottom flask was charged with intermediate D (0.42 g, 0.99 mmol) dissolved in dimethylformamide (50 mL), and cooled to 0° C. Sodium hydride (60% dispersed in mineral oil, 0.024 g, 0.99 mmol, 1 equiv) was added to the solution and the mixture was stirred for 30 min at 0° C. Iodomethane (0.06 mL, 0.99 mmol, 1 equiv) was added and the solution was stirred for four hours and allowed to warm to room temperature. The reaction was quenched by the addition of water (10 mL). The solution was poured into ethyl acetate (10 mL), and the organic and aqueous layers were separated. The aqueous layer was extracted with ethyl acetate (3×10 mL), washed with water (2×10 mL) and brine (1×10 mL), and dried over magnesium sulfate. The solvent was in vacuo affording a yellow oil. Flash chromatography of the residue on silica gel (2 inches×20 mm, step gradient of hexanes to hexanes-ethyl acetate (50:50) increasing in 1 column volume increments of 5% ethyl acetate as eluent) afforded a brown solid (0.317 g, 70.7%). TLC (silica gel, hexanes-ethyl acetate (50:50)) $R_f$=0.66. Optical rotation (acetone, 0.998 dm)=+ 129.5°.

$^1$H NMR (DMSO, 500 MHz): δ (ppm) 2.76-2.80 (1H, dd, J=9.5, 14.2 Hz), 3.04-3.15 (4H, m), 3.31-3.32 (3H, s), 3.86-3.89 (1H, m), 7.01-7.03 (1H, d, J=8.7 Hz), 7.06-7.15 (4H, m), 7.59-7.61 (2H, d, J=8.3 Hz), 8.52-8.54 (1H, bd, J=6.1 Hz).

Compound 3: (S)-3-(4-(2-aminopyridin-4-yl)benzyl)-7-methoxy-1-methyl-3,4-dihydro-1H-benzo[e][1,4]diazepine-2,5-dione

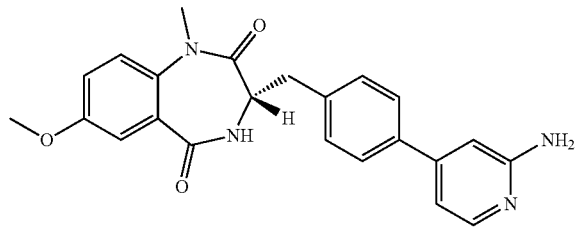 [SMILES: COc1ccc2c(c1)C(=O)N[C@@H](Cc1ccc(-c3ccnc(N)c3)cc1)C(=O)N2C]

To a solution of intermediate E (0.120 g, 0.28 mmol) dissolved in dimethylformamide (25 mL) was added 3-amino-4-pyridine boronic acid pinnacle ester (0.123 g, 0.55 mmol, 2 equiv), [1,1'-bis(diphenylphosphino)ferrocene]dichloropalladium(II) (0.023 g, 0.028 mmol, 0.1 equiv), and sodium carbonate (1.1 mL of 2 M aqueous solution, 2.24 mmol, 8 equiv). The solution was heated at 130° C. for 30 min and then cooled to room temperature. The mixture was poured into water (15 mL), and extracted with dichloromethane (3×15 mL). The organic layers were collected, washed with water (2×15 mL), brine (1×15 mL) and dried over magnesium sulfate. The solution was concentrated, and purified by flash chromatography of the residue on silica gel (2 inches×20 mm, step gradient of hexanes to hexanes-ethyl acetate (50:50) increasing in 1 column volume increments of 5% ethyl acetate as eluent) affording a light brown solid (10.8 mg, 7.2%). TLC (silica gel, dichloromethane-methanol (90:10)) $R_f$=0.28. Optical rotation (acetone, 0.998 dm)=+118.0°.

$^1$H NMR (500 MHz, Acetone): δ (ppm) 3.09-3.14 (1H, dd, J=8.5, 14.4 Hz), 3.37-3.43 (4H, m), 3.85 (3H, s), 4.17-4.19 (1H, m), 5.41 (2H, bs), 6.79-6.82 (2H, m), 7.14-7.19 (2H, m), 7.34-7.36 (1H, d, J=8.8 Hz), 7.46-7.49 (2H, d, J=8.3 Hz), 7.55-7.57 (2H, d, J=8.0 Hz), 7.71 (1H, bd, J=5.4 Hz) 8.00 (1H, d, J=5.4 Hz).

$^{13}$C NMR (500 MHz, Acetone): δ (ppm) 34.1, 34.8, 54.0, 55.0, 69.4, 105.1, 110.8, 112.9, 118.7, 123.6, 126.6, 130.1, 134.5, 137.3, 138.7, 147.3, 148.6, 148.9, 156.8, 170.1.

Preparation of Compound 4

Intermediate F: (S)-7-chloro-3-(4-iodobenzyl)-3,4-dihydro-1H-benzo[e][1,4]diazepine-2,5-dione

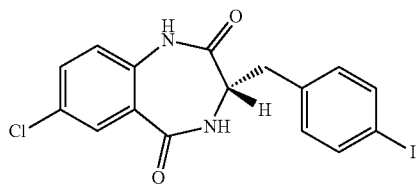 [SMILES: O=C1N[C@@H](Cc2ccc(I)cc2)C(=O)Nc2ccc(Cl)cc21]

A 500-mL round bottom flask was charged with 4-iodo-L-phenylalanine (2 g, 0.007 mol) dissolved in acetonitrile/$H_2O$ (1:1, 150 mL). Triethylamine (0.94 mL, 0.007 mol, 1 equiv) was added to the solution and the mixture was stirred at room temperature for 30 min. 5-chloro-isatoic anhydride (1.5 g, 0.007 mol, 1 equiv) was added to the stirred solution, and the reaction was heated at 80° C. and stirred overnight. The reaction mixture was cooled, diluted with ethyl acetate (300 mL), and washed with water (2×200 mL). The solvent was removed in vacuo. To the yellow solid was added glacial acetic acid (300 mL). The stirred solution was heated at 130° C. overnight. After cooling to room temperature, the reaction mixture was again diluted with ethyl acetate (300 mL), washed with water (2×200 mL). The solvent was removed in vacuo and flash chromatography of the residue on silica gel (6 inches×150 mm, step gradient of hexanes to hexanes-ethyl acetate (50:50) increasing in 1 column volume increments of 5% ethyl acetate as eluent) afforded a yellow solid (1.2 g, 41%). TLC (silica gel, hexanes-ethyl acetate (50:50)) $R_f$=0.5. Optical rotation (acetone, 0.998 dm)=+161.2°.

$^1$H NMR (DMSO, 500 MHz): δ (ppm) 2.78-2.81 (1H, dd, J=9.2, 14.2 Hz), 3.04-3.08 (1H, dd, J=5.2, 14.2 Hz), 3.94-3.95 (1H, m), 7.10-7.15 (3H, m), 7.56-7.61 (4H, m), 8.66 (1H, dd, J=6.1 Hz), 10.50 (1H, s).

Intermediate G: (S)-7-chloro-3-(4-iodobenzyl)-3,4-dihydro-1H-benzo[e][1,4]diazepine-2,5-dione

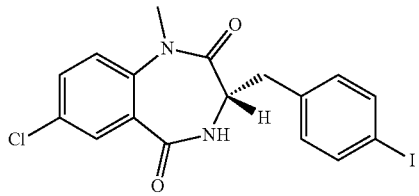 [SMILES: CN1C(=O)[C@H](Cc2ccc(I)cc2)NC(=O)c2cc(Cl)ccc21]

A 250-mL round bottom flask was charged with intermediate F (1.2 g, 2.8 mmol) dissolved in dimethylformamide (100 mL), and cooled to 0° C. Sodium hydride (60% dispersed in mineral oil, 0.112 g, 2.8 mmol, 1 equiv) was added to the solution and the mixture was stirred for 30 min at 0° C. Iodomethane (0.17 mL, 2.8 mmol, 1 equiv) was added and the solution was stirred for four hours and allowed to warm to room temperature. The reaction was quenched by the addition of water (20 mL). The solution was poured into ethyl acetate (40 mL), and the organic and aqueous layers were separated. The aqueous layer was extracted with ethyl acetate (3×30 mL), washed with water (2×20 mL) and brine (1×20 mL), and dried over magnesium sulfate. The solvent was in vacuo affording a yellow oil. Flash chromatography of the residue on silica gel (6 inches×150 mm, step gradient of hexanes to hexanes-ethyl acetate (50:50) increasing in 1 column volume increments of 5% ethyl acetate as eluent) afforded a yellow solid (0.747 g, 60%). TLC (silica gel, hexanes-ethyl acetate (50:50)) $R_f$=0.61. Optical rotation (acetone, 0.998 dm)=+ 148.0°.

$^1$H NMR (Acetone, 400 MHz): δ (ppm) 3.05-3.09 (1H, dd, J=8.5, 14.4 Hz), 3.33-3.37 (4H, m), 4.22-4.25 (1H, m), 7.20-7.21 (2H, d, J=8.1 Hz), 7.42-7.43 (1H, d, J=8.8 Hz), 7.59-7.63 (3H, m), 7.69 (1H, d, J=2.4 Hz), 7.97 (1H, bs).

Compound 4: (S)-3-(4-(1H-pyrrolo[2,3-b]pyridin-4-yl)benzyl)-7-chloro-1-methyl-3,4-dihydro-1H-benzo[e][1,4]diazepine-2,5-dione

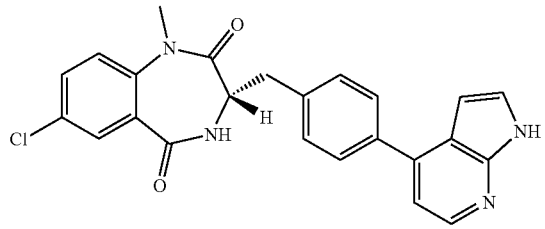 [SMILES: CN1C(=O)[C@H](Cc2ccc(-c3ccnc4[nH]ccc34)cc2)NC(=O)c2cc(Cl)ccc21]

To a solution of intermediate G (0.200 g, 0.45 mmol) dissolved in dimethylformamide (25 mL) was added 4-(1,5-dimethyl-2,4-dioxa-3-borabicyclo[3.1.0]hexan-3-yl)-1H-pyrrolo[2,3-b]pyridine (0.215 g, 0.90 mmol, 2 equiv), [1,1'-bis(diphenylphosphino)ferrocene]dichloropalladium(II) (0.037 g, 0.045 mmol, 0.1 equiv), and sodium carbonate (1.8 mL of 2 M aqueous solution, 3.60 mmol, 8 equiv). The solution was heated at 130° C. for 30 min and then cooled to room temperature. The mixture was poured into water (15 mL), and extracted with dichloromethane (3×15 mL). The organic layers were collected, washed with water (2×15 mL), brine (1×15 mL) and dried over magnesium sulfate. The solution was concentrated, and purified by flash chromatography of the residue on silica gel (2 inches×20 mm, step gradient of hexanes to hexanes-ethyl acetate (50:50) increasing in 1 column volume increments of 5% ethyl acetate as eluent) affording a yellow solid (33.1 mg, 16%). TLC (silica gel, dichloromethane-methanol (90:10)) $R_f$=0.33. Optical rotation (acetone, 0.998 dm)=+150.0°. HPLC trace on Chiracel OJ-H analytical column with 100% MeOH as an eluent at 45° C. afforded two peaks at 41.5 min and 42.0 min (95.0:5.0, S:R).

$^1$H NMR (500 MHz, Acetone): δ (ppm) 3.19-3.24 (1H, dd, J=8.2, 14.4 Hz), 3.43 (3H, s), 3.47-3.52 (3H, dd, J=5.9, 14.4 Hz), 4.33-4.35 (1H, m), 6.65 (1H, d, J=3.4 Hz), 7.16-7.17 (1H, d, J=4.9 Hz), 7.45-7.46 (1H, d, J=8.7 Hz), 7.53-7.56 (3H, m), 7.60-7.62 (1H, dd, J=2.6, 8.1 Hz), 7.69-7.71 (2H, d, J=2.6, 8.1 Hz), 8.15 (1H, bd, J=5.8 Hz) 8.31 (1H, d, J=4.9 Hz), 11.00 (1H, bs).

$^{13}$C NMR (500 MHz, Acetone): δ (ppm) 34.1, 34.8, 53.8, 69.3, 99.5, 109.3, 114.3, 117.8, 124.1, 125.7, 128.3, 129.3, 129.9, 130.5, 131.9, 137.3, 138.0, 140.2, 140.8, 143.1, 166.7, 170.0.

Preparation of Compound 5

Compound 5: (S)-3-(4-(1H-pyrrolo[2,3-b]pyridin-4-yl)benzyl)-7-methoxy-1-methyl-3,4-dihydro-1H-benzo[e][1,4]diazepine-2,5-dione

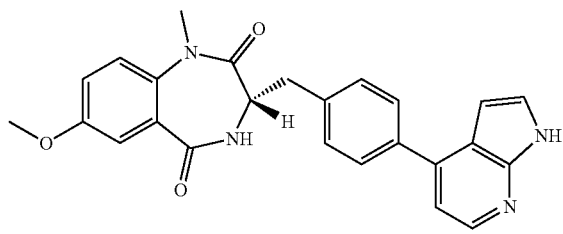 [SMILES: COc1ccc2c(c1)C(=O)N[C@@H](Cc1ccc(-c3ccnc4[nH]ccc34)cc1)C(=O)N2C]

To a solution of intermediate E (0.120 g, 0.28 mmol) dissolved in dimethylformamide (25 mL) was added 4-(1,5-dimethyl-2,4-dioxa-3-borabicyclo[3.1.0]hexan-3-yl)-1H-pyrrolo[2,3-b]pyridine (0.134 g, 0.55 mmol, 2 equiv), [1,1'-bis(diphenylphosphino)ferrocene]dichloropalladium(II) (0.023 g, 0.028 mmol, 0.1 equiv), and sodium carbonate (1.1 mL of 2 M aqueous solution, 2.24 mmol, 8 equiv). The solution was heated at 130° C. for 30 min and then cooled to room temperature. The mixture was poured into water (15 mL), and extracted with dichloromethane (3×15 mL). The organic layers were collected, washed with water (2×15 mL), brine (1×15 mL) and dried over magnesium sulfate. The solution was concentrated, and purified by flash chromatography of the residue on silica gel (2 inches×20 mm, step gradient of hexanes to hexanes-ethyl acetate (50:50) increasing in 1 column volume increments of 5% ethyl acetate as eluent) affording a brown crystalline solid (14.2 mg, 10.7%). TLC (silica gel, dichloromethane-methanol (90:10)) $R_f$=0.33. Optical rotation (acetone, 0.998 dm)=+116.5°. HPLC trace on Chiracel OJ-H analytical column with 100% MeOH as an eluent at 40° C. afforded two peaks at 41.3 min and 50.1 min (96.2:3.8, S:R).

$^1$H NMR (500 MHz, Acetone): δ (ppm) 3.16-3.21 (1H, dd, J=8.5, 14.4 Hz), 3.38 (3H, s), 3.46-3.50 (1H, dd. J=5.9, 14.4 Hz), 3.85 (3H, s), 4.23-4.26 (1H, m), 6.65 (1H, d, J=3.6 Hz), 7.15-7.17 (2H, m), 7.23 (1H, d, J=3.0 Hz), 7.35-7.37 (1H, d, J=8.8 Hz), 7.53-7.57 (3H, m), 7.70-7.71 (2H, d, J=8.0 Hz), 7.96 (1H, bd, J=5.8 Hz) 8.31 (1H, d, J=4.9 Hz), 11.01 (1H, bs).

$^{13}$C NMR (500 MHz, Acetone): δ (ppm) 34.2, 34.8, 53.9, 55.1, 69.4, 99.5, 109.3, 113.0, 114.4, 118.8, 123.6, 125.8, 128.3, 129.9, 130.1, 133.8, 137.3, 138.3, 140.8, 143.2, 156.8, 167.6, 170.1.

Example II

This example describes inhibition of ROCK1 and ROCK2 activity with Compounds 1, 2, 3, 4, and 5 (see Example I) of the present invention.

ROCK-I (h) Inhibition Assay:

In a final reaction volume of 25 μL, ROCK-I (h, amino acids 17-535) (5-10 mU) was incubated with 8 mM MOPS pH 7.0, 0.2 mM EDTA, 30 μM KEAKEKRQE-QIAKRRRLSSLRASTSKSGGSQK, 10 mM magnesium acetate and [γ-$^{32}$P-ATP] (specific activity approx. 500 cpm/pmol, concentration as required). The reaction was initiated by the addition of the MgATP mix. After incubation for 40 minutes at room temperature, the reaction was stopped by the addition of 5 μL of a 3% phosphoric acid solution. 10 μL of the reaction was then spotted onto a P30 filtermat and washed three times for 5 minutes in 75 mM phosphoric acid and once in methanol prior to drying and scintillation counting.

ROCK-II (h) Inhibition Assay:

In a final reaction volume of 25 μL, ROCK-II (h, amino acids 11-552) (5-10 mU) was incubated with 50 mM Tris pH 7.5, 0.1 mM EGTA, 30 [μM KEAKEKRQEQIAKRRRLSS-LRASTSKSGGSQK, 10 mM magnesium acetate and γ-$^{32}$P-ATP] (specific activity approx. 500 cpm/pmol, concentration as required). The reaction was initiated by the addition of the MgATP mix. After incubation for 40 minutes at room temperature, the reaction was stopped by the addition of 5 μL of a 3% phosphoric acid solution. 10 μL of the reaction was then spotted onto a P30 filter-mat and washed three times for 5 minutes in 75 mM phosphoric acid and once in methanol prior to drying and scintillation counting.

Table 1 shows inhibition of ROCK1 and ROCK2 activity with compounds 1, 2, 3, 4 and 5 of the present invention (see Example I) as measured with the respective ROCK1 and ROCK2 inhibition assays (IC50 values).

TABLE 1

| Compound | ROCK1 IC$_{50}$ | ROCK2 IC$_{50}$ |
|---|---|---|
| 1 | >30 μM | 1.0 μM |
| 2 | >10 μM | 7.1 μM |
| 3 | >10 μM | 2.4 μM |
| 4 | 5.1 μM | 250 nM |
| 5 | 2.8 μM | 200 nM |

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A compound defined by a formula selected from the group consisting of:

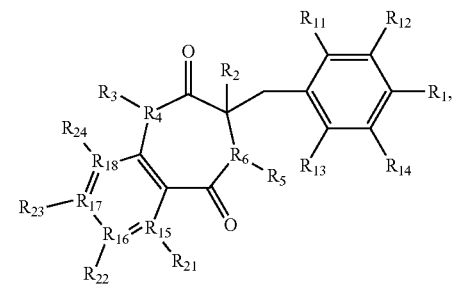

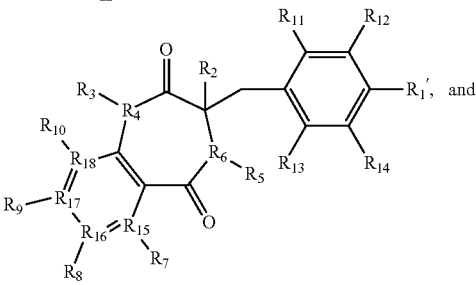

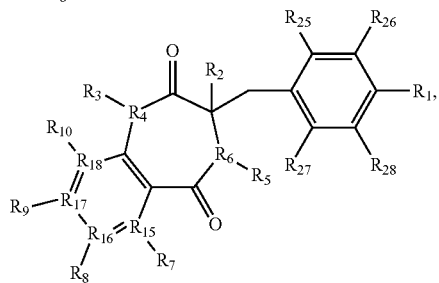

or a pharmaceutically acceptable salt thereof;

wherein $R_1$ is selected from the group consisting of: hydrogen, alkyl,

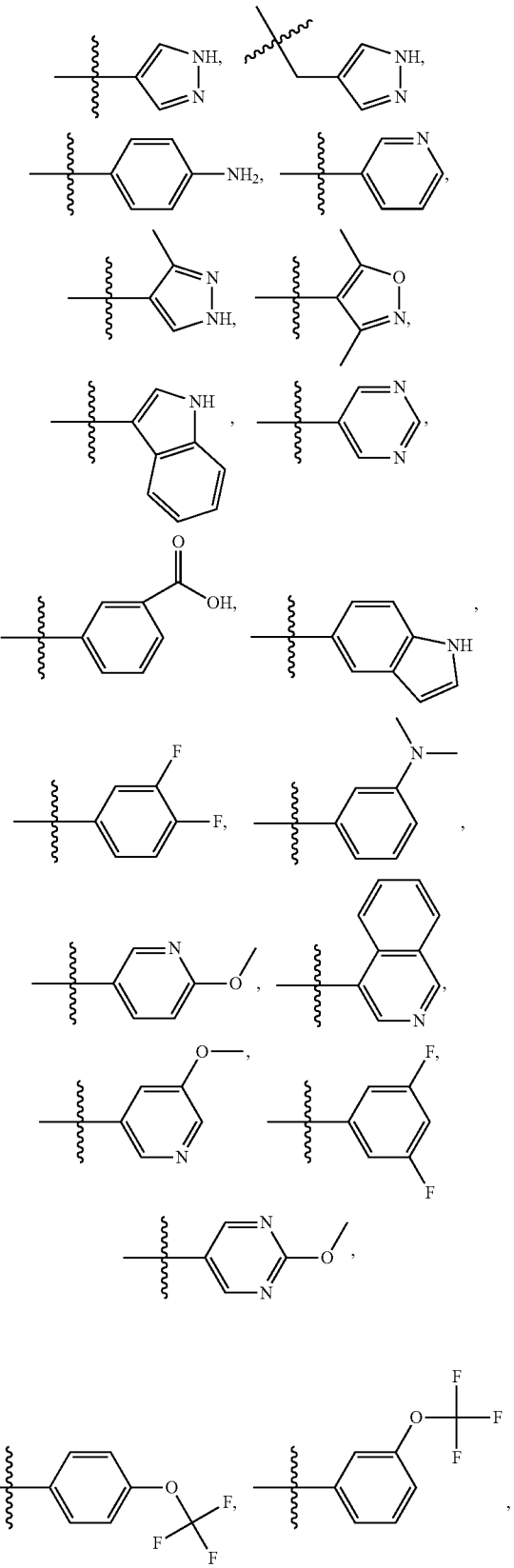

-continued

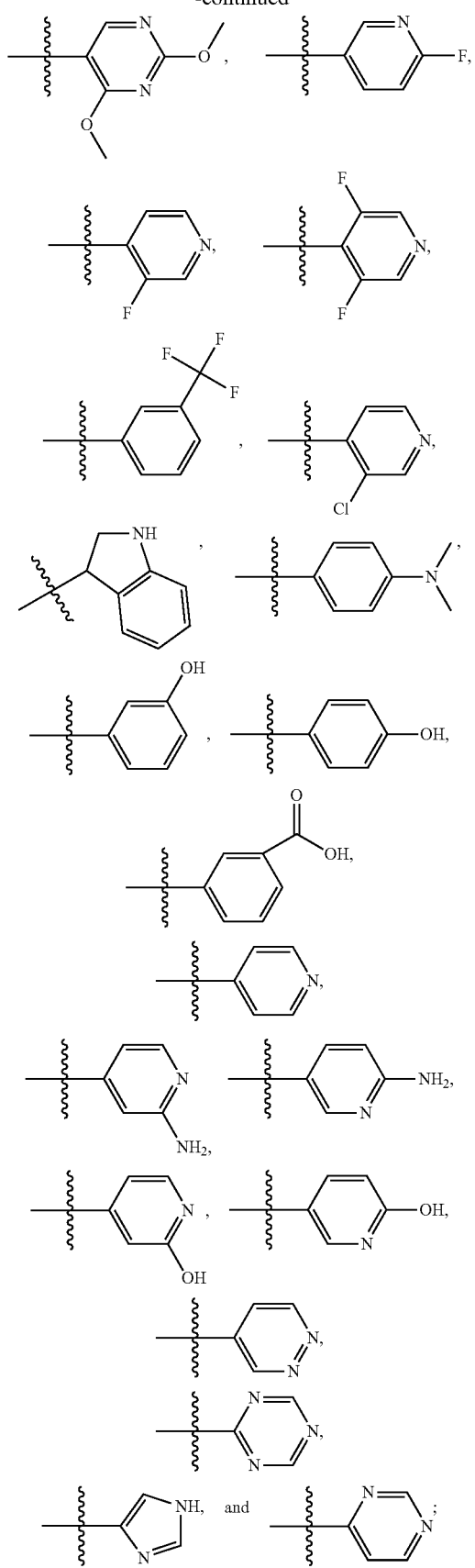

wherein $R_{1'}$ is selected from the group consisting of

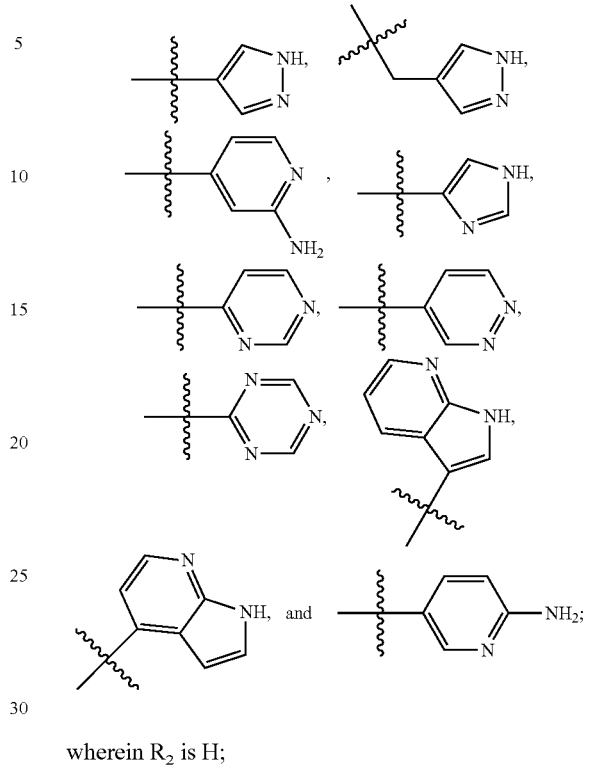

wherein $R_2$ is H;
wherein $R_3$ is selected from the group consisting of H; alkyl; substituted alkyl; and OH;
wherein $R_4$ is N;
wherein $R_5$ is selected from the group consisting of H, alkyl, substituted alkyl, mono-substituted aryl, di-substituted aryl, and tri-substituted aryl;
wherein $R_6$ is N;
wherein $R_7$, $R_8$, $R_9$, and $R_{10}$ are independently absent or selected from the group consisting of, H, halogen, and

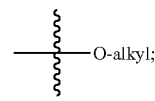

wherein $R_{11}$, $R_{12}$, $R_{13}$, and $R_{14}$, are H;
wherein $R_{15}$, $R_{16}$, $R_{17}$, and $R_{18}$ are independently selected from the group consisting of C and N;
wherein $R_{21}$, $R_{22}$, $R_{23}$, and $R_{24}$ are independently absent or selected from the group consisting of, H, halogen, and,

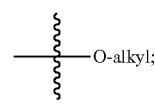

wherein no more than two of $R_{21}$, $R_{22}$, $R_{23}$, and $R_{24}$ can be hydrogen; and
wherein $R_{25}$, $R_{26}$, $R_{27}$, and $R_{28}$, are independently selected from the group consisting of hydrogen, alkyl, fluoroalkyl,

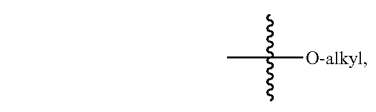
aminoalkyl,
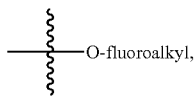
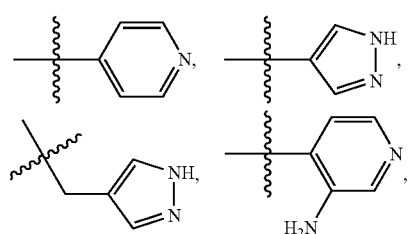
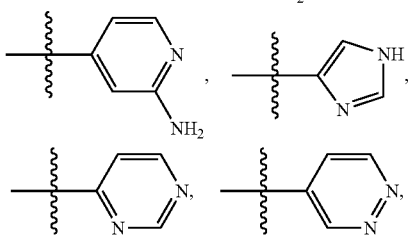
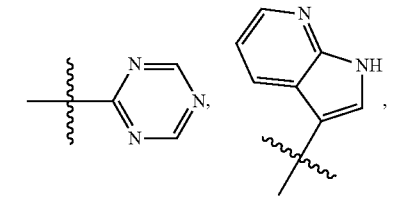
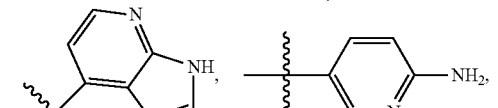
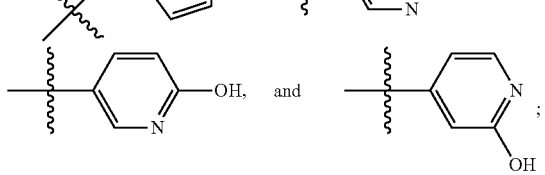
wherein no more than three of $R_{25}$, $R_{26}$, $R_{27}$, and $R_{28}$ can be hydrogen;
wherein the stereochemical configuration at a stereocenter in said compound is R, S, or a mixture thereof.
2. The compound of claim 1, wherein $R_1$ is selected from the group consisting of:
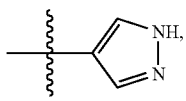 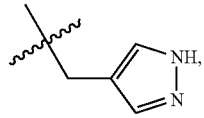
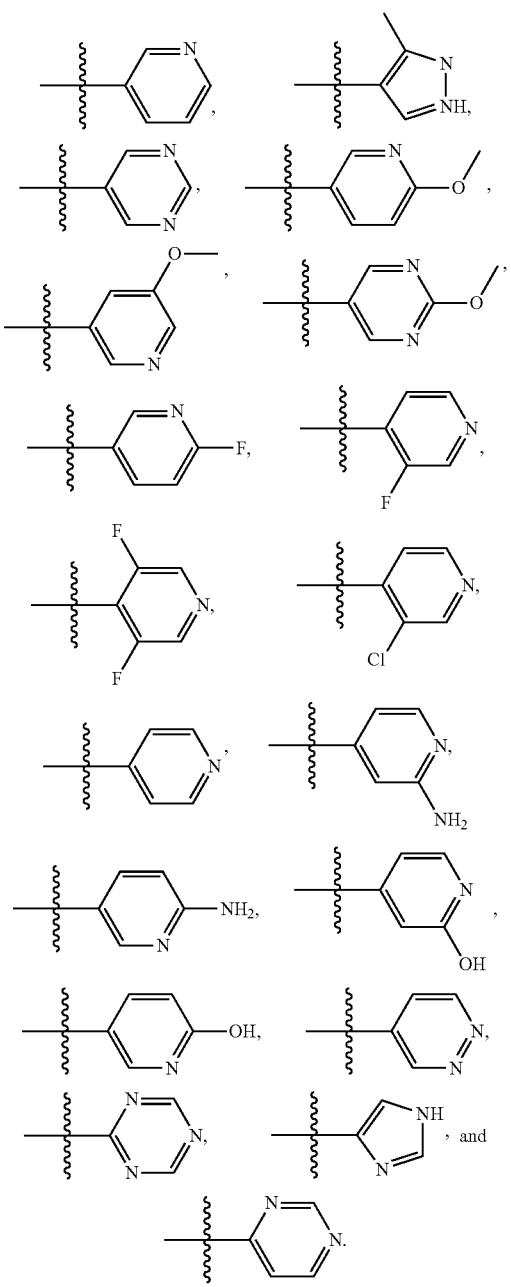
3. The compound of claim 1, wherein said compound is defined by a formula selected from the group consisting of:
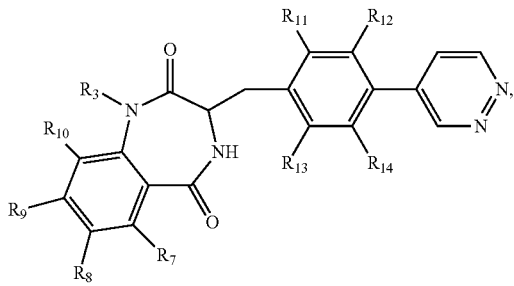

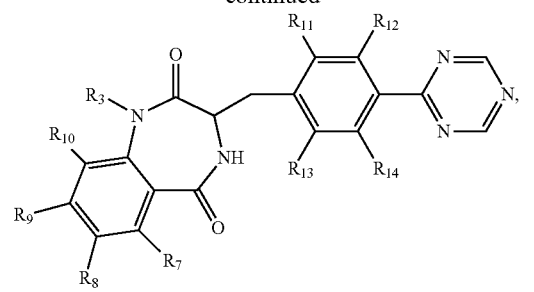
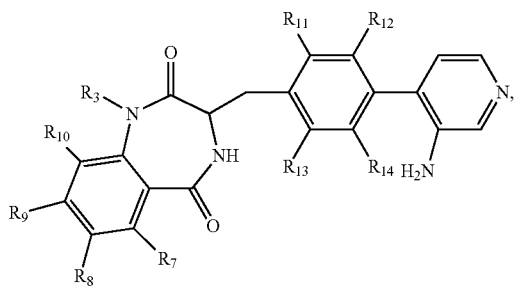
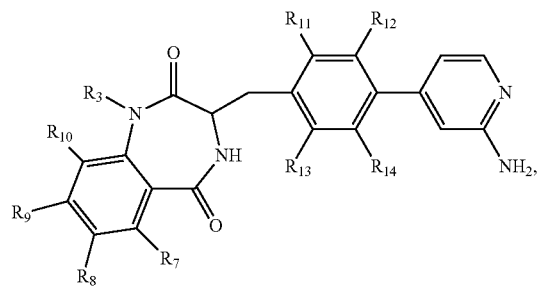
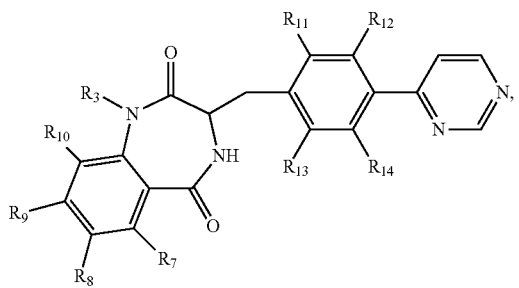
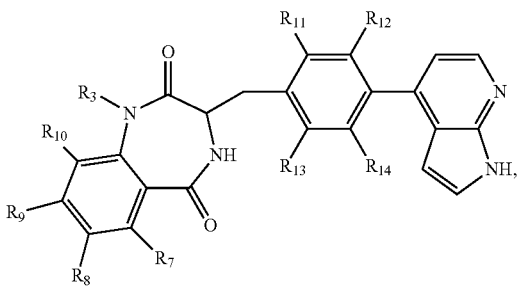
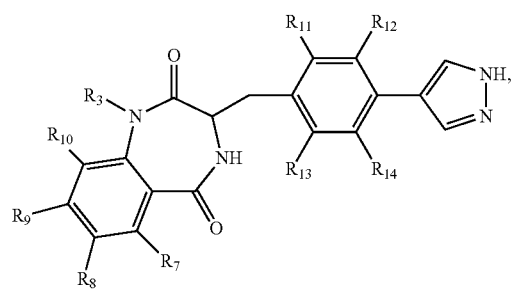
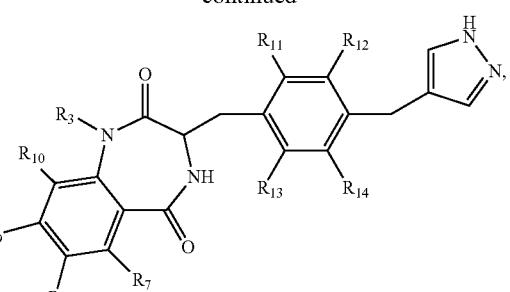
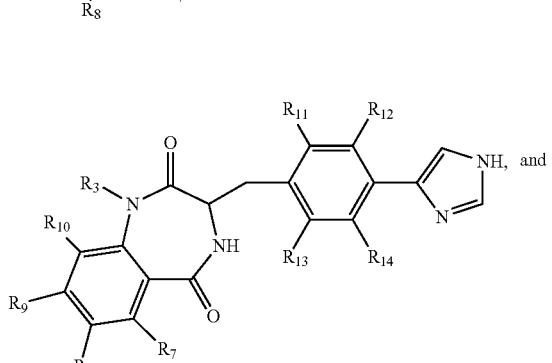
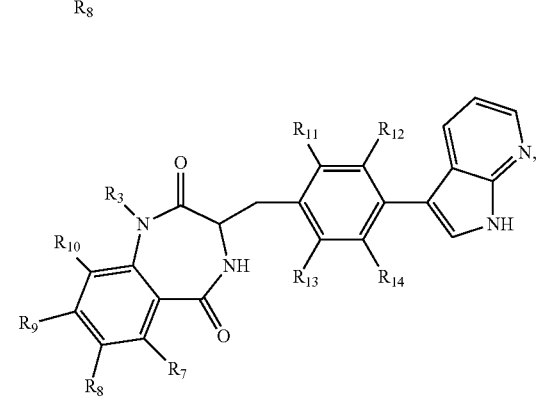
or a pharmaceutically acceptable salt thereof.
4. The compound of claim 1, wherein said compound is selected from the group consisting of:
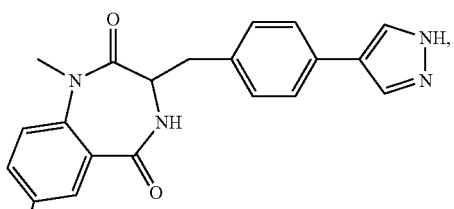
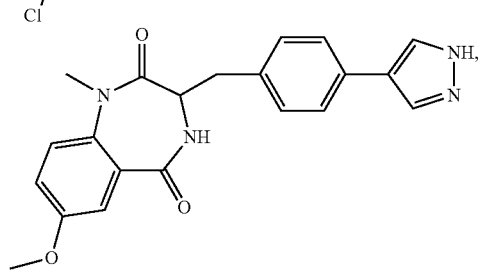

99
-continued
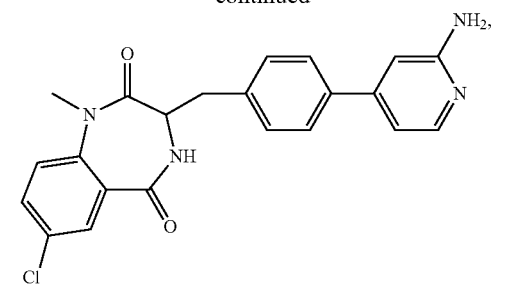
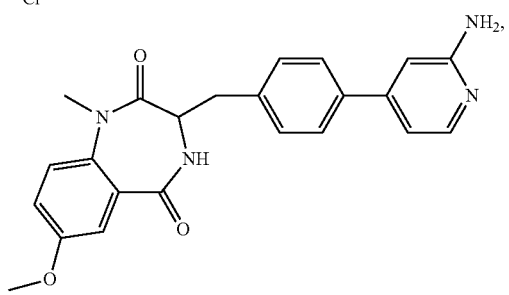
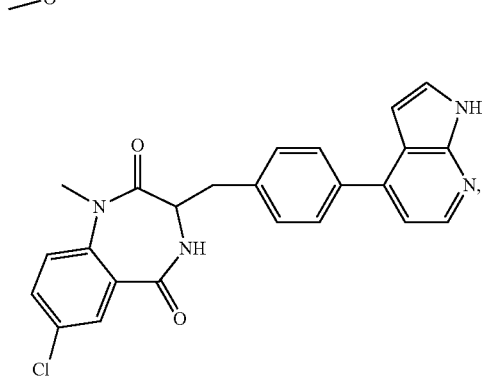
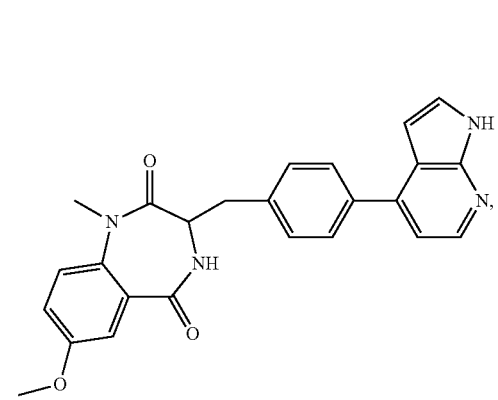
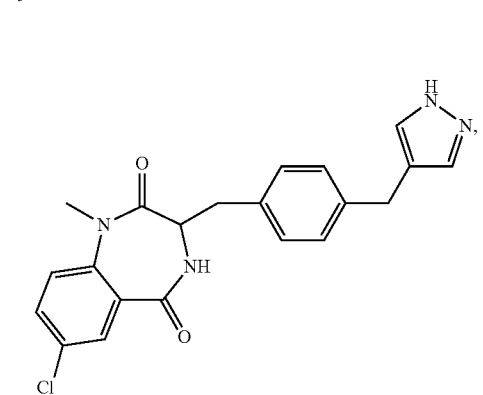
100
-continued
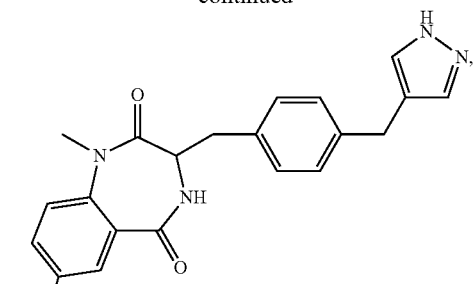
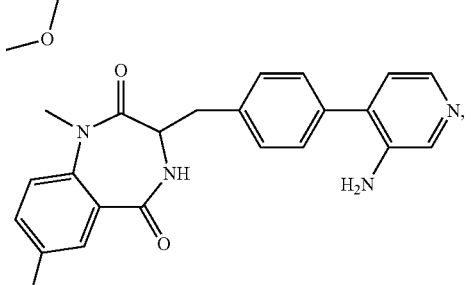
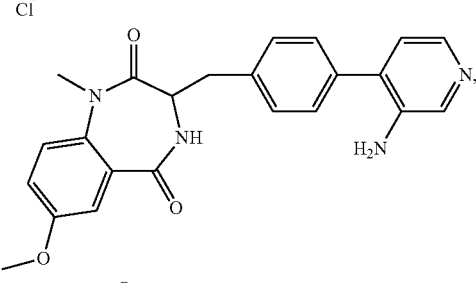
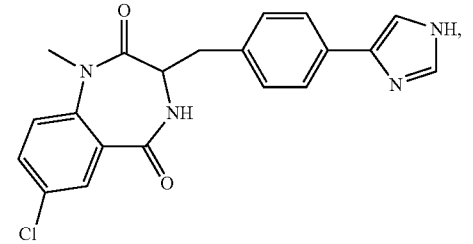
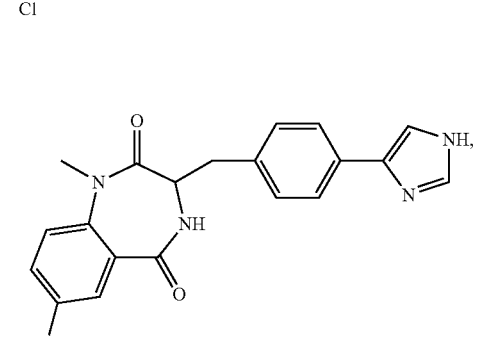
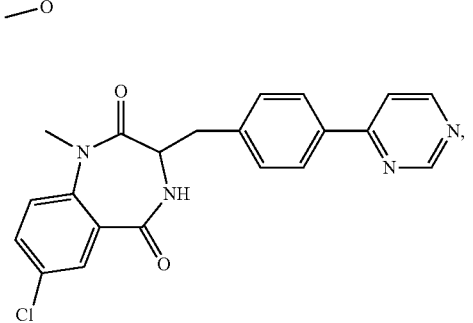

101
-continued
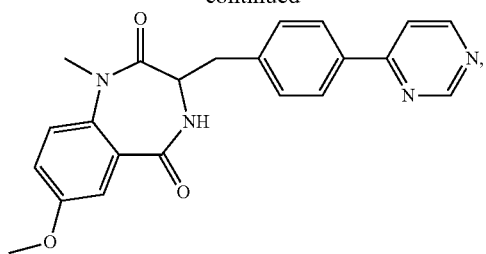
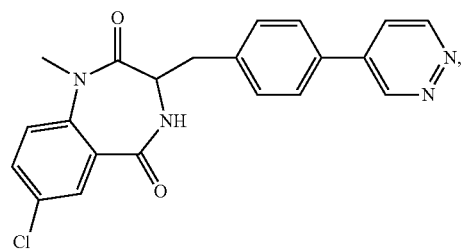
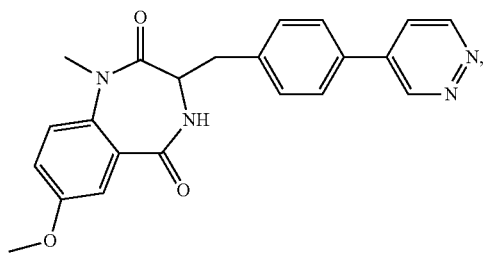
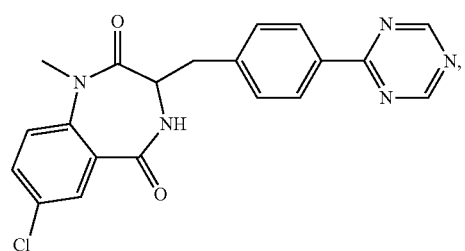
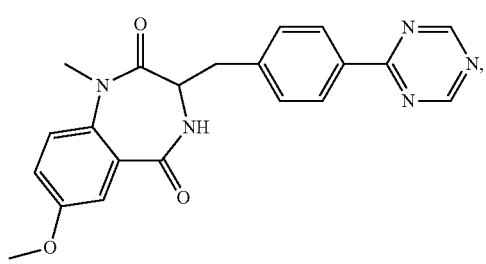
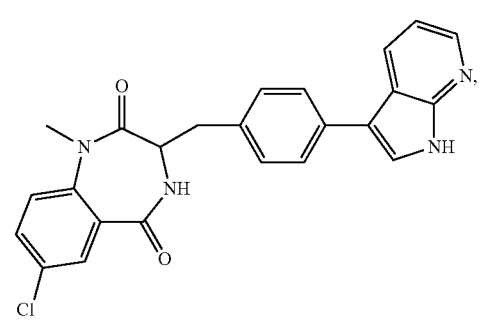
102
-continued
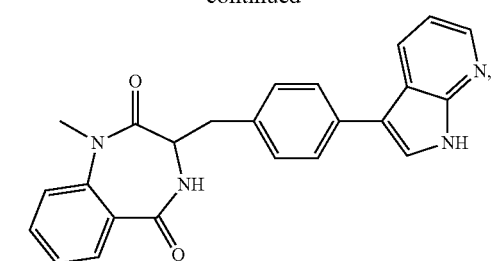
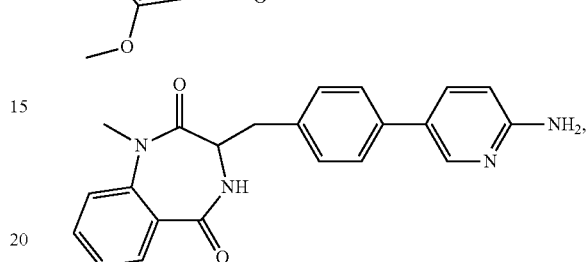
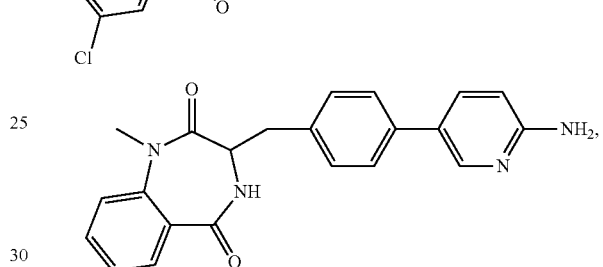
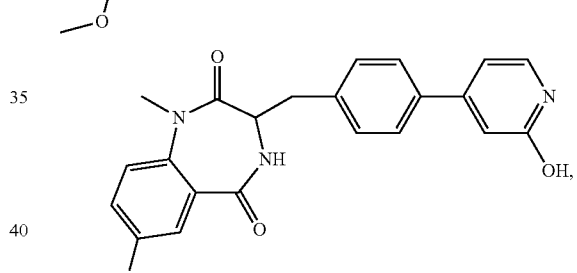
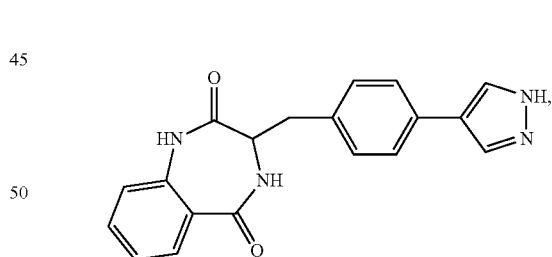
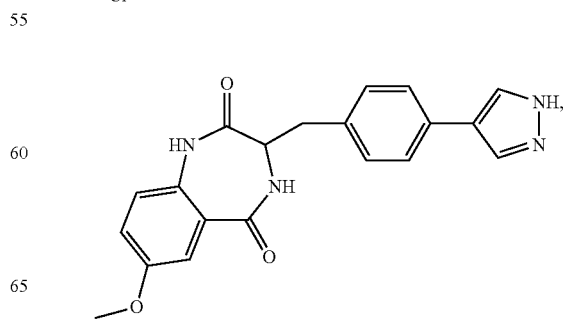

103
-continued
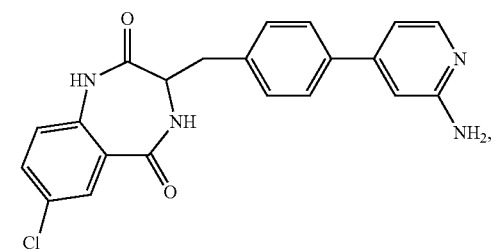
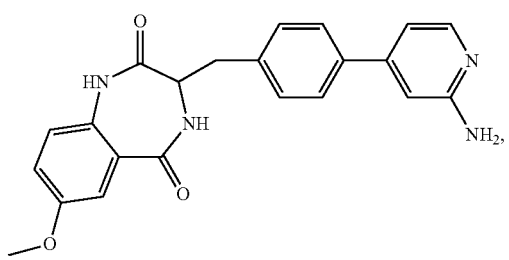
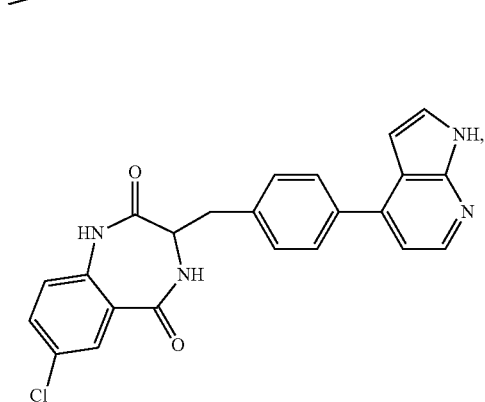
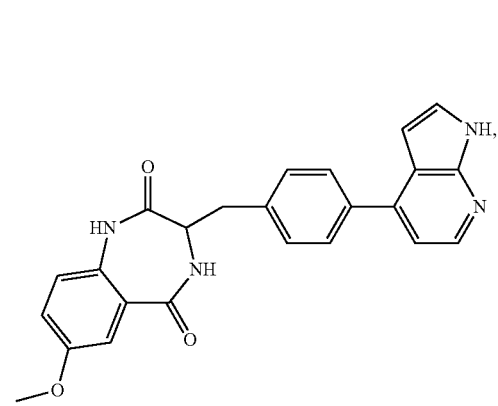
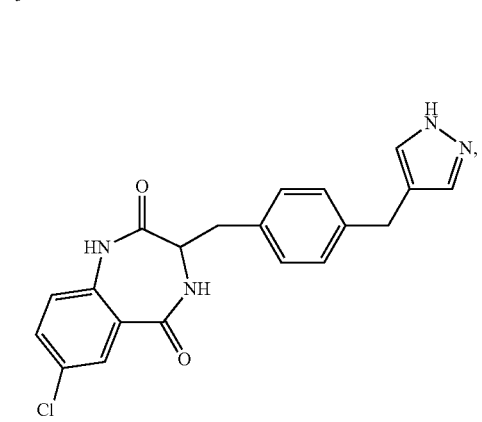
104
-continued
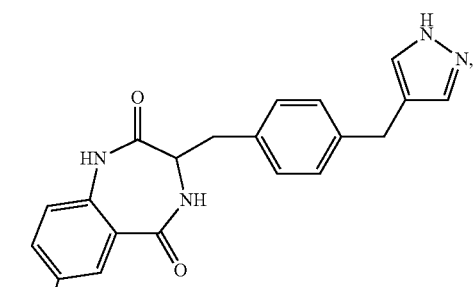
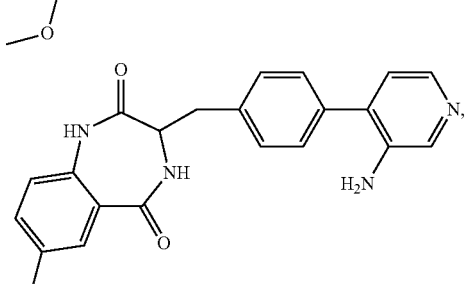
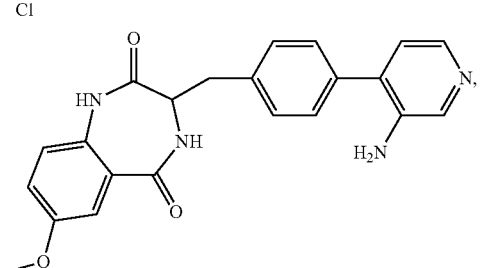
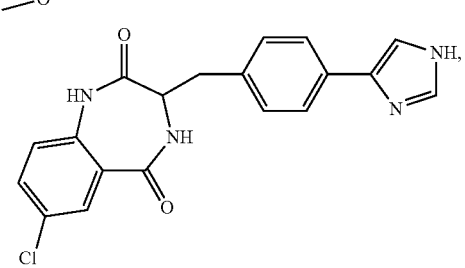
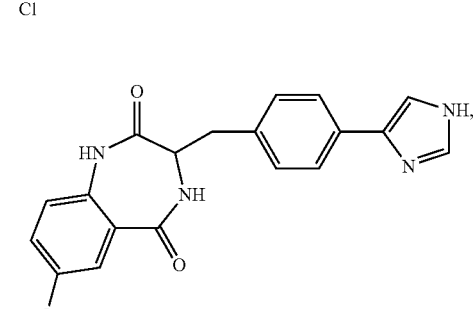
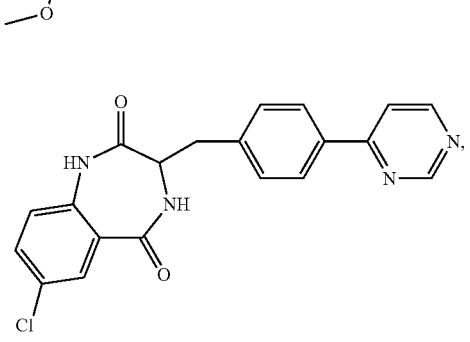

-continued

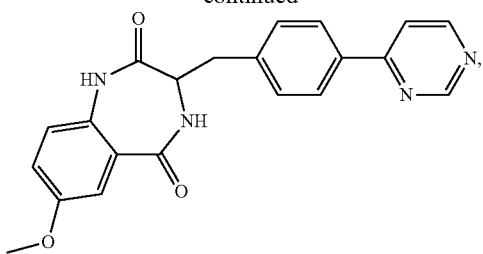

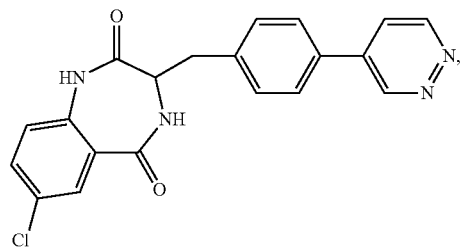

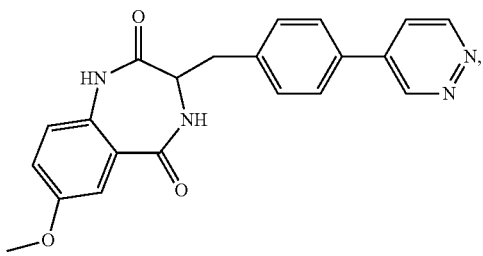

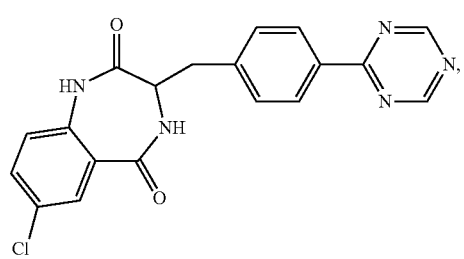

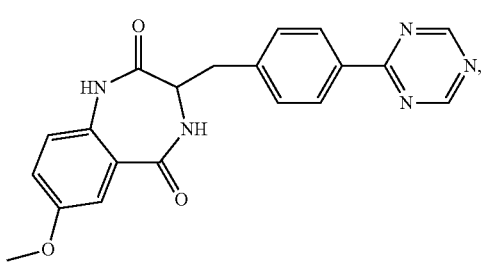

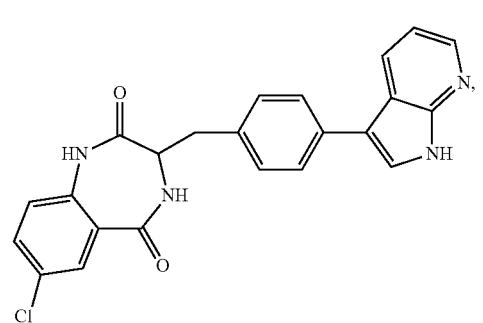

-continued

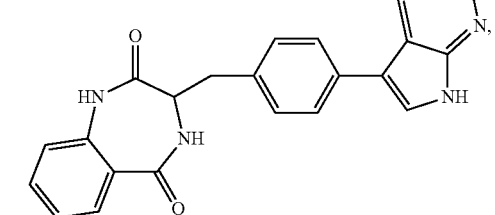

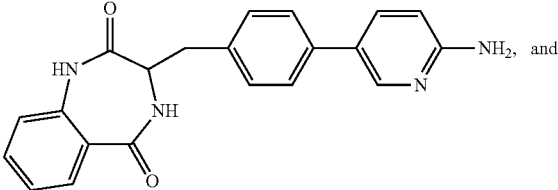

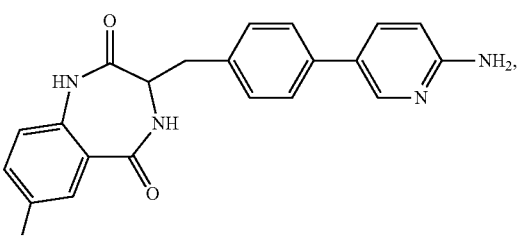

or a pharmaceutically acceptable salt thereof.

5. A pharmaceutical composition comprising one or more of the compounds defined in claim 1, or a pharmaceutically acceptable salt thereof, and one or more pharmaceutically acceptable carriers.

6. A method of treating a disorder comprising administering an effective amount of a pharmaceutical composition to a subject suffering from said disorder,
wherein said disorder is selected from the group consisting of a cardiovascular disorder, a smooth muscle related disorder, a granulomatosus disorder, an acute macrophage-mediated disease, and an autoimmune disorder,
wherein said cardiovascular disorder is selected from the group consisting of cerebral hemorrhage, peripheral vascular disease, pulmonary stenosis, and vasospasm, and hypertension, wherein said autoimmune disorder is selected from the group consisting of irritable bowel syndrome and systemic sclerosis,
wherein said pharmaceutical composition comprises a compound defined in claim 1, or a pharmaceutically acceptable salt thereof, and one or more pharmaceutically acceptable carriers.

7. The method of claim 6, wherein said vasospasm is selected from the group consisting of cerebral artery vasospasm, and coronary artery vasospasm.

8. The method of claim 6, wherein said hypertension is selected from the group consisting of pulmonary artery hypertension, and systemic arterial hypertension.

9. The method of claim 6, wherein said smooth muscle related disorder is selected from the group consisting of glaucoma and erectile dysfunction.

10. The method of claim 6, wherein said granulomatosus disorder is selected from the group consisting of sarcoidosis, and Wegener's granulomatosus.

11. The method of claim 6, wherein said acute macrophage-mediated disease is adult respiratory distress syndrome.

12. The method of claim 6, further comprising administering an additional agent for treating said disorder.

13. The method of claim 6, wherein said subject is a human subject.

14. A compound selected from the group consisting of:

(compound 1)
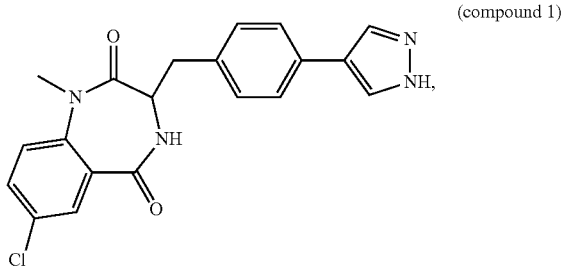

(compound 2)
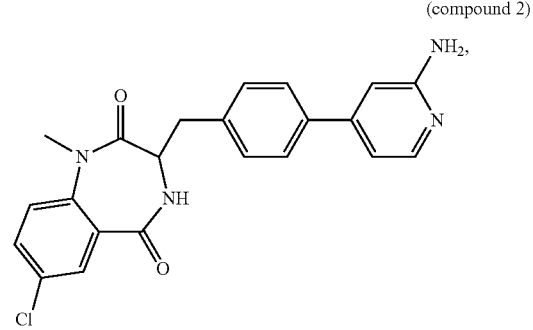

(compound 3)
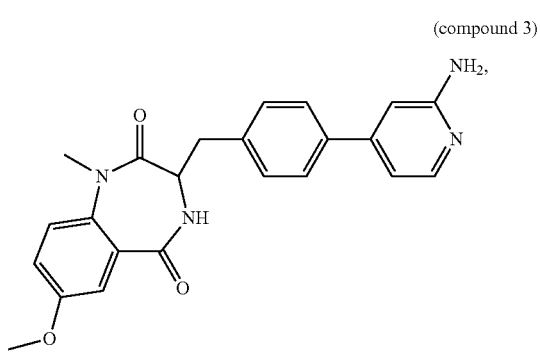

(compound 4)
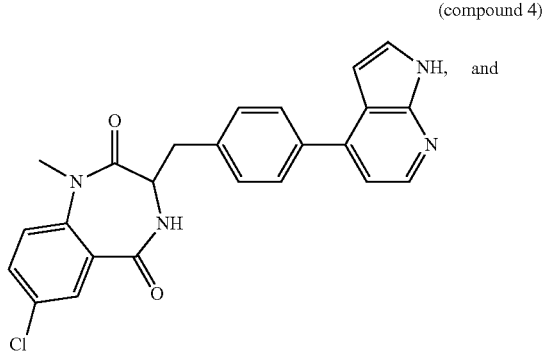

(compound 5)
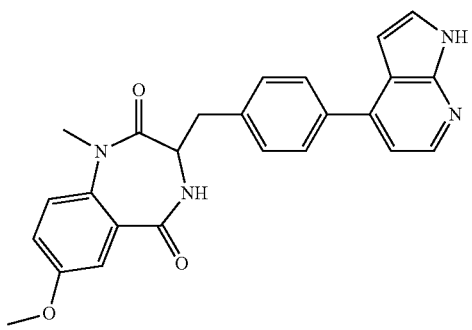

or a pharmaceutically acceptable salt thereof.

15. The compound of claim 3, wherein $R_7$ is H.

16. The compound of claim 3, wherein $R_9$ is H.

17. The compound of claim 3, wherein $R_{10}$ is H.

18. The compound of claim 3, wherein $R_7$, $R_9$, and $R_{10}$ are H.

19. The compound of claim 18, wherein $R_3$ is selected from the group consisting of H and alkyl.

20. The compound of claim 14, wherein the compound is selected from the group consisting of:

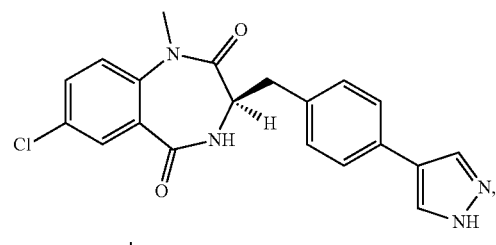

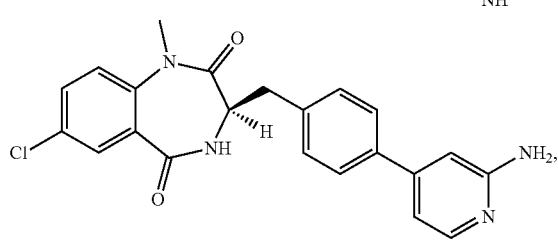

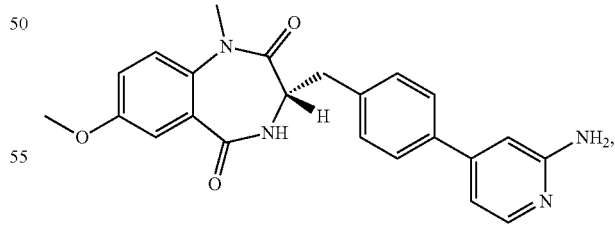

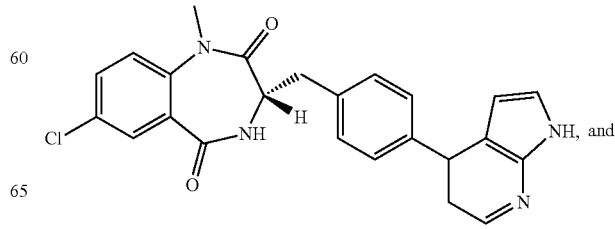

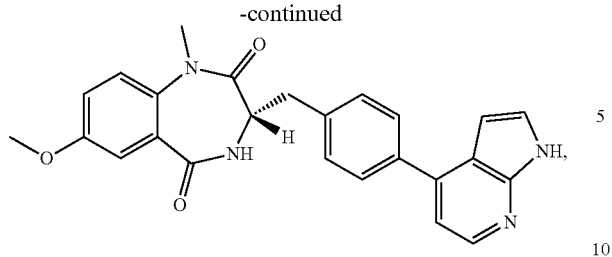
or a pharmaceutically acceptable salt thereof.
* * * * *